(12) United States Patent
Eggers et al.

(10) Patent No.: US 11,737,808 B2
(45) Date of Patent: Aug. 29, 2023

(54) MINIMALLY INVASIVE DIAGNOSTIC AND THERAPEUTIC EXCISION OF TISSUE

(71) Applicant: Eggers & Associates, LLC, Dublin, OH (US)

(72) Inventors: Philip E. Eggers, Dublin, OH (US); Andrew Eggers, Ostrander, OH (US)

(73) Assignee: Eggers & Associates, LLC, Dublin, OH (US)

( * ) Notice: Subject to any disclaimer, the term of this patent is extended or adjusted under 35 U.S.C. 154(b) by 1277 days.

(21) Appl. No.: 15/877,730

(22) Filed: Jan. 23, 2018

(65) Prior Publication Data

US 2018/0206902 A1    Jul. 26, 2018

Related U.S. Application Data

(60) Provisional application No. 62/449,161, filed on Jan. 23, 2017.

(51) Int. Cl.
*A61B 18/08* (2006.01)
*H02K 7/116* (2006.01)
(Continued)

(52) U.S. Cl.
CPC ............ *A61B 18/082* (2013.01); *H02K 7/116* (2013.01); *H02P 7/03* (2016.02); *H02P 7/285* (2013.01);
(Continued)

(58) Field of Classification Search
CPC ........... A61B 2018/00077; A61B 2018/00095; A61B 2018/00184; A61B 2018/00196; A61B 2018/00202; A61B 2018/00601; A61B 2018/1405; A61B 2018/1407; A61B 2018/141; A61B 2018/144; A61B 18/1402; A61B 17/221; A61B 17/2212;
(Continued)

(56) References Cited

U.S. PATENT DOCUMENTS

| | | | |
|---|---|---|---|
| 6,277,083 B1* | 8/2001 | Eggers | A61B 18/1482 600/564 |
| 6,471,659 B2* | 10/2002 | Eggers | A61B 18/1482 600/564 |
| 6,740,079 B1* | 5/2004 | Eggers | A61B 18/1206 606/34 |
| 2003/0225401 A1* | 12/2003 | Eggers | A61B 18/148 606/39 |

(Continued)

*Primary Examiner* — Ronald Hupczey, Jr.
*Assistant Examiner* — Bradford C. Blaise
(74) *Attorney, Agent, or Firm* — Emerson Thomson Bennett, LLC; Jerry K. Mueller, Jr.

(57) ABSTRACT

The recovery of an intact volume of tissue proceeds with a delivery cannula distal end positioned in confronting adjacency with the volume of tissue to be recovered. A tissue cutting and capture assembly formed of a plurality of metal leafs is deployed from the distal end of the delivery cannula. The tips of these leafs carry a pursing cable assembly, which is resistively heated by the passage of electrical current through the cable, attaining temperature level sufficient to thermally cut around and circumscribe the tissue volume. These pursing cables are tensioned to complete the envelopment of the tissue volumes by drawing the leaf tips together. An essential attribute of the disclosed apparatus is the confinement of the path of electrical conduction of constant current required to achieve tissue cutting to only those portions of the deploying and retracting resistively heated portion of the electrically conductive cutting and pursing cable that are in direct contact with tissue.

27 Claims, 23 Drawing Sheets

(51) Int. Cl.
*H02P 7/03* (2016.01)
*H02P 7/285* (2016.01)
*A61B 18/00* (2006.01)
*A61B 17/221* (2006.01)
*A61B 17/3205* (2006.01)

(52) U.S. Cl.
CPC ....... *A61B 17/221* (2013.01); *A61B 17/32056* (2013.01); *A61B 2017/2212* (2013.01); *A61B 2018/00077* (2013.01); *A61B 2018/00095* (2013.01); *A61B 2018/00184* (2013.01); *A61B 2018/00601* (2013.01); *A61B 2218/008* (2013.01)

(58) Field of Classification Search
CPC ... A61B 2218/008; H02P 7/03; H02P 7/2885; H02K 7/116
See application file for complete search history.

(56) References Cited

U.S. PATENT DOCUMENTS

| | | | |
|---|---|---|---|
| 2004/0024396 A1* | 2/2004 | Eggers | A61B 18/1482 606/39 |
| 2004/0030328 A1* | 2/2004 | Eggers | A61B 18/1206 606/34 |
| 2005/0027209 A1* | 2/2005 | Eggers | A61B 10/0283 600/564 |
| 2005/0033286 A1* | 2/2005 | Eggers | A61B 18/148 606/45 |
| 2005/0124915 A1* | 6/2005 | Eggers | A61B 10/0266 600/568 |
| 2007/0208338 A1* | 9/2007 | Eggers | A61B 18/1402 606/45 |
| 2017/0095286 A1* | 4/2017 | Vacha | A61B 18/148 |

* cited by examiner

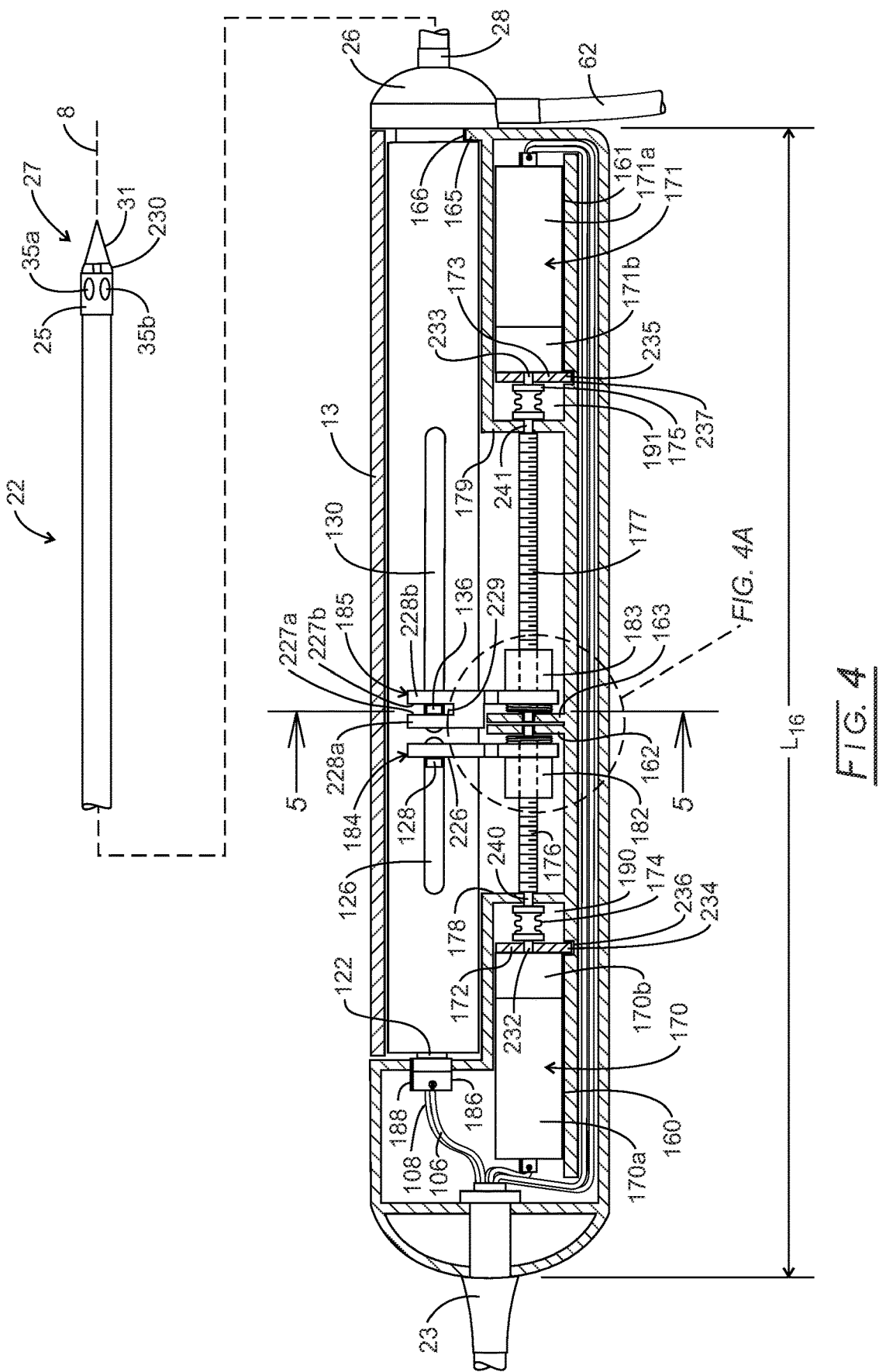

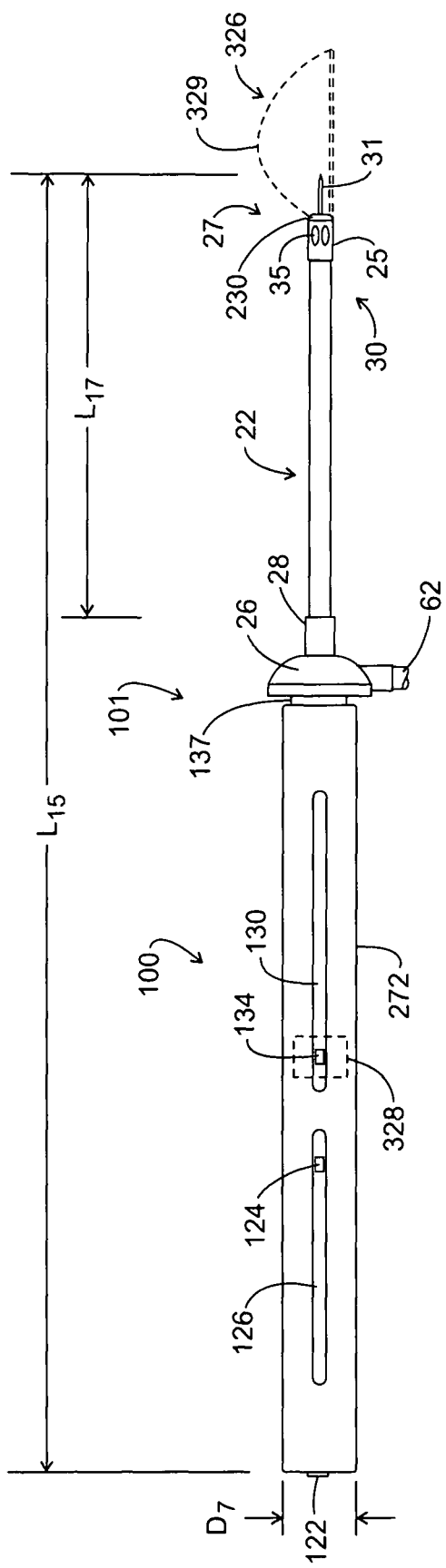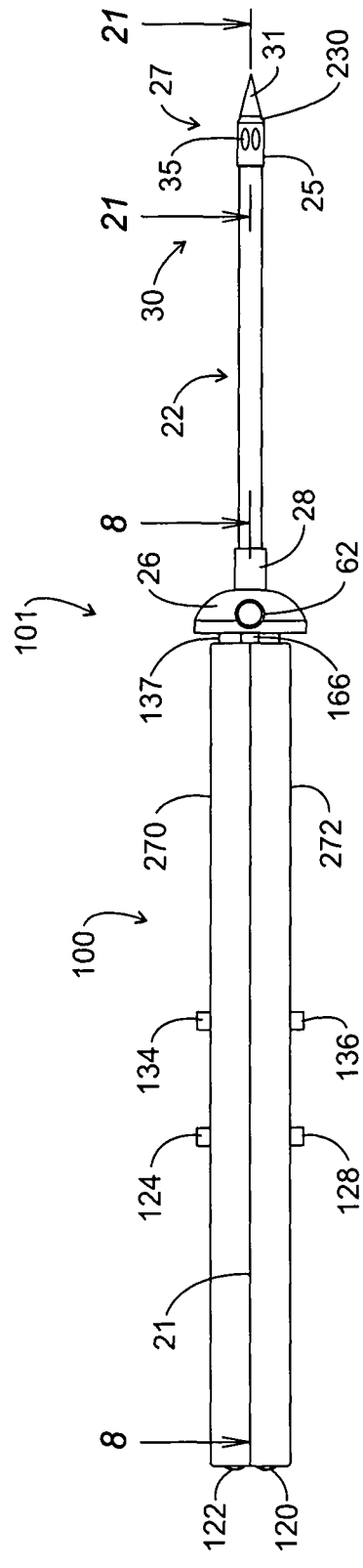

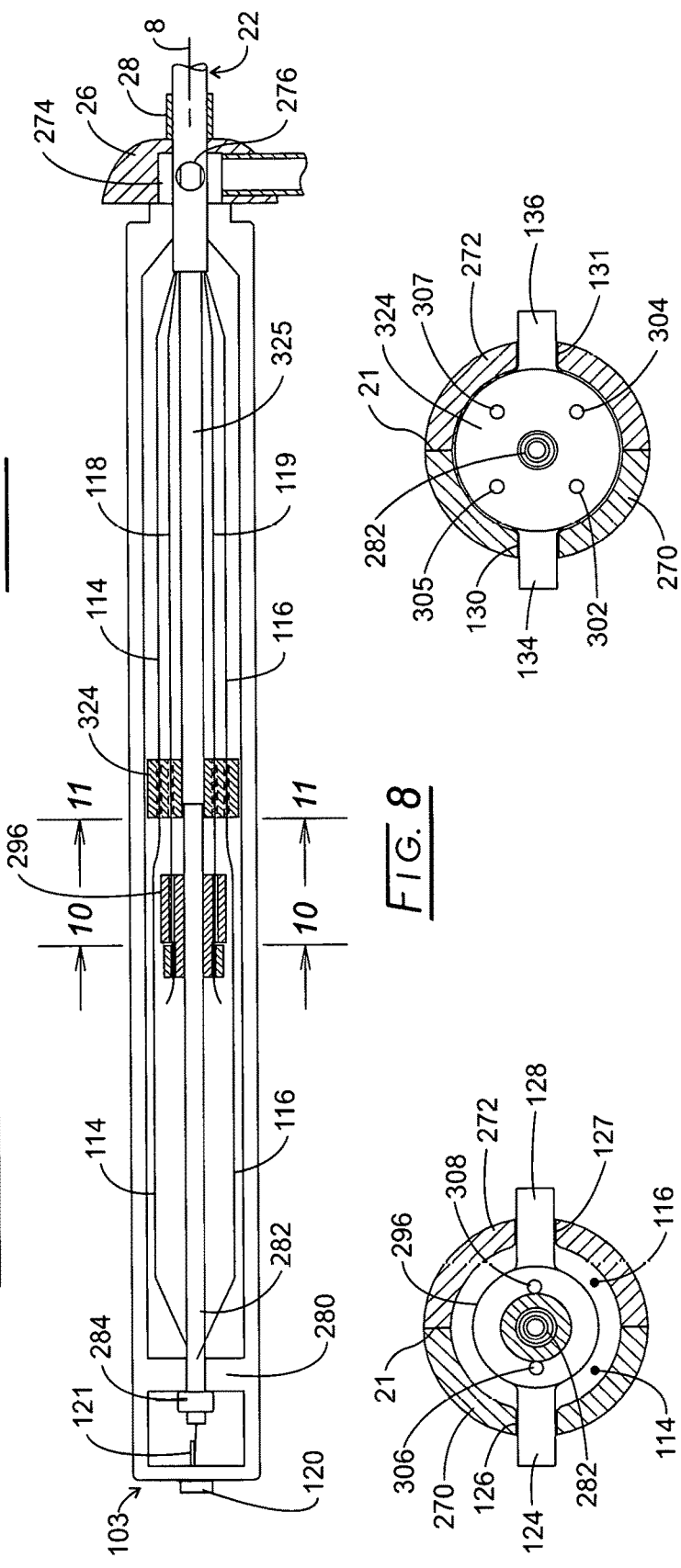
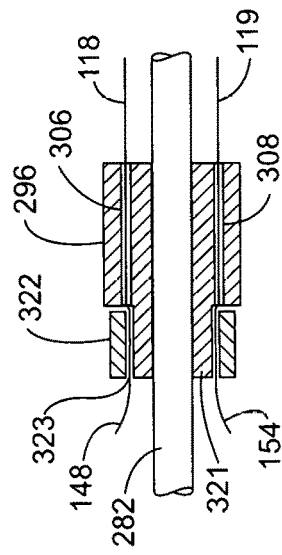
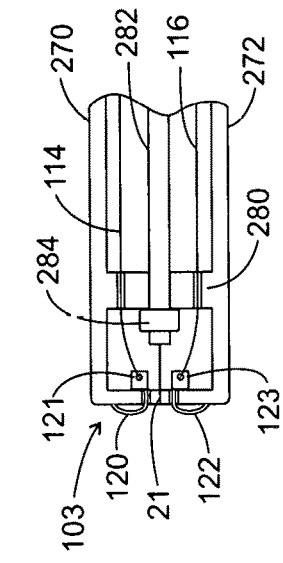
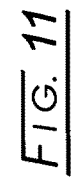

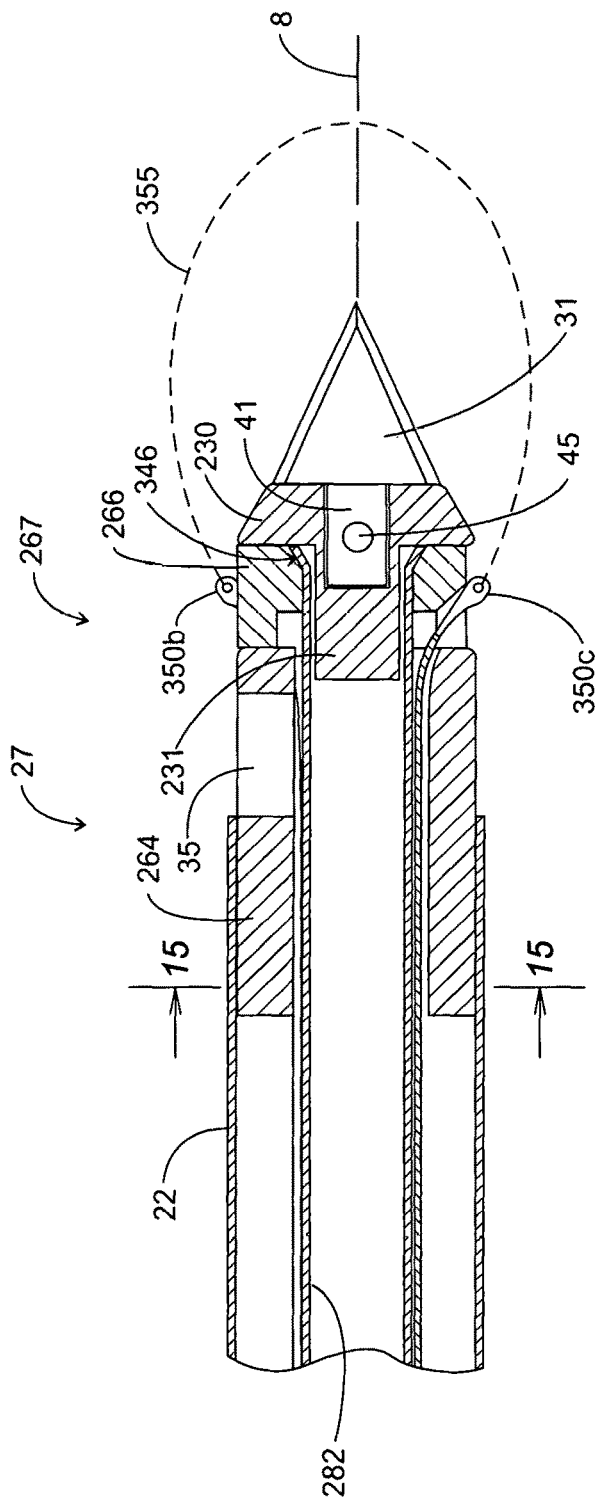
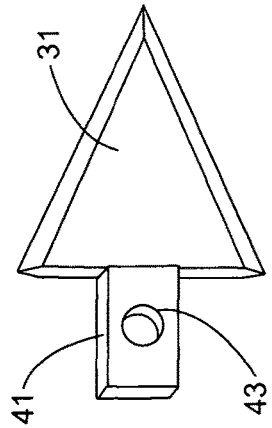
FIG. 12
FIG. 13
FIG. 14

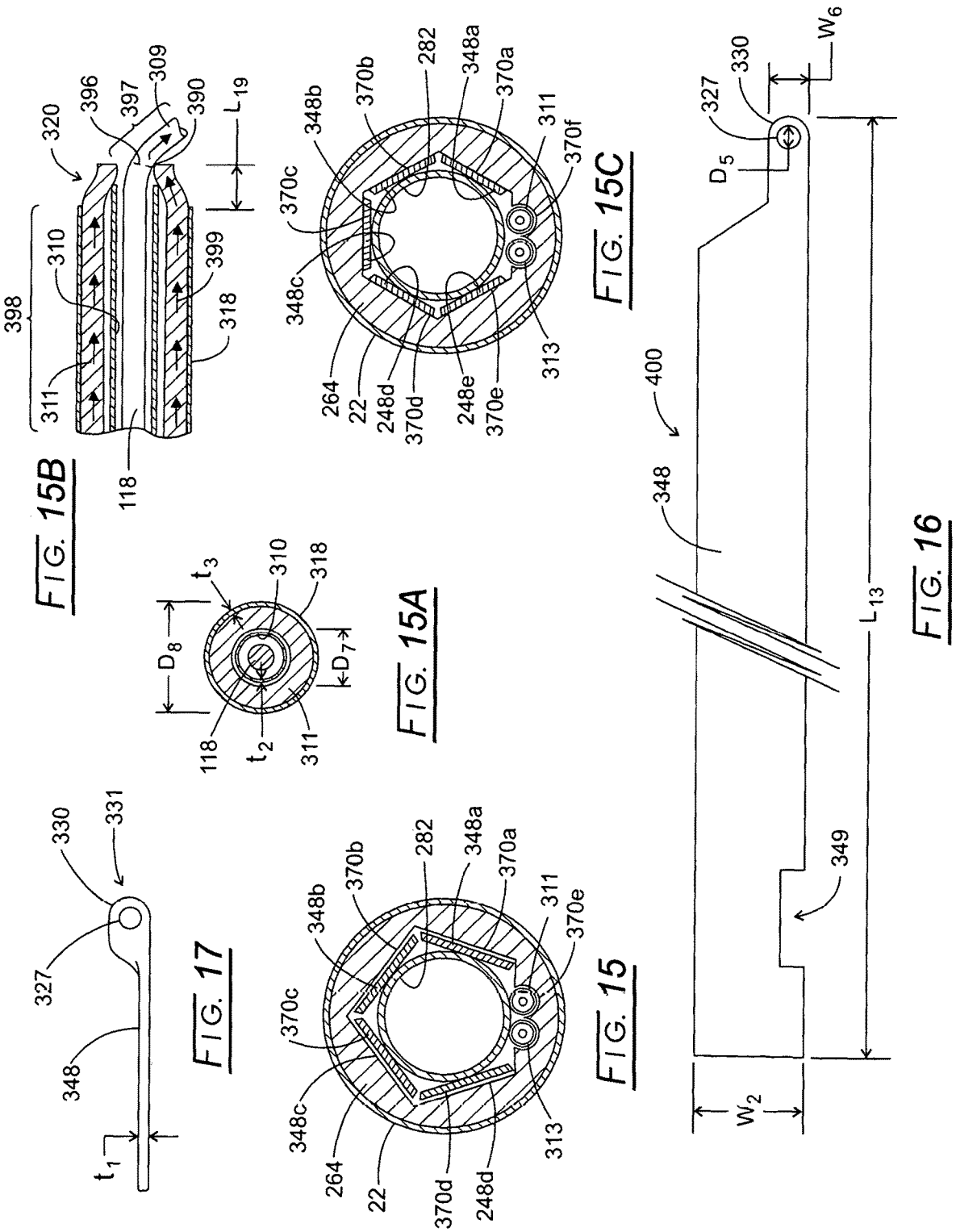

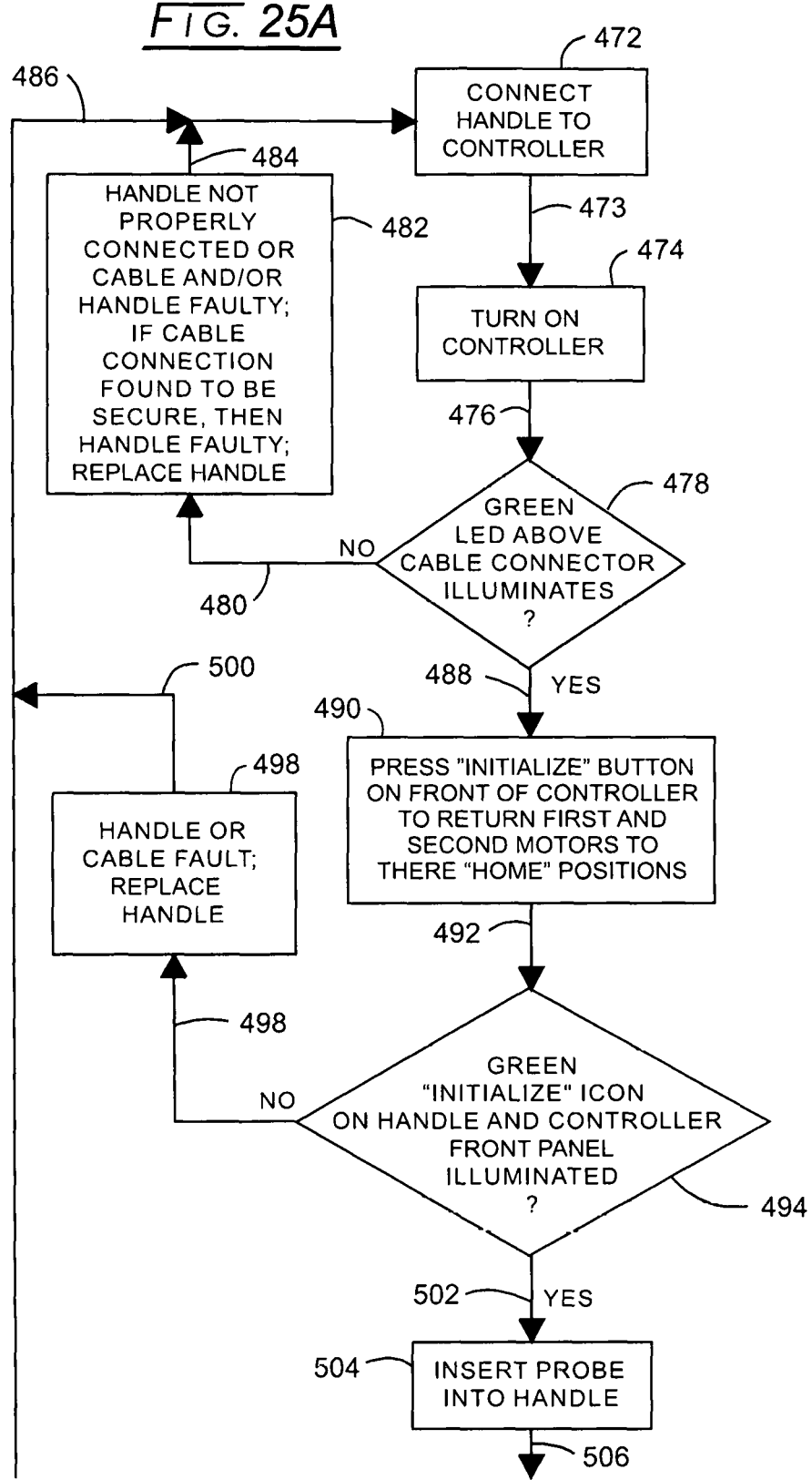

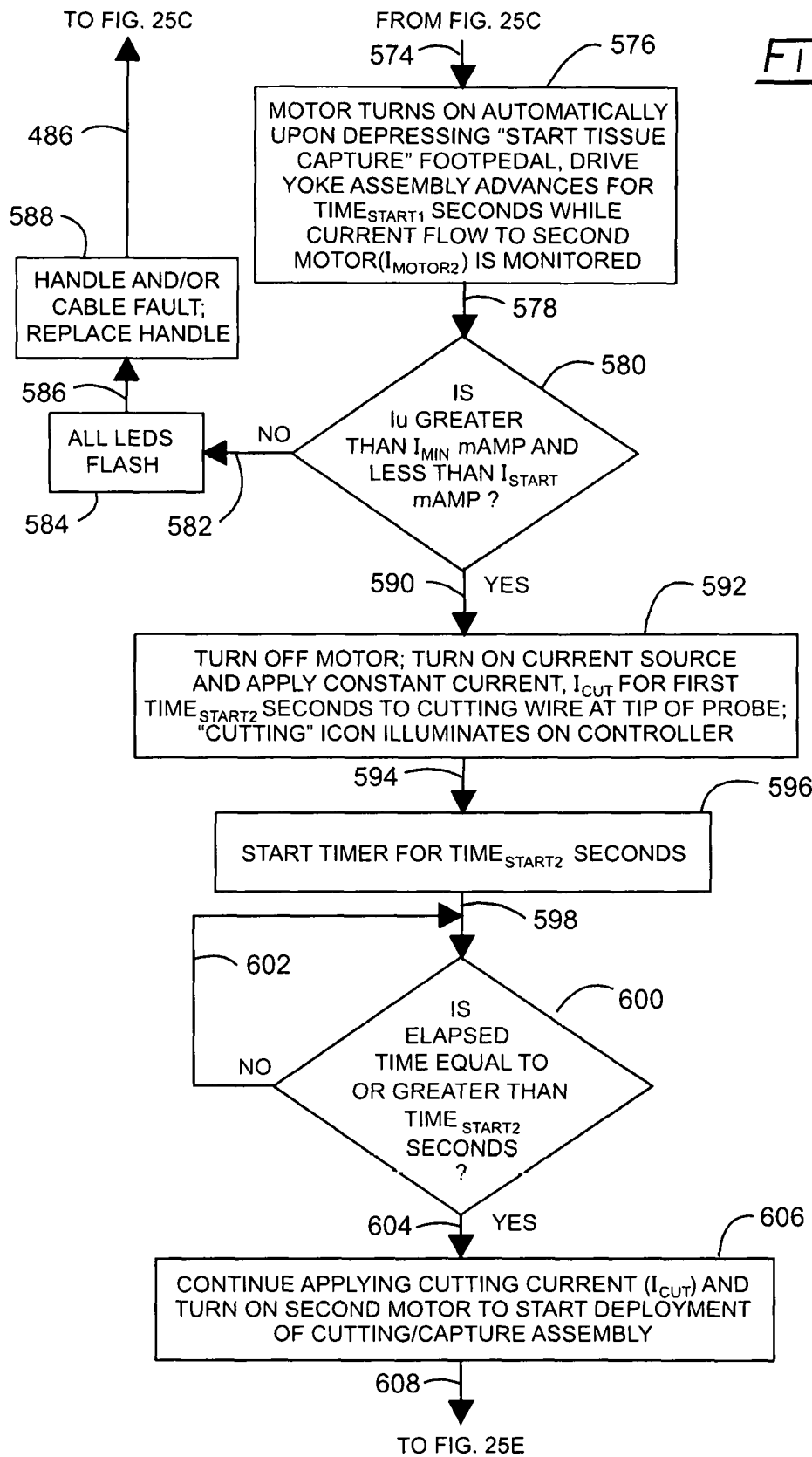

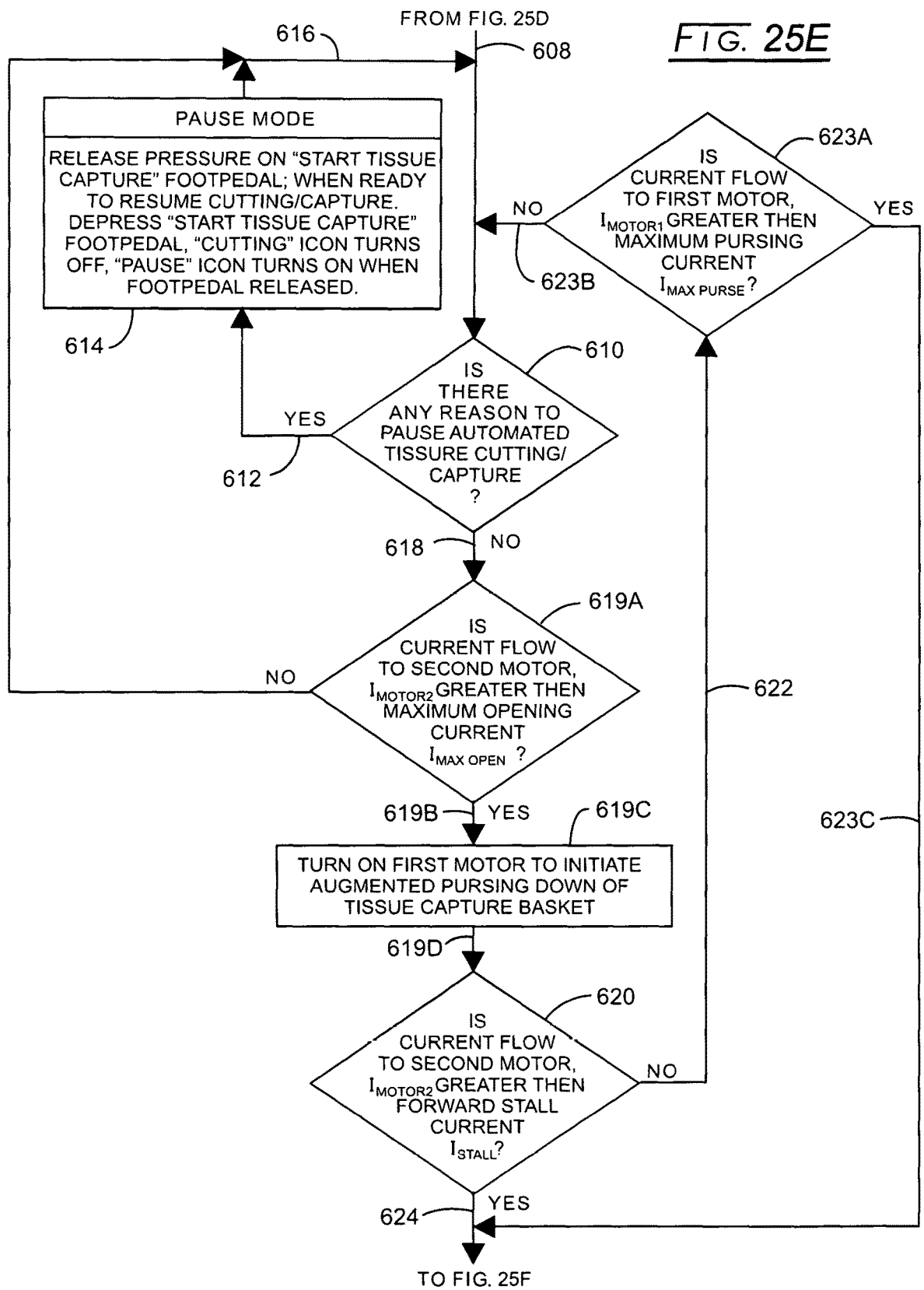

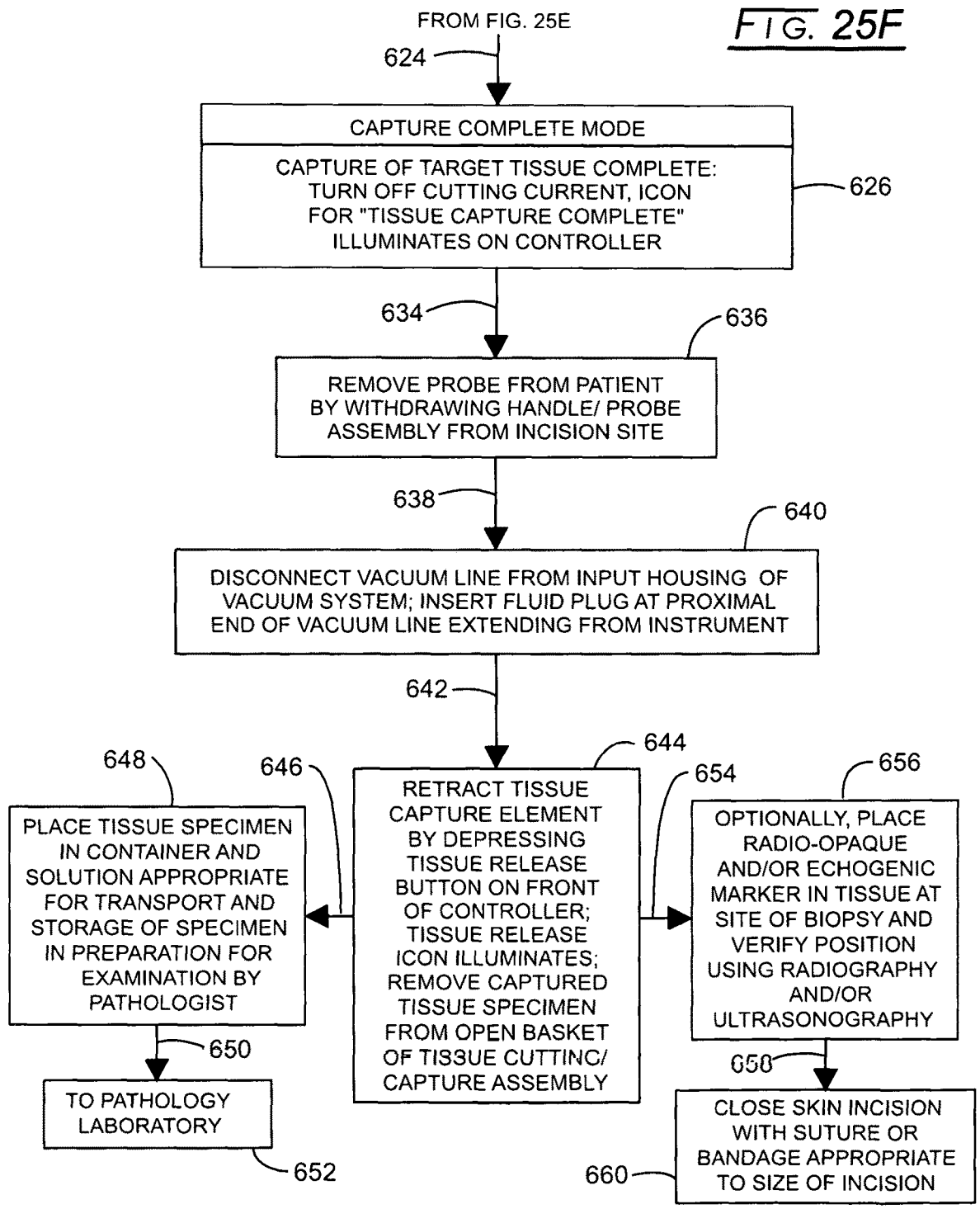

MINIMALLY INVASIVE DIAGNOSTIC AND THERAPEUTIC EXCISION OF TISSUE

CROSS-REFERENCE TO RELATED APPLICATIONS

This application claims benefit of provisional application 62/449,161 filed Jan. 23, 2017.

STATEMENT REGARDING FEDERALLY SPONSORED RESEARCH

Not applicable.

BACKGROUND

It is estimated that one out of eight women will face breast cancer at some point during their lifetime, and for women age 40-55, breast cancer is the leading cause of death. While methods for detecting and treating breast cancer initially were crude and unsophisticated, advanced instrumentation and procedures now are available which provide more positive outcomes for patients.

In the 1800s the only treatment for breast cancer was removal of the entire breast. Given that the sole method of detection and diagnosis was palpation, treatment was only directed when the breast tumor was well advanced. Modified radical mastectomies are still performed today for patients with invasive cancer, such a procedure involving the removal of the entire breast and some or all of the axillary lymph nodes. Radical or modified radical mastectomies involve serious trauma for the patient during surgery, with the severest cosmetic results after surgery.

Another surgical option upon the discovery of malignant tumor is what is referred to as breast conserving surgery, which also is referred to as lumpectomy, tumorectomy, segmental mastectomy and local excision. Meant to address the cosmetic concerns associated with removal of the breast, only the primary tumor and a margin of surrounding normal breast tissue is removed. Determining the proper amount of tissue to be removed involves balancing the need to take sufficient tissue to prevent recurrence with the desire to take as little tissue as possible to preserve the best cosmetic appearance. A more limited nodal dissection now is performed with the primary purpose being staging rather than therapy. While an improvement over radical mastectomy, breast-conserving surgery still involves the removal of large sections of breast tissue. Risks associated with such surgery include wound infection, seroma formation, mild shoulder dysfunction, loss of sensation in the distribution of the intercostobrachial nerve, and edema of the breast and arm. For more information on invasive tumor therapy, see:
 (1) Harris, Jay R., et al. "Cancer of the Breast." *Cancer: Principles and Practices of Oncology, Fourth Edition.* Eds. DeVita, et al. Philadelphia: J. B. Lippincott Co., 1993. 1264-1285.
 (2) Jobe, William E. "Historical Perspectives." *Percutaneous Breast Biopsy.* Eds. Parker, et al. New York: Raven Press, 1993. 1-5.

Mastectomies and breast-conserving surgeries generally are procedures utilized for invasive tumors. Advances in tumor detection, however, have radically changed the course of diagnosis and treatment for a tumor. With the advent of imaging devices, such as the mammogram, suspect tumor may be located when it is of relatively small size. Today, tumor detection generally involves both a mammogram and a physical examination, which takes into account a number of risk factors including family history and prior occurrences. Technical improvements in mammogram imaging include better visualization of the breast parenchyma with less exposure to radiation, improvements in film quality and processing, improved techniques for imaging, better guidelines for the diagnosis of cancer and greater availability of well-trained mammographers. With these advancements in imaging technology, a suspect tumor may be detected which is 5 mm or smaller. More recently substantial progress has been witnessed in the technical disciplines of magnetic resonance imaging (MRI) and ultrasound imagining. With these advances, the location of a lesion is observable as diagnostic or therapeutic procedures are carried out.

In the past, because a tumor normally was not discovered until it had reached an advanced stage, the issue of whether a tumor was malignant or benign did not need to be addressed. With the ability to locate smaller areas of suspect tumor, this issue becomes of critical importance, particularly in light of the fact that only 20% of small, non-invasive tumors are malignant. Tumors identified as being benign may be left in situ with no excision required, whereas action must be taken to excise suspect tissue confirmed to be malignant. In view of the value of classifying a tumor as malignant or benign, breast biopsy has become a much-utilized technique with over 1 million biopsies being performed annually in the United States. A biopsy procedure involves the two step process of first locating the tumor then removing part or all of the suspect tissue for examination to establish precise diagnosis.

Improvements in the detection of suspicious lesions in the breast are described in U.S. Patent Application No. US2006/ 0036173 published Feb. 16, 2006. In this patent application ultrasonic scanning and diagnostics for cellular tissue are disclosed. An ultrasonic probe is moved across cellular tissue at a rate that is synchronized with the image capture rate of the ultrasonic scanner, to achieve a contiguous and complete set of scan images of the tissue. The probe can be held in a single position as it is moved across the tissue, or it can be dynamically adjusted during the scan to provide optimal contact with the scanned tissue. The image data are captured and converted to a format that is easily stored and compatible with a viewer. The viewer allows playback of the scanned images in a manner that is optimized for screening for cancers and other anomalies. A location function allows the user to select a point of interest on an individual scan image, and choose another known reference point, and the function calculates and provides the distance from the reference point to the point of interest in three dimensions. The system can be used for virtually any tissue, but can also be optimized for breast cancer screening. Clinical studies using the method and apparatus described in this patent application have revealed that suspicious and potentially malignant lesions in the human breast can be detected having maximum dimensional extents as small as 2 to 3 mm. This non-invasive diagnostic imaging capability would enable the complete excision of such small lesions surrounded by healthy margins of tissue in volumes as small as 15 to 20 mm using minimally invasive excisional methods.

One biopsy option available upon detection of a suspect tumor is an open surgical biopsy or excisional biopsy. Prior to surgery, a radiologist, using mammography, inserts a wire into the breast to locate the tumor site. Later during surgery, the surgeon makes an incision in the breast and removes a large section of breast tissue, including the suspect tissue and a margin of healthy tissue surrounding the tumor. As with other similar procedures, such as those described above, open surgery may result in high levels of blood loss, scarring at the location of the incision and permanent disfigurement, due to the removal of relatively large amounts of tissue. Because of the critical prognostic significance of tumor size, the greatest advantage of the excisional biopsy is that the entire area of the suspect tumor is removed. After being removed and measured, the specimen is typically transected by a pathologist in a plane that should bisect a tumor, if present, and then the margin between tumor and healthy tissue is examined. Microscopic location of carcinoma near the margin provides information for future prognosis. Thus the pathology laboratory is oriented to the morphological aspect of analysis, i.e. the forms and structures of involved tissue. For information on pathology of breast biopsy tissue, see:

(3) Rosen, Paul Peter. Rosen's Breast Pathology. Philadelphia: Lippincott-Raven Publishers, 1997. 837-858.

Other less invasive options are available which avoid the disadvantages associated with open surgery. One such non-invasive option is that of needle biopsy, which may be either fine needle aspiration or large core. Fine needle aspiration (FNA) is an office procedure in which a fine needle, for example of 21 to 23 gauge, having one of a number of tip configurations, such as the Chiba, Franzeen or Turner, is inserted into the breast and guided to the tumor site by mammography or stereotactic imaging. A vacuum is created and the needle moved up and down along the tumor to assure that it collects targeted cellular material. Generally, three or more passes will be made to assure the collection of a sufficient sample. Then, the needle and the tissue sample are withdrawn from the breast.

The resulting specimen is subject to a cytological assay, as opposed to the above-noted morphological approach. In this regard, cell structure and related aspects are studied. The resultant analysis has been used to improve or customize the selection of chemotherapeutic agents with respect to a particular patient. While a fine needle aspiration biopsy has the advantages of being a relatively simple and inexpensive office procedure, there are some drawbacks associated with its use. With fine needle aspiration, there is a risk of false-negative results, which most often occurs in cases involving extremely fibrotic tumor. In addition, after the procedure has been performed there may be insufficient specimen material for diagnosis. Finally, with fine needle aspiration alone the entire area of suspect tissue is not removed. Rather, fragmented portions of tissue are withdrawn which do not allow for the same type of pathological investigation as the tissue removed during an open surgery biopsy.

This limitation also is observed with respect to large core needle biopsies. For a large core needle biopsy, a 14 to 18-gauge needle is inserted in the breast having an inner trocar with a sample notch at the distal end and an outer cutting cannula. Similar to a fine needle aspiration, tissue is drawn through the needle by vacuum suction. These needles have been combined with biopsy guns to provide automated insertion that makes the procedure shorter and partially eliminates location mistakes caused by human error. Once inserted, multiple contiguous tissue samples may be taken at a time.

Samples taken during large core needle biopsies may be anywhere from friable and fragmented to large pieces 20 to 30 mm long. These samples may provide some histological data, unlike fine needle aspiration samples; however, they still do not provide the pathological information available with an open surgical biopsy specimen. Further, as with any mechanical cutting device, excessive bleeding may result during and following the procedure. Needle biopsy procedures are discussed in:

(4) Parker, Steve H. "Needle Selection" and "Stereotactic Large-Core Breast Biopsy." *Percutaneous Breast Biopsy*. Eds. Parker, et al. New York: Raven Press, 1993. 7-14 and 61-79.

A device which is somewhere between a needle biopsy and open surgery is referred to as the Advanced Breast Biopsy Instrumentation (ABBI). With the ABBI procedure, the practitioner, guided by stereotactic imaging, removes a core tissue sample of 5 mm to 20 mm in diameter. While the ABBI has the advantage of providing a large tissue sample, similar to that obtained from an open surgical biopsy, the cylindrical tissue sample is taken from the subcutaneous tissue to an area beyond the suspect tumor. For tumors embedded more deeply within the breast, the amount of tissue removed is considerable. In addition, while less expensive than open surgical biopsy, the ABBI has proven expensive compared to other biopsy techniques, and it has been noted that the patient selection for the ABBI is limited by the size and location of the tumor, as well as by the presence of very dense parenchyma around the tumor. For discussion on the ABBI, see:

(5) Parker, Steve H. "The Advanced Breast Biopsy Instrumentation: Another Trojan Horse?" Am. J. Radiology 1998; 171: 51-53.

(6) D'Angelo, Philip C., et al. "Stereotactic Excisional Breast Biopsies Utilizing the Advanced Breast Biopsy Instrumentation System." Am J Surg. 1997; 174: 297-302.

(7) Ferzli, George S., et al. "Advanced Breast Biopsy Instrumentation: A Critique." J Am Coll Surg 1997; 185: 145-151.

Another biopsy device has been referred to as the Mammotome and the Minimally Invasive Breast Biopsy (MIBB). These devices carry out a vacuum-assisted core biopsy wherein fragments of suspect tissue are removed with an 11 to 14-gauge needle. While being less invasive, the Mammotome and MIBB yields only a fragmentary specimen for pathological study. These devices therefore are consistent with other breast biopsy devices in that the degree of invasiveness of the procedure necessarily is counterbalanced against the need for obtaining a tissue sample whose size and margins are commensurate with pathology requirements for diagnosis and treatment.

Another excisional biopsy device is described in U.S. Pat. No. 6,022,362, and includes a tubular member having a window near a distal tip thereof; a cutting tool, a distal end of the cutting tool being attached near the distal tip of the tubular member, at least a distal portion of the cutting tool being configured to selectively bow out of the window and to retract within the window; and a tissue collection device externally attached at least to the tubular member, the tissue collection device collecting tissue excised by the cutting tool as the biopsy device is rotated and the cutting tool is bowed. An excisional biopsy method for soft tissue includes the steps of inserting a generally tubular member into the tissue, the tubular member including a cutting tool adapted to selectively bow away from the tubular member and an external tissue collection device near a distal tip of the tubular member; rotating the tubular member; selectively varying a degree of bowing of the cutting tool; collecting tissue severed by the cutting tool in the tissue collection device; and retracting the tubular member from the soft tissue. The tubular member may include an imaging transducer and the method may include the step of displaying information received from the transducer on a display device and the step of varying the degree of bowing of the cutting tool based upon the displayed information from the imaging transducer. Alternatively, the imaging transducer may be disposed within a removable transducer core adapted to fit within the tubular member.

Yet another minimally invasive approach to accessing breast lesions wherein the lesion is partially removed or removed in its entirety for diagnostic as well as therapeutic purposes has been described in U.S. Pat. No. 6,277,083 by Eggers, et al., entitled "Minimally Invasive Intact Recovery Of Tissue", issued Aug. 21, 2001. The instrument described includes a tubular delivery cannula of minimum outer diameter, the tip of which is positioned in confronting adjacency with a tissue volume to be removed. Following such positioning, the electrosurgically excited leading edge of an electrically conducting cable supported at the distal ends of leaf members is extended forwardly from the instrument tip to enlarge while said electrosurgically cutting and surrounding or encapsulating a tissue volume, severing it from adjacent tissue. Following such electrosurgical cutting, the instrument and the captured tissue volume are removed through an incision of somewhat limited extent. Said electrosurgical cutting requires current flow from the cable to and through the surrounding tissue to maintain an electrical arc between the cables that is achieved by maintaining the cable at an elevated peak-to-peak voltage of at least 1000 volts relative to tissue. In order to enable current flow through the tissue, said elevated voltage must be applied at a alternative current frequency of at least 300 kHz in order to enable current flow from the cable through the surrounding tissue to a return electrode usually attached to the skin surface of the patient in the form of a pad having a surface area of at least 20 square inches. In this prior art, the voltage is maintained at a predetermined constant level (e.g., 1000 volts peak-to-peak), which the current flow from the cable and into the surrounding tissue is variable depending on the electrical resistivity of the surrounding tissue. The current flow from the cable into the surrounding tissue is higher for the case of denser, more fibrous tissue while the currently flow from the cable into the surrounding tissue is lower for the case of fatty tissue. Maintaining an adequate current flow into the surrounding tissue to sustain an arc and associated cutting effect requires a sufficiently high voltage to overcome the electrical impedance of adjacent tissue having a very high fat content (e.g., fatty breast tissue).

An improved design for the instrument described in U.S. Pat. No. 6,277,083 is described in U.S. Pat. No. 6,471,659 by Eggers, et al., entitled "Minimally Invasive Intact Recovery Of Tissue", issued Oct. 29, 2002. This instrumentation includes a tubular delivery cannula of minimum outer diameter, the tip of which is positioned in confronting adjacency with the target tissue volume to be removed. Such positioning is facilitated through the utilization of a forwardly disposed precursor electrosurgical electrode assembly. Located within the interior channel of this delivery cannula are five relatively elongate thin leaf members mutually interconnected at their base to define a pentagonal cross-sectional configuration. Each of the five leaf members terminates forwardly at a tip with a transversely bent eyelet structure. Slideably extending through each eyelet is a separate electrically conductive electrosurgical cutting and pursing cable, which extends to an attachment with the next adjacent leaf tip. The five separate cables extends rearwardly through five small guide tubes attached to each of the five separate leafs for connection with the slideable cable terminator component of a drive assembly. The drive assembly is driven forwardly by an electric motor through a translation assembly. By adjusting the location of a stop component, which engages the cable terminator component, the size of a captured specimen may be varied. For example, the device can be configured to recover tissue specimens of 10 mm, 15 mm, 20 mm or 25 mm effective maximum diametric extent. As the cable terminator component is pulled by the cable assembly into abutting engagement with the stop component, the cables are tensioned to draw the leaf eyelet structures together in a pursing action.

Cabling involved with the instrument specified in U.S. Pat. No. 6,471,659 must be quite diminutive in size while retaining adequate tensile strength in the temperature environment of an electrosurgical cutting arc. The electrosurgical arc temperature has been reported to be at least 1000 C. Heretofore, cable having a nominal diameter of 0.006 inch has been employed. While this electrosurgical cutting arc is present, the cables further must sustain not only stresses associated with the forward movement of the leafs but also those loads imposed by the capturing pursing activity during which the eyelets are drawn together to complete encapsulation of the tissue sample. For discussion of temperatures associated with electrosurgical arcs, see:

(8) Brown, B. H., et. al., "Medical Physics and Biomedical Engineering". Taylor & Francis Group, New York 1999: 238-239

(9) Woloszko, J., et. al., "Coblation in Otolaryngology". Proceedings of the SPIE 2003; 4949:341-352

The prior art methods other than excision using surgically sharp cutting blades (e.g., open surgery excision for biopsy or lumpectomy, ABBI method) utilize a cutting method known as electrosurgical tissue cutting (or often incorrectly referred to as "electrocautery" tissue cutting). For discussion of tissue cutting with electrosurgical arcs, see:

(10) Pearce, J. A., "Electrosurgery". John Wiley & Sons, New York 1986 (ISBN 0-471-85435-2); 67

In this modality of tissue cutting, a large electrical potential difference is imposed between the cutting member or active electrode (e.g., a flexible wire or multi-strand cable) and a passive or return electrode placed on the surface of the patient's body, typically a voltage difference in the range from 500 to 2000 volts peak-to-peak at a frequency ranging from 250 kHz to 5 MHz. This large potential difference allows the formation of electrical arcs between the cutting member and the adjacent tissue. At the point of impingement of the cutting arcs with the surrounding tissue, highly concentrated Joulean heating within the electrically conductive tissue occurs due to the very high current flux in the tissue at the point of impingement of the arcs with the tissue. This highly localized heating at the point of arc impingement causes the cellular fluid within the tissue cells to vaporize thereby fracturing the cellular walls and effecting the separation of the tissue along the advancing pathway of the electrosurgically induced electrical arcs.

In addition to the very high temperatures associated with the formation of electrical arcs during the process of electrosurgical cutting, which can lead to the failure of thin cutting wire or cable members, methods and apparatus which utilize electrosurgical cutting can also result in aberrant current flow in the tissue beyond the point of impingement by the arcs. As a consequence, electrical currents flowing from the active electrode (e.g., the flexible cutting wire or cable) to the passive electrode (e.g., the return electrode) placed on the surface of the patient's skin can induce unintended thermal damage to both the surrounding, un-excised tissue as well as the circumscribed tissue being excised for the purpose of diagnostic pathological evaluation. Furthermore, the electrical currents flowing from the active electrode (e.g., the flexible cutting wire or cable) to the passive electrode (e.g., the return electrode) placed on the surface of the patient's skin can cause unintended stimulation of nerve tissue beyond the zone of the applied localized anesthesia (e.g., by interstitial injection of agents such as Lidocaine) resulting in significant discomfort to the patient during the electrosurgical cutting procedure. For discussion of the potential for iatrogenic injury to the patient and damage to excised pathology specimens associated with the use with electrosurgery, see:

(11) Miller E., et. al., "Scalpel versus Electrocautery in Modified Radical Mastectomy". American Journal of Surgery 1988; 54:284-286 Mandrekas A. D., et. al., "Fat Necrosis Following Breast Reduction" Br. J. Plastic Surgery 1994; 47:560-562

(12) Rosen, P. P., "Breast Biopsy and Electrocautery" (Letter to the Editor) Annals of Surgery 1986; 204(5): 612-613

Also, in addition to the disadvantages described above related to the use of electrosurgery for the cutting and excision of breast tissue as described in U.S. Pat. Nos. 6,277,083 and 6,471,659, another limitation is related to the significant difference in the electrical resistivity of the tissue being cut. As described above, the process of electrosurgical cutting requires the flow of electrical current from the point of impingement of the electrosurgical arc to the return electrode placed on the surface of the patient's skin. However, for the case of excision of breast tissue as described in U.S. Pat. Nos. 6,277,083 and 6,471,659, the electrical resistance of the breast tissue can differ by a factor of almost ten fold as a result of the electrical properties inherent in regions of highly adipose breast tissue in contrast to very dense breast tissue. As a consequence, electrosurgical cutting may be inadequate in some patients with highly adipose breast tissue. For a discussion of the electrical resistivity or related properties of human tissue, see:

(14) Faes, T. J., et. al., "The Electrical Resistivity of Human Tissues (1oo Hz-10 MHz): A Meta-Analysis of Review Studies" Physiological Measurements 1999; 20(4):R1-R10

(15) Geddes, L. A., et. al., "The Specific Resistance of Biological Matter—A Compendium of Data for the Biomedical Engineer and Physiologist" Medical & Biological Engineering 1967; 5:271-293

An objective of the present disclosure is to enable minimally invasive excision of a defined volume of tissue while overcoming or greatly limiting the disadvantageous effects described above which are associated with electrosurgical tissue cutting and excision.

BRIEF SUMMARY

The present disclosure is addressed to apparatus, system and method for retrieving a tissue volume having an intact form utilizing minimally invasive surgical instrumentation. This instrumentation includes a tubular delivery cannula of minimum outer diameter, the tip or distal end of which is positioned in confronting adjacency with the target tumor or tissue volume to be removed. The tubular delivery cannula is disposed at the distal end of a disposable support housing that is inserted into the receiving cavity of a reusable housing or handle. Such positioning of delivery cannula is facilitated through the utilization of a forwardly disposed sharp cutting blade assembly. Located within the interior channel of this delivery cannula is a leaf member and tube assembly configured with a plurality of relatively elongate leaf members mutually supported at their base in a leaf and tube support member to define a polygonal cross-sectional configuration. Each of the leaf members terminates forwardly with an eyelet-containing tip. Also, each leaf member is covered by a thin, electrically insulative coating (e.g., Parylene N) capable of withstanding temperatures of up to at least 450 C in order to prevent unwanted electrical current flow between the leaf members during the application of electrical power.

Slideably extending through all of the plurality of leaf members is a small-diameter resistively heated portion of an electrically conductive cutting and pursing cable containing multiple strands (e.g., 7 to 19 strands) or a single-strand that extends from each of two small thermally and electrically conductive tube members, the leaf members supporting the wire or cable in the form of a complete circle. Hereinafter, the term "cable" will be most often used when referring to the small-diameter resistively heated portion of an electrically conductive cutting and pursing cable member although the member of the specified embodiments is not limited to a cable comprising multiple strands but may also comprise a single-strand wire. The two ends of the cable extend rearwardly through the two electrically and thermally conductive tube members attached to a leaf and tube support member and through channels in a drive assembly drive member for connection with the cable mounting hub. In addition to the plurality of leaf members and associated eyelets, a pair of electrically isolated, electrically and thermally conductive tube members serve as both cable conduits and electrodes through which extends, in a slideable manner, a small-diameter electrically conductive and resistively heated portion of electrically conductive cutting and pursing cable which continues through each eyelet of the plurality of leaf members. Alternatively, the small-diameter resistively heated portion of electrically conductive cutting and pursing cable containing multiple strands could be replaced by a small-diameter resistively heated portion of electrically conductive cutting and pursing wire containing only a single strand.

A tissue cutting and capture assembly comprises a plurality of leaf members, two electrically and thermally conductive tube members and the resistively heated portion of an electrically conductive cutting and pursing cable.

The leaf and tube support member is driven forwardly by a second motor-actuated drive tube drive member translation assembly that is abuttingly engaged against the leaf and tube support member to actuate the tissue cutting and capture assembly. The tissue cutting action is enabled by the passage of electrical current only through those portions of the resistively heated portion of electrically conductive cutting and pursing cable in direct contact with tissue. The electrical current passing through only those portions of the resistively heated portion of electrically conductive cutting and pursing cable in direct contact with tissue is of sufficient current flux to induce resistive heating of the pursing cable to achieve an elevated temperature sufficient to establish a thermally induced cutting effect at the leading edge of the resistively heated portion of electrically conductive cutting and pursing cable. An essential attribute of the apparatus of the present disclosure is the confinement of the path of electrical conduction of constant current required to achieve tissue cutting to only those portions of the deploying and retracting resistively heated portion of the electrically conductive cutting and pursing cable that are in direct contact with tissue. The confinement of the path of electrical conduction of constant current to only those portions of the deploying and retracting resistively heated portion of the electrically conductive cutting and pursing cable that are in direct contact with tissue avoids overheating the tensionable portions of the cutting and pursing that are located proximal to and not in contact with tissue since the rate of heat dissipation from the resistively heated cable is more than an order of magnitude less in the tensionable portions of the cutting an pursing cable not in contact with tissue.

The first and second tensionable portions of the cutting and pursing cable that are not in direct contact with tissue and proximal to the tip of the deployed tissue capture basket enable the application of the mechanical load or tension level required for the pursing down of the deployed tissue capture basket during the excision process. The first and second tensionable portions of the cutting and pursing cable that are not in direct contact with tissue and proximal to the tip of the tissue capture basket are not intended to support the electrical conduction of the constant current required to heat the cable above temperature threshold levels required for the thermal cutting of tissue. Importantly, electrical current flows only within the resistively heated portion of electrically conductive cutting and pursing cable in contact with tissue and no electrical current flows into or through the tissue being cut thereby minimizing necrosis of tissue beyond the immediate surface of the tissue incision as well as preventing the induction of pain in nerves more distant from the site of induced local anesthesia.

As the leaf member and tube assembly engaged with drive assembly drive member is driven forwardly by a second motor-actuated drive tube drive member translation assembly, the leaf members supporting the resistively heated portion of the electrically conductive cutting and pursing cable at the eyelets disposed at the distal tips of the leaf members are driven at an attack angle mutually outwardly through a guidance assembly to an extent that the cutting leading edge of the resistively heated portion of the electrically conductive cutting and pursing cable reaches an effective maximum diameter extending about the targeted tissue volume to be excised and captured. By way of example, drive assembly drive member may be drivably engaged with capture advance yoke by capture advancement ears extending from drive assembly drive member, said capture advance yoke being affixed to second motor-actuated drive tube drive member translation assembly.

At this maximum diameter juncture, the cable mounting hub encounters and is abuttingly engaged against a pre-positioned stationary first pursing actuation yoke member located on a first motor-actuated cable mounting hub translation assembly. Once cable mounting hub encounters and is abuttingly engaged against a pre-positioned first stationary pursing actuation yoke, the first motor-actuated cable mounting hub translation assembly retracts the cable mounting hub to increase the rate of pursing down of a deployed tissue capture basket as the second motor-actuated drive tube drive member translation assembly continues to drive the leaf member and tube assembly forward. The movements of first motor-actuated cable mounting hub translation assembly and second motor-actuated drive tube drive member translation assembly combine to actuate the retraction of the resistively heated portion of electrically conductive cutting and pursing cable causing the leaf members to purse down as the tissue cutting continues past the maximum diameter juncture. The combined movements of first motor-actuated cable mounting hub translation assembly and second motor-actuated drive tube drive member translation assembly enable the attainment of a preferred, nearly spherical shape of the distal end of captured tissue specimen. An actuator and control assembly comprises a cable terminator component or cable mounting hub coupled with the cable and a pursing actuation yoke.

In this pursing down phase of the tissue cutting and capture, the eyelet containing tip of each leaf member is drawn mutually inwardly to define a curvilinear profile to close the leading edge about the tissue volume as the forward movement of the leaf members continues. The resistively heated portion of the electrically conductive cutting and pursing cable, now under tension and constrained at the outer surfaces of the leaf members, contributes to the structural stability of the resultant deployed tissue capture basket. Adjustment of the speed of translation of the first motor-actuated cable mounting hub translation assembly that is abuttingly engaged against the cable mounting hub establishes the rate of closure of the deployed tissue capture basket as well as the degree or extent of curvature of the noted curvilinear profile. Following incision and capture of the targeted tissue volume, the voltage applied across the first and second electrically and thermally conductive tubes and the associated electrical constant current flowing through the resistively heated portion of the electrically conductive cutting and pursing cable that is in direct contact with tissue is discontinued. Also, the voltage applied to the second motor-actuated drive tube drive member translation assembly and the voltage applied to the first motor-actuated cable mounting hub translation assembly are both discontinued. At this point, the delivery cannula is removed from adjacent tissue along with the retained volume of captured tissue containing the targeted tissue volume.

By employing this noted first motor-actuated cable mounting hub translation assembly and pursing actuation yoke at a practitioner selected spacing within the disposable support housing, the instrument enjoys the capability of providing an important range of leaf member and tube assembly leading edge maximum effective diameters during tissue incision and capture. Accordingly, the maximum effective diameter can be selected by the practitioner just prior to the start of a procedure using provided capture diameter selector buttons. The relatively straightforward structuring of the delivery cannula, leaf member and tube assembly and drive assembly drive member permits their fabrication as a discrete disposable component, removably insertable within a hand maneuvered housing assembly.

The first motor-actuated cable mounting hub translation assembly and second motor-actuated drive tube drive member translation assembly may be arranged in-line along the same longitudinal axis or may be arranged side-by-side within the housing assembly.

Practitioner control over the instrument may be provided in the form of a footpedal assembly or control switch located on the hand-held housing assembly. In a first embodiment, the externally located control assembly is connected to a housing assembly by a multi-lead cable and the remotely located control assembly is connected to a footpedal assembly by a footpedal cable. In a second embodiment, all functions incorporated within the control assembly are incorporated within housing assembly in combination with a rechargeable battery, thereby eliminating the need for an external control assembly. The second embodiment is also referred to hereinafter as a housing assembly with internal control assembly and rechargeable battery.

In carrying out the retrieval procedure, following preliminary self-checks for proper instrument and optional vacuum system connections and transfer assembly positioning, the distal end of the delivery cannula is positioned in confronting adjacency with the targeted tissue volume to be removed. The positioning step is achieved through the utilization of a forwardly disposed sharp cutting blade assembly and guided using stereotactic, ultrasound, MRI or other guidance methods suitable for locating the targeted tissue volume.

The delivery cannula being thus positioned, the practitioner depresses the footswitch or depresses the capture button located on housing assembly to commence the incision and capture of the targeted tissue volume. Upon depressing and continuing to depress the capture footswitch or capture button, the external control assembly or internal control assembly enters a capture mode. At the commencement of this capture mode, electrical current is applied exclusively through the resistively heated portion of electrically conductive cutting and pursing cable or wire via first and second electrically and thermally conductive tubes or conduits, preferably at a constant level, from the current source and in conjunction with the activation of the first motor-actuated cable mounting hub translation assembly and second motor-actuated drive tube drive member translation assembly. The current source preferably operates in a direct current (i.e., DC) mode. In addition, the current source preferably delivers a substantially constant current level to the resistively heated portion of electrically conductive cutting and pursing cable. Alternatively, the current source preferably delivers a substantially constant current level as alternating current at an elevated frequency (e.g., 50 to 100 kHz) to minimize the occurrence of electrical stimulation of tissue in contact with the resistively heated portion of electrically conductive cutting and capture cable or wire. However, unlike prior art devices, no electrical current flows through surrounding tissue but only flows through the exposed portions of the resistively heated portion of electrically conductive cutting and pursing cable or wire.

With the simultaneous commencement of the second motor-actuated drive tube drive member translation assembly and the delivery of a constant current to the resistively heated portion of electrically conductive cutting and pursing cable or wire, the leaf members and the first and second electrically and thermally conductive tubes commence to be deployed from the guidance assembly. A tissue cutting and capture assembly comprises a plurality of leaf members, two electrically and thermally conductive tube members and the resistively heated portion of an electrically conductive cutting and pursing cable. During the ensuing advancement of the resistively heated portion of electrically conductive cutting and pursing cable supported by the leaf member and tube assembly, induced by the second motor-actuated drive tube drive member translation assembly, and the pursing down of the tissue cutting and capture assembly induced by the first motor-actuated cable mounting hub assembly, the electrical current levels delivered to first and second motors are continuously monitored.

When the level of electrical current delivered to the first or second motors increases above a predetermined level, it indicates that the pursing down of the leaf members and the rigid tube members has been completed thereby commencing the "capture complete" state. In this capture complete state, the electrical current applied to the cutting and capture cable or wire is discontinued. Also, the voltage applied to the second motor-actuated drive tube drive member translation assembly is discontinued and the voltage applied to the first motor-actuated cable mounting hub assembly is discontinued.

The delivery cannula with captured tissue specimen is next removed from the incision site of the subject. The release of the captured tissue specimen containing the targeted tissue volume from the enveloping tissue cutting and capture assembly formed by the leaf members and the first and second electrically and thermally conductive tubes may be activated by the operator by depressing the "release tissue" switch on the front panel of the control assembly or controller. Once the release tissue switch is depressed, the motor rotational direction of the second motor-actuated drive tube drive member translation assembly is reversed causing the leaf members and the first and second electrically and thermally conductive tubes to be partially withdrawn into the delivery cannula. The retraction of the drive member to a position causes the leaf members of the leaf member and tube assembly and associated pursing cable assembly to assume an open cup formation permitting facile access to the recovered tissue specimen. Alternatively, the practitioner may use a conventional cutting instrument such as scissors to cut the pursing cable at one of its exposed locations at the distal end of the leaf member and tube assembly thereby causing the leaf members to open, permitting facile access to the recovered tissue specimen.

If, during the capture mode, the practitioner wishes to halt the procedure, the capture footswitch or capture button is released to cause the control assembly to enter a pause mode. In this pause mode, the current applied to the resistively heated portion of electrically conductive cutting and pursing cable as well as the voltage applied to the second motor-actuated drive tube drive member translation assembly are suspended and the voltage, if being applied to the first motor-actuated cable mounting hub and pursing actuation yoke stop member assembly, is suspended. The practitioner carries out return to the capture mode performance by again depressing the capture footswitch or capture button.

The current source is preferably configured to deliver a constant current level to the resistively heated portion of electrically conductive cutting and pursing cable or wire. A terminal assembly comprising first and second electrical contacts is provided in the disposable housing assembly in order to provide for connection to the current source at corresponding first and second electrical terminals in the housing assembly. In addition, during the ensuing actuation of the leaf member and tube assembly by the second motor-actuated drive tube drive member translation assembly and ensuing actuation of the first motor-actuated cable mounting hub assembly, the mechanical load characteristics of the motor are monitored by monitoring the current level delivered to first and second motors to enable monitoring of both motor performance and for detecting the completion of capture. In the latter regard, a forward stall condition is detected to determine capture completion commencing a capture complete state. A control system includes both a current source, first and second motor drive power sources, first and second motor current measurement circuits, an optional pursing cable resistance measuring circuit and programmed microcomputer to enable response to capture actuation switch disposed on the foot pedal, audible tones and activation display indicator lights and stop procedure when capture complete state is attained.

In addition to the control system, an optional vacuum system enables the aspiration, if needed, of any generated smoke or liquids issuing from the site of tissue excision via a flexible conduction conduit positioned between the tissue retrieval instrument and the vacuum system. The vacuum system may be an electrically powered smoke evacuator device or may be a bellows-type evacuation drain.

Other objects of the present disclosure will be obvious and will, in part, appear hereinafter. The present disclosure, accordingly, comprises the method, system and apparatus possessing the construction, combination of elements, arrangement of parts and steps, which are exemplified in the following detailed description. For a fuller understanding of the nature and objects of the present disclosure, reference should be made to the following detailed description taken in connection with the accompanying drawings.

BRIEF DESCRIPTION OF THE DRAWINGS

FIG. 4 is a partial sectional view of the instrument shown in FIG. 1 with portions broken away;

FIG. 6 is a side view of disposable tissue capture device seen in FIG. 2;

FIG. 7 is a bottom view of disposable tissue capture device seen in FIG. 2;

FIG. 8 is a sectional view of side of disposable tissue capture device seen in

FIG. 2;

FIG. 8A is a detailed sectional view of top at proximal end of disposable tissue capture device seen in FIG. 2;

FIG. 9 is a detailed sectional view of cable mounting hub seen in FIG. 8;

FIG. 10 is a sectional view taken through the plane 10-10 shown in FIG. 8;

FIG. 11 is a sectional view taken through the plane 11-11 shown in FIG. 8;

FIG. 12 is a partial sectional view of distal end of disposable tissue capture device seen in FIG. 2;

FIG. 13 is a perspective and exploded view of tip of disposable tissue capture device seen in FIG. 2;

FIG. 14 is a perspective view of blade seen in FIGS. 12 and 13;

FIG. 15 is an end sectional view of tip region of disposable tissue capture device seen in FIG. 2;

FIG. 15A is a detailed end sectional view of electrically and thermally conducting tube seen in FIG. 15;

FIG. 15B is a detailed partial side sectional view of electrically and thermally conducting tube seen in FIG. 15;

FIG. 15C is an end sectional view of tip region of alternative disposable tissue capture device seen in FIG. 2 comprising five leaf members;

FIG. 16 is a partial plan view of a leaf employed with the structure shown in FIG. 20 as it appears prior to the bending of its tip portion;

FIG. 17 is a partial view of the leaf shown in FIG. 16 with its tip bent into an operative orientation;

FIGS. 25A-25F combine, as labeled thereon, to provide a flow chart describing the methodology of the invention.

DETAILED DESCRIPTION

Figure 1:
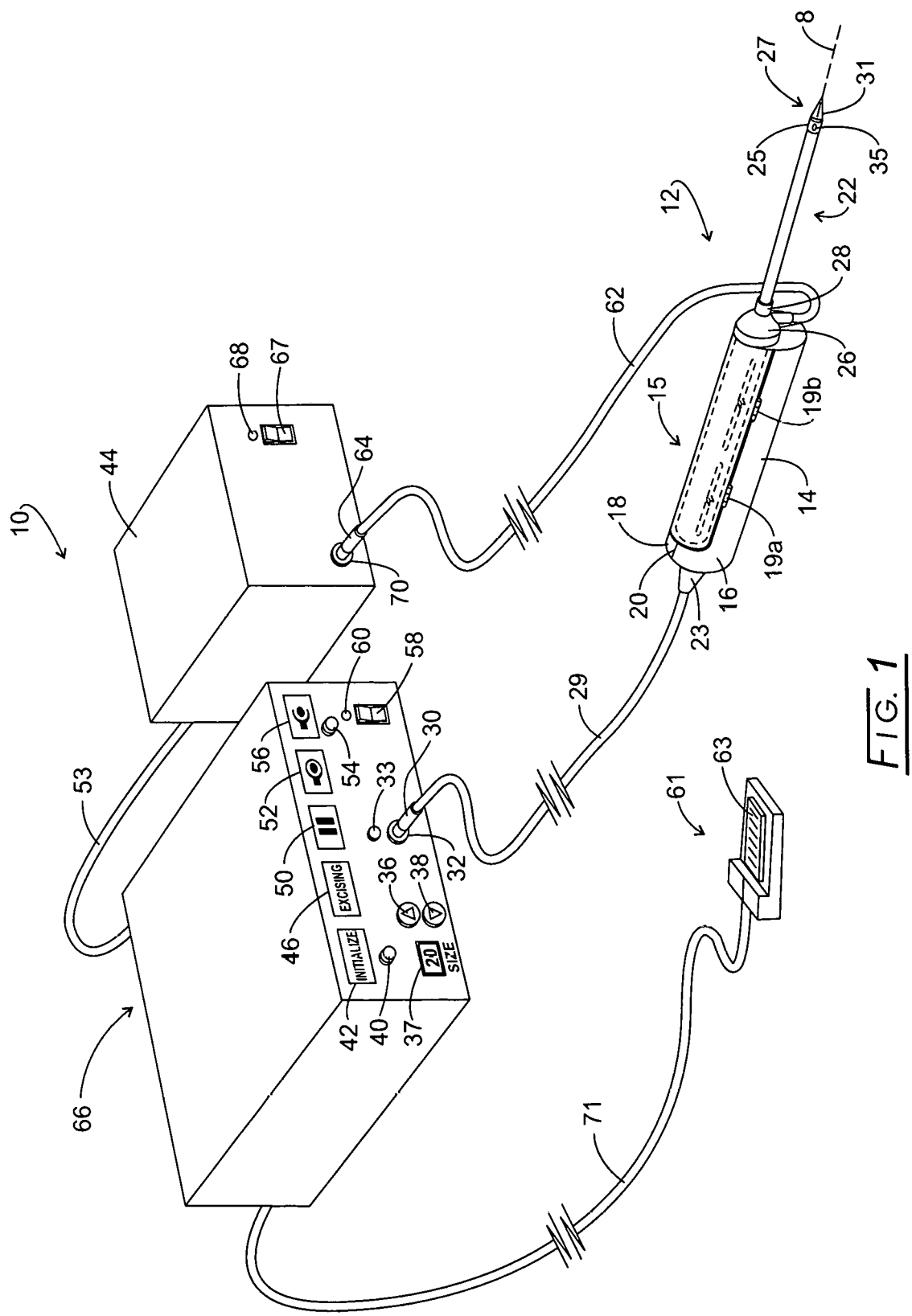
FIG. 1 is a perspective view of the system of the invention showing a hand held instrument, control assembly, footswitches and a vacuum system component.

A predominate characteristic of the present disclosure resides in the employment of a leaf member and tube assembly in conjunction with a delivery cannula. This leaf member and tube assembly is configured with a forward portion, which extends to a forwardly disposed cutting leading edge, which incorporates a mechanically sharp cutting blade. Targeted tumor or tissue along with adjacent healthy tissue is circumscribed or encapsulated by this leaf member and tube assembly through the utilization of a resistively heated portion of electrically conductive cutting and pursing cable extending along the distal tip of the leaf member and tube assembly which provides (a) the thermal cutting effect by virtue of being resistively heated and maintained at a temperature sufficient to effect thermal cutting of tissue and (b) constricts the leading edge to, in effect, encapsulate the incised tissue volume defined by the emerging and outwardly expanding tips of the leaf members followed by their inwardly contracting tips during the pursing down phase of the tissue capture process. In a preferred embodiment, the leaf member and tube assembly is implemented with the combination of (a) at least four elongate flexible metal leaf members the tips of which are formed with an eyelet for receiving a single cable of the noted resistively heated portion of electrically conductive cutting and pursing cable assembly and (b) two electrically isolated, thermally and electrically conductive rigid tubes which serve as both conduits and electrodes for the noted resistively heated portion of electrically conductive cutting and pursing cable. By selecting a component orientation establishing where a pursing or constricting action commences, the maximum leading edge periphery for capture may be elected and, typically, may range, for example, from about a 10 mm to about a 40 mm effective diametric extent. Initial positioning of the delivery cannula tip in confronting adjacency with a tissue volume is facilitated through the utilization of a surgically sharp cutting blade assembly located at the tip. Following appropriate positioning of the tip, a second motor-actuated drive tube drive member translation assembly is enabled to actuate the leaf member and tube assembly thus providing an optimized rate of movement of the leading edge of the resistively heated portion of electrically conductive cutting and pursing cable about the targeted tissue volume. A desirable feature of the system of the present disclosure resides in the incorporation of the delivery cannula and cable-implemented leaf member and tube assembly within a disposable support housing. That disposable support housing is removably mounted within a reusable housing assembly or handle containing second motor-actuated drive tube drive member translation assembly and first motor-actuated cable mounting hub translation assembly and control components. A pursing actuation yoke attached to first motor-actuated cable mounting hub translation assembly functions as a stop. The term "cannula" or "delivery cannula" as used herein is intended to refer to any elongate surgical delivery structure, rigid or flexible, having a capability for deploying resistively heated portion of electrically conductive cutting and pursing cable.

Referring to FIG. 1, a system according to the present disclosure is represented in general at 10. System 10 includes a tissue retrieval instrument or apparatus represented generally at 12, which includes a polymeric housing assembly represented generally at 15. Housing assembly 15 comprises a re-useable housing 14 and a disposable support housing (seen at 100 in FIG. 2). Reusable housing 14 is formed of two molded components shown as housing right side 16 and a housing left side 18. Sides 16 and 18 extend mutually outwardly from a medial plane represented at a joint line 20. An elongate delivery cannula represented at 22 is shown supported from the forward portion of the reusable housing 14, which extends along a longitudinal axis 8. A distal end of the delivery cannula extends through a suction manifold 26, which is retained in position by a collar 28. The forward region of the cannula 22, as represented at 27 extends to a distal end or tip 25. Distal end or tip 25 also supports a surgically sharp blade 31, which enables the initial advancement positioning of the distal end of tip 25 of cannula 22 in a confronting relationship with respect to the targeted tissue site. A flexible suction conduit providing a body fluid, smoke and steam evacuation function is shown at 62 extending from the suction manifold 26 to the input housing 70 of a vacuum system 44. Vacuum system 44 may be activated by a control assembly-mounted switch 67 or, optionally, from a foot pedal switch (not shown). Smoke and steam evacuation from the distal end 25 is called for to avoid thermal injury to tissue due to a migration of steam back along the exterior surface of delivery cannula 22. The vacuum system 44 seen in FIG. 1 may be an electrically powered smoke evacuator (e.g., Stackhouse Smoke Evacuator, Ecolab, Inc., St. Paul, Minn.). Alternatively, the vacuum system may be a non-powered, bellows-type evacuation drain (e.g., Polyvac Set, Polymed Medical Devices, Okhla Industrial Estate, New Delhi, India).

Still referring to FIG. 1, footpedal assembly 61 will be seen to function as a start tissue capture switch, which is actuatable by depressing footswitch 63. An illuminated "Excision" display 42 on front panel of control assembly 66 as well as an audible tone provide visual and audible cues to operator during the excision and capture of the targeted tissue. Energization and control is provided to the tissue incision and retrieval instrument 12 via a multi-lead cable 29 (e.g., a 10 foot or 3 meter cable), which connects with a control assembly and current source control assembly or controller represented generally at 66. Connection is shown through a multi-lead connector 30 at the end of multi-lead cable 29, which is coupled to a housing connector 32.

Still referring to FIG. 1, proper connection of the multi-lead cable 29 and multi-lead connector 30 with the controller receptacle 32 of the control assembly 66 is indicated by an illuminated green LED 33 positioned above controller receptacle 32. This connection test is carried out by directing current to a coding resistor (e.g., 10,000 Ohms) within housing assembly 15. Thus, the controller checks to confirm that the coding resistor is present in the housing assembly 15 to confirm that the housing assembly 15 is properly connected to the controller receptacle 32 via multi-lead connector 30. To the right of multi-lead connector 30 is an on/off power input switch 58. When switch 58 is in an "On" orientation, a green LED 60 is energized. A footpedal assembly 61 is coupled via a cable 71 to the rear panel of the control assembly 66. Footswitch 63 of this footswitch activates the resistively heated portion of electrically conductive cutting and pursing cable 309 during a tissue excision and capture procedure, the practitioner being required to depress footswitch 63 throughout that procedure in order to enable the capture activity to proceed. Release of either footswitch 63 during the capture procedure will cause the system to enter a pause mode as indicated by illuminated pause icon 50 on front panel of control assembly 66.

Visual cuing is provided at the control assembly 64. In this regard, an "Initialize" switch 40 is operationally associated with an "Initialize" display 42, which illuminates in a green color upon actuation of that switch. A yellow tissue capture mode visual cue labeled "Excising" is shown at 46 on front panel of control assembly 66 represents an energization of the noted resistively heated portion of electrically conductive cutting and pursing cable 309 is activated and sustained while depressing footswitch 63. This yellow tissue capture mode visual cue is activated during the resistively heated portion of electrically conductive cutting and pursing cable 309 advancement through the delivery cannula tip 25 and during its circumscribing pathway around the targeted tissue volume to complete the tissue capture. Upon the completion of such tissue capture, a "capture complete" mode visual cue is provided by illumination of a capture complete icon 52 located at front panel of control assembly 66. A speaker located at the rear of control assembly 66 provides aural cues. In general, a continuous tone is provided wherever resistively heated thermal cutting is taking place. A pulsed tone occurs in the event of a pause in the capture procedure. Because of the above-noted opportunity for steam migration, it is preferred that system 10 provides an assurance that the vacuum system 44 be actuated. Preferably, the control assembly of control assembly 64 functions to permit commencement of the procedure only upon a turning on of vacuum system 44. Such a monitoring of vacuum system 44 is accomplished with a vacuum sensor (not shown) within vacuum system 44. The monitoring of vacuum sensor output to control assembly 66 is represented at vacuum monitor cable 53.

Figure 2:
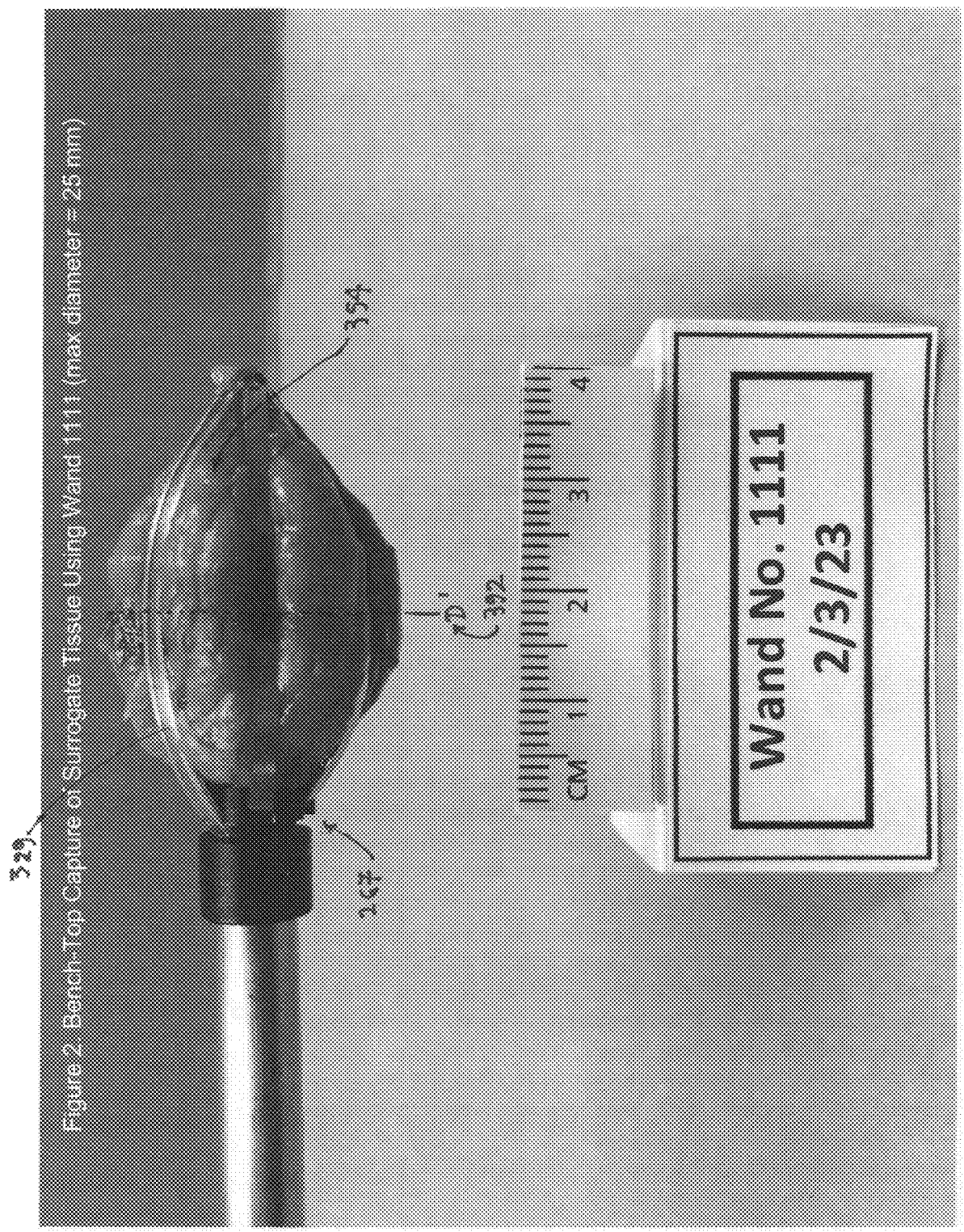
FIG. 2 is a perspective view of the instrument shown in FIG. 1 with a disposable component being shown removed from a reusable housing.

Referring to FIGS. 1 and 2, the disposable component indicated generally at 100, of tissue incision and retrieval instrument 12 is revealed in an orientation prior to insertion within the reusable housing assembly 15. As seen in FIG. 2, delivery cannula 22 is seen extending forwardly from a cylindrically shaped disposable support housing 100. The forward region of support housing 100 supports the suction manifold 26. In this regard, it may be observed that suction manifold 26 is configured with an external groove and keyway slot that engages with and is secured by distal end of reusable housing 14 (not shown in FIG. 2 but seen in FIG. 4).

Figure 20:
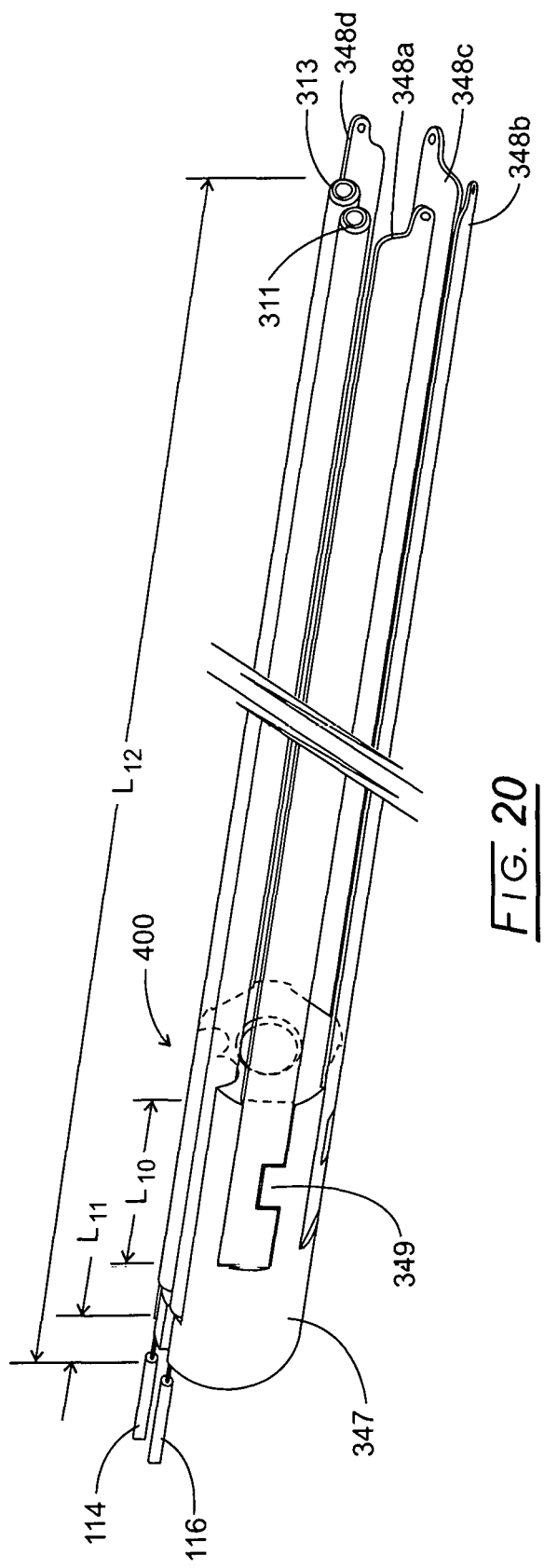
FIG. 20 is an assembly view of leaf and tube support member, leaf members and electrically and thermally conductive tubes as seen in FIG. 21.

Still referring to FIG. 2, positioned at the proximal end of support housing 100 are two spaced apart first and second electrical contacts 120 and 122 (not shown but 30 seen in FIG. 8A) which are oriented to make contact with corresponding first and second electrical terminals 186 and 188 disposed within reusable housing 14 upon insertion of disposable support housing 100 within the receiving cavity 166. Electrical contacts 120 and 122 serve as two electrical poles or electrodes that selectively receive a controlled constant current, preferably D.C. mode current, which is applied respectively to the resistively heated portion of electrically conductive cutting and pursing cable 309 through sliding electrical contact with first and second electrically and thermally conductive rigid tubes 311 and 313 associated with the leaf member and tube assembly 400 as seen in FIG. 20, in which resistively heated portion of electrically conductive cutting and pursing cable 309 that normally extends from first electrically and thermally conductive rigid tube 311 through the eyelet 327 of each leaf member 348 and continuing to second electrically and thermally conductive rigid tube 313 is not shown. The two ends of load bearing as well as resistively heated portion of electrically conductive cutting and pursing cable 309 are attached to cable mounting hub 296 (seen in FIG. 8), as described in greater detail below. The load-bearing as well as resistively heated portion of electrically conductive cutting and pursing cable 309 extend rearwardly to cable mounting hub 296 having first and second pursing actuation ears 124 and 128 slideably mounted within an elongate stabilizer slot 126 arranged in parallel with axis 8. A corresponding elongate stabilizer slot is found in the opposite side of the support housing 100. Located forwardly of the slots as at 126 are two additional elongate drive slots, one of which is shown at 130 similarly arranged in parallel with axis 8. The outwardly extending first and second capture advancement ears 134 and 136 of drive assembly drive member 324 extend from third and fourth elongate stabilizer slots 130 and 131, respectively. These first and second capture advancement ears 134 and 136 support rearwardly disposed capture advance yoke 185 whose driven surface is used to impart forward movement to the drive assembly drive member 324 functioning, in turn, to deploy the leaf member and tube assembly 400 from delivery cannula 22. When the support housing 100 is installed within the top surface facing receiving cavity or region 166 of reusable housing 14 shown generally at 12, these first and second capture advancement ears 134 and 136 pass through oppositely disposed notches in drive assembly drive member 324. Note, that the forward portion of reusable housing 14 also is provided with alignment key tab 165 at the distal end of its receiving cavity 166. The axis of that receiving region is coincident with instrument axis 8. The figure also reveals that the axis of cannula 22 is coincident with instrument axis 8. Accordingly, when the support housing 100 is inserted into the receiving cavity of reusable housing 14 and alignment key tab 165 is inserted into receiving alignment key notch 167 at distal end of disposable housing, hinged cover 13 of reusable housing is closed and secured with latch 11 to maintain position of disposable support housing 100 within reusable housing 14 during tissue excision and capture procedure.

Figure 3:
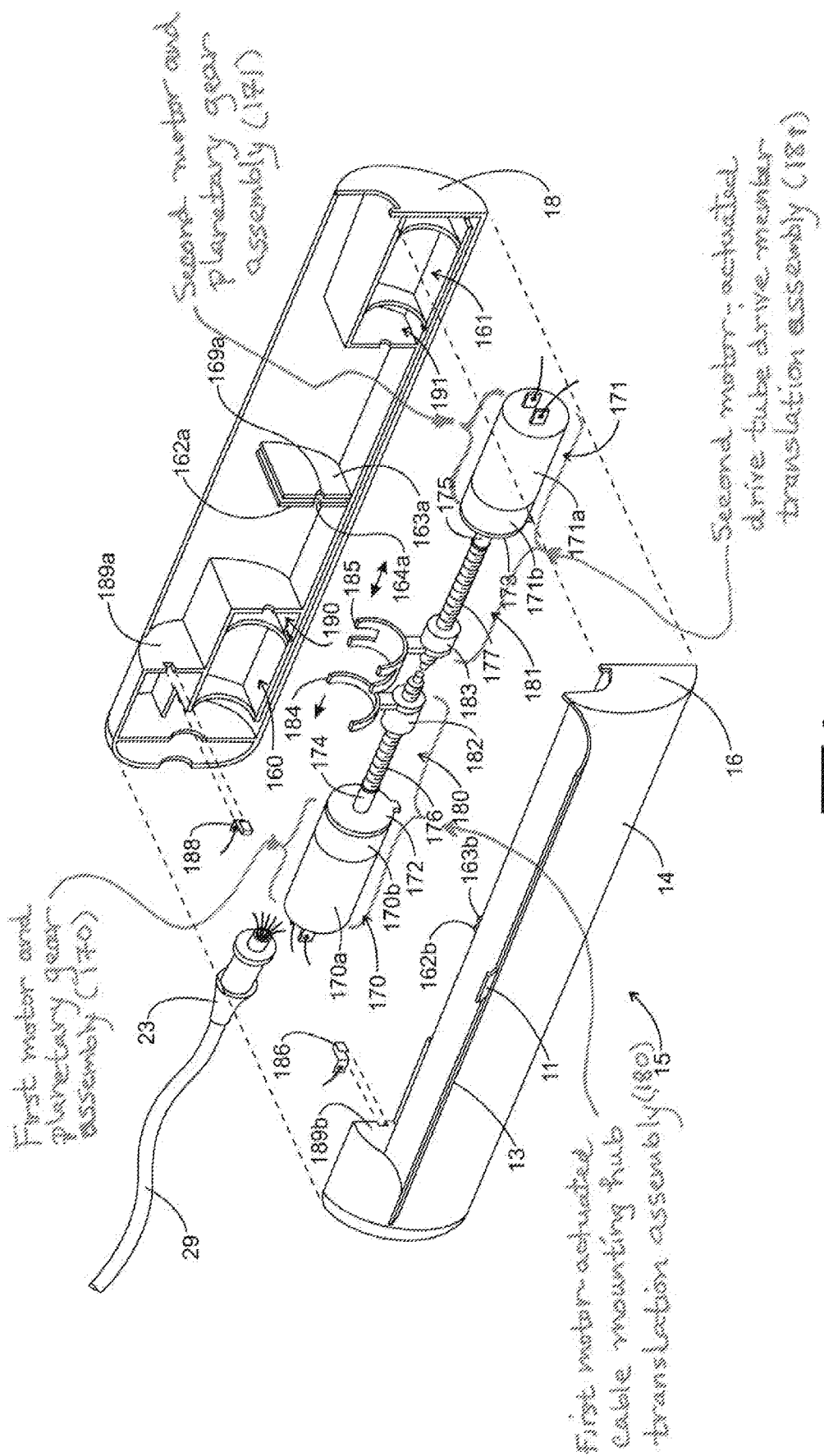
FIG. 3 is an exploded view of the reusable housing shown in FIG. 2.

Referring to FIG. 3, the assembly of the reusable components of the tissue incision and retrieval instrument 12 is revealed in exploded fashion. As seen in FIG. 3, the exterior surface of the right side 16 of reusable housing 14 is revealed and the corresponding interior of left housing 18 is revealed. These two sides are symmetrical except for the features related to hinged cover 11. Each of the housing sides 16 and 18 is formed with one half of first and second motor mount chambers as shown at 160 and 161 in connection with housing side 18. Positioned just forwardly of the chamber 160 are first and second bulkheads 162 and 163 defining first and second circular openings 164 and 169 to support distal ends of rotatable lead screws 176 and 177. The left halves of circular openings 164a and 169a are seen in FIG. 3. A forward region of each housing side is configured with one half of a circular opening to serve as a thrust bearing as represented at 164 and 169 in connection with housing side 18.

Still referring to FIG. 3, positioned within first motor mount chamber 160 is a first motor and planetary gear assembly represented generally at 170, which incorporates a first motor component 170a in combination with a first planetary gear assembly 170b. First motor and planetary gear assembly 170 is relatively loosely positioned within chamber 160 to the extent that it has limited freedom of movement with the exception of rotational movement. In this regard, a torque stop component 172 prohibiting overall motor assembly rotation is coupled to the forward or output end of first motor and planetary gear assembly 170. Also, positioned within second motor mount chamber 161 is a second motor and planetary gear assembly represented generally at 171, which incorporates a motor component 171a in combination with a planetary gear assembly 171b. Second motor and planetary gear assembly 171 is relatively loosely positioned within chamber 161 to the extent that it has limited freedom of movement with the exception of rotational movement. In this regard, a torque stop component 173 prohibiting overall motor assembly rotation is coupled to the forward or output end of the second motor and planetary gear assembly 171.

Referring to FIGS. 3 and 4, the mechanical output from first and second motor and planetary gear assemblies 170 and 171 is connected through first and second metallic flexible bellows-shaped couplers 174 and 175 extending through third and fourth bulkheads 178 and 179 to connection with lead screws 176 and 177 implemented with the threaded elongate rods of a translation nut mechanism arranged in parallel with the longitudinal axis 8 of the apparatus 12. The first and second metallic flexible bellows-shaped couplers bellows 174 and 175 provides a torsionally rigid, but axially flexible coupling reducing the vagaries of elongate mechanical-rotational force transmission. By way of example, bellows couplers as at 174 and 175 are marketed under a model designation SC-3 by Servometer Corp. of Cedar Grove, N.J. Alternatively, other flexible coupling components may be used for this purpose including a helical beam coupler marketed by Helical Products Company, Santa Maria, Calif. By way of example, lead screws as at 176 and 177 are marketed under the designation lead by Thomson of Radford, Va.

Still referring to FIG. 3, rotatably driven from a first motor and planetary gear assembly 170 through a first bellows-shaped coupler 174, the distal end of first lead screw 176 is supported and rotatable within first circular opening 164 formed by semicircular openings 164a and 164b located in first bulkheads 162a and 162b, respectively. With this arrangement, a freedom of rotational movement is provided for the entire assembly proximal to first circular opening 164 including first motor and planetary gear assembly 170, first bellows-shaped coupler 174 and first lead screw 176 permitting the first motor and planetary gear assembly 170 to be mounted in self aligning confinement within the first motor mount chamber housing 160. Thus, binding or like phenomena are avoided in connection with the motor drive actuator system. The first lead screw 176 is threadably engaged with a first motor-actuated cable mounting hub translation assembly represented generally at 180 which comprises a translation nut component and a generally Y-shaped pursing actuation yoke 184 which is configured to extend to a position spaced from but aligned for driven engagement with the first and second pursing actuation ears 124 and 128 (as seen in FIG. 2) when the support housing 100 is initially inserted in the receiving cavity 166. By way of example, first translation nut component as at 182 is marketed under the designations translation nut, ball nut and Supernut by Thomson Linear of Radford, Va.

Still referring to FIG. 3, rotatably driven from a second motor and planetary gear assembly 171 through a second bellows-shaped coupler 175, the distal end of second lead screw 177 is supported and rotatable within second circular opening 169 formed by semicircular openings 169a and 169b located in second bulkheads 163a and 163b, respectively. With this arrangement, a freedom of rotational movement is provided for the entire assembly proximal to second circular opening 169 including second motor and planetary gear assembly 171, second bellows-shaped coupler 175 and second lead screw 177 permitting the second motor and planetary gear assembly 171 to be mounted in self aligning confinement within the second motor mount chamber housing 161. Thus, binding or like phenomena are avoided in connection with the motor drive actuator system. The second lead screw 177 is threadably engaged with a second motor-actuated drive tube drive member translation assembly represented generally at 181 which comprises a second translation nut component 183 and a generally Y-shaped capture advancement yoke 185 which is configured to extend to a position spaced from but aligned for driven engagement with the first and second capture advancement ears 134 and 136 (as seen in FIG. 2) when the support housing 100 is initially inserted in the receiving cavity 166. By way of example, second translation nut as at 183 is marketed under the designation translation nut by Thomson of Radford, Va.

Still referring to FIG. 3, mounted upon the first and second wall portions 189a and 189b at the proximal end of receiving cavity 166 are two electrical terminals 186 and 188 which are retained in place by a polymeric adhesive and which function to supply cutting current to the two contact surfaces of first and second electrical contacts 120 and 122 (as seen in FIG. 7) located on the disposable support housing 100.

Finally, FIG. 3 shows an input assembly for the cable 29. This is a molded plastic cable strain relief 23, which functions to introduce multi-lead cable 29 into the reusable housing 14 and to provide stress relief for the cable 29.

Referring to FIG. 4, a sectional view is presented illustrating the operative association of the motor drive features with the disposable support housing 100 contained components. As seen in FIG. 4, a first motor and planetary gear assembly 170 is seen to be located within first motor mount chamber 160. As noted above, within first motor mount chamber 160, the first motor and planetary gear assembly 170 is permitted some self-aligning movement but is restrained from rotational movement by first torque stop component 172. The output from the first planetary gear assembly 170b is coupled to the driven input side of first bellows-shaped coupler 174 which is seen to extend through first coupler cavity 190 defined by oppositely disposed and spaced apart third bulkhead 178. The elongate threaded lead screw 176 is seen extending to first circular opening 164 in first bulkhead 162. First bulkhead 162 and associated first circular opening 164 provide support against all of the driving forces imposed from the first motor and planetary gear assembly 170 as it drives the first translation nut 182 along the length of the first lead screw 176. The figure reveals that the driving surfaces 226 of the Y-shaped yoke 184 engage the first and second pursing actuation ears 124 and 128 to urge and drive a cable mounting hub 296 backwardly as is described in connection with FIG. 23.

Still referring to FIGS. 3 and 4, a second motor and planetary gear assembly 171 is seen to be located within second motor mount chamber 161. As noted above, within second motor mount chamber 161, the second motor and planetary gear assembly 171 is permitted some self-aligning movement but is restrained from rotational movement by second torque stop component 173. The output from the second planetary gear assembly 171b is coupled to the driven input side of second bellows-shaped coupler 175 which is seen to extend through first coupler cavity 191 defined by oppositely disposed and spaced apart fourth bulkhead 179. The elongate second threaded lead screw 177 is seen extending to second circular opening 169 in second bulkhead 163. Second bulkhead 163 and associated first circular opening 169 provide support against all of the driving forces imposed from the second motor and planetary gear assembly 171 as it drives the second translation nut 183 along the length of the second lead screw 177. The figure reveals that first and second driving surfaces 227a and 227b located on the interior surfaces of slot 229 of the Y-shaped yoke 185 engage the first and second capture advancement ears 134 and 136 to urge and drive assembly drive member 324 forwardly as is described in connection with FIGS. 22 and 23.

In addition, FIG. 4 also reveals some details of the forward region 27 of delivery cannula 22. The forward region 27 is depicted as it is utilized for relatively smaller tissue volumes, for example, encompassed within a diametric extent of about 30 mm. The tip incorporates a surgically sharp blade 31 positioned with the blade tip coincident with longitudinal axis 8. Located at forward region 27 are, by way of example, five smoke/steam collection or suction intake ports, two of which are represented at 35a and 35b. By way of example, the edges of suction intake ports 35 may be positioned about 0.2 inch from blade support 230 and have a diameter of about 0.08 inch.

Figure 4A:
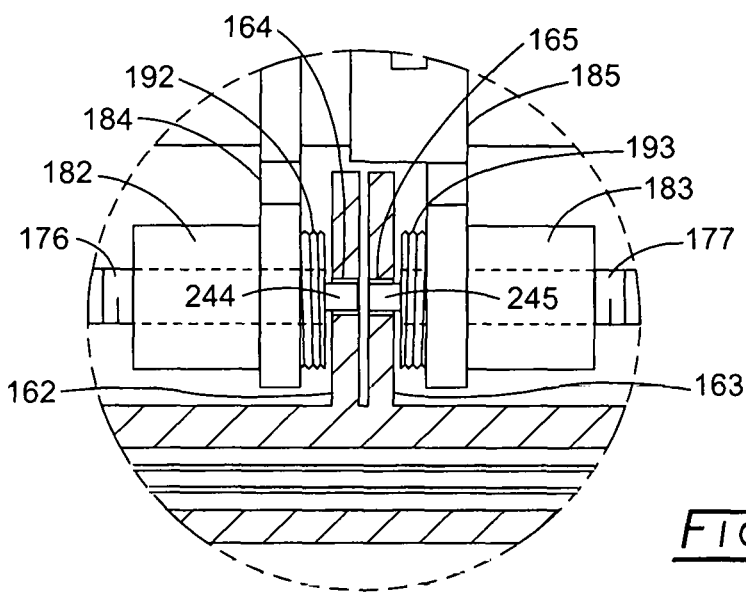
FIG. 4A is a detailed sectional view of portion of ends of transfer assemblies seen in FIG. 4.

Referring to FIGS. 4 and 4A, the actuator and transfer assemblies, which are mounted within the reusable housing 14 are more clearly depicted wherein first motor and planetary gear assembly 170 is seen to be comprised of a first D.C. motor 170a having, by way of example, a 3.2 watt assigned power rating marketed under the catalog designation 118686 by Maxon Precision Motors Inc., of Burlingame, Calif. This first motor 170a is combined with a first planetary gear 170b exhibiting, by way of example, a 29:1 reduction and marketed under the catalog designation 118185 by Maxon Precision Motors Inc. (supra). The output shaft of the first planetary gear 170b is shown at 232 and is seen to extend through the first torque stop component 172. First torque stop component 172 is bolted to the forward casing of first planetary gear 170b and is configured with a first rectangular tab portion 234 which engages a first torque stop slot 236 within reusable housing 14. Motor assembly first output drive shaft 232 is fixed by a setscrew into driving relationship with one end of the first bellows-shaped coupler 174. The opposite end of first bellows-shaped coupler 174 is connected to the first proximal circular necked-down shaft 240 of first lead screw 176. Fixed connection with first lead screw 176 is provided by another setscrew extending within first bellows-shaped coupler 174. The distal end of the first lead screw 176 is a first distal circular necked-down shaft portion 244 is supported by first circular opening 164 in first bulkhead 162 and is rotatable therein. First translation nut component 182 (e.g., Model No. PRM0601 supplied by Thomson, Radford, Va.) of first motor-actuated cable mounting hub translation assembly 180 is shown threadingly engaged with first lead screw 176.

As seen in FIGS. 2, 3 and 4, pursing actuation yoke 184 extends upwardly such that it engages the driven surfaces of the first and second pursing actuation ears 124 and 128 extending outwardly from cable mounting hub 296 located within disposable support housing 100. By way of example, first translation nut component 182 of first motor-actuated cable mounting hub translation assembly 180 may be configured with a threaded portion 192 to provide for secure attachment to pursing actuation yoke 184. When the threaded portion 192 and associated first translation nut component 182 is seated against first bulkhead 162 surface, the first motor-actuated cable mounting hub translation assembly 180 is considered to be in a first "home" position, i.e., the most fully distally extended position where it may, for example, accept the next new disposable tissue capture device 101 and enable the accurate initial setting of the stop position for cable mounting hub 296, as described in greater detail below.

Returning to FIGS. 4 and 4A, the actuator and transfer assemblies, which are mounted within the reusable housing 14 are more clearly depicted wherein second motor and planetary gear assembly 171 is seen to be comprised of a first D.C. motor 171a having, by way of example, a 3.2 watt assigned power rating marketed under the catalog designation 118686 by Maxon Precision Motors Inc., of Burlingame, Calif. This second motor 171a is combined with a second planetary gear 171b exhibiting, by way of example, a 29:1 reduction and marketed under the catalog designation 118185 by Maxon Precision Motors Inc. (supra). The output shaft of the second planetary gear 171b is shown at 233 and is seen to extend through the second torque stop component 173. Second torque stop component 173 is bolted to the forward casing of second planetary gear 171b and is configured with a second rectangular tab portion 235 which engages a second torque stop slot 237 within reusable housing 14. Motor assembly second output drive shaft 233 is fixed by a setscrew into driving relationship with one end of the second bellows-shaped coupler 175. The opposite end of second bellows-shaped coupler 175 is connected to the second proximal circular necked-down shaft 241 of second lead screw 177. Fixed connection with second lead screw 177 is provided by another setscrew extending within second bellows-shaped coupler 175. The distal end of the second lead screw 177 is a second distal circular necked-down shaft portion 245 and is supported by second circular opening 165 in second bulkhead 163 and is rotatable therein. Second translation nut component 183 (e.g., Model No. PRM0601 supplied by Thomson, Radford, Va.) of second motor-actuated drive tube drive member translation assembly 181 is shown threadingly engaged with second lead screw 177.

As seen in FIGS. 3 and 4, capture advancement yoke 185 extends upwardly such that it engages the driven surfaces of the first and second capture advancement ears 134 and 136 extending outwardly from drive assembly drive member 324 located within disposable support housing 100. By way of example, second translation nut component 183 of second motor-actuated drive tube drive member translation assembly 181 may be configured with a threaded portion 193 to provide for secure attachment to capture advancement yoke 185. When the threaded portion 193 and associated second translation nut component 183 is seated against second bulkhead 163 surface, the second motor-actuated drive tube drive member translation assembly 181 is considered to be in a second "home" position, i.e., the most fully distally extended position where it may, for example, accept the next new disposable tissue capture device 101 and enable the accurate initial setting of the starting position for drive assembly drive member 324, as described in greater detail below.

Figure 5:
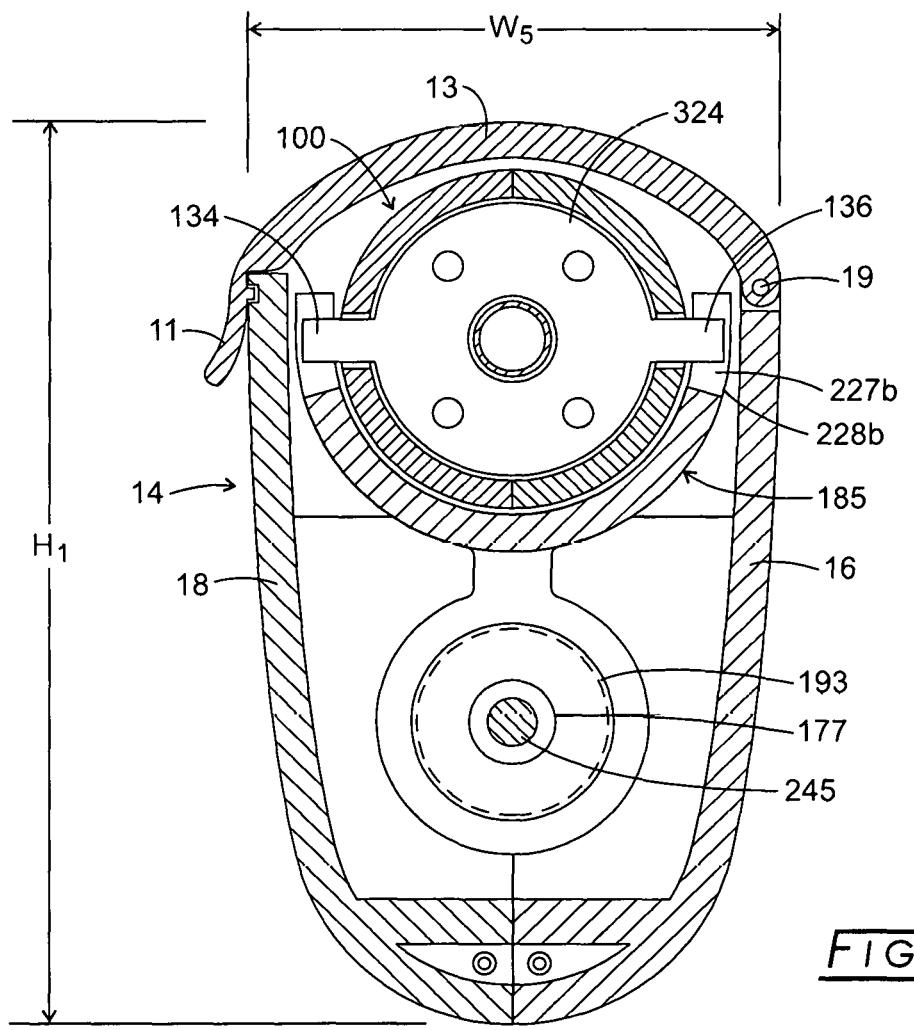
FIG. 5 is a sectional view taken through the plane 5-5 shown in FIG. 4.

A cross-sectional view of the reusable housing 14 and disposable support housing 100 are seen in FIG. 5. In this cross sectional view, reusable housing 14 includes housing left side 18, housing right side 16 and hinged cover 13. Hinge 19 enables opening and closure of hinged cover 13 to insert and remove disposable support housing 100 while latch 11 secures position of hinged cover 13 during operation of tissue retrieval instrument. Threaded portion 193 of second translation nut 183 is located within matching threaded portion of lower half of capture advancement yoke 185. The proximal upper arms 228b of capture advancement yoke 185 are seen in the upper portion of FIG. 5, whose proximal driving surface 227b is seen positioned behind first and second capture ears 134 and 136. As seen in FIGS. 3 and 5, as second motor and planetary gear assembly 171 of second motor-actuated drive tube drive member translation assembly 181 causes yoke to advance toward front of disposable support housing 100, proximal driving surface 227a will urge drive assembly drive member 324 forward toward the distal end of disposable support housing 100 and, in turn, cause deployment of tissue leaf member and tube assembly 400 within disposable tissue capture device seen in FIG. 2 and as described in greater detail in the specification that follows.

Figure 5A:
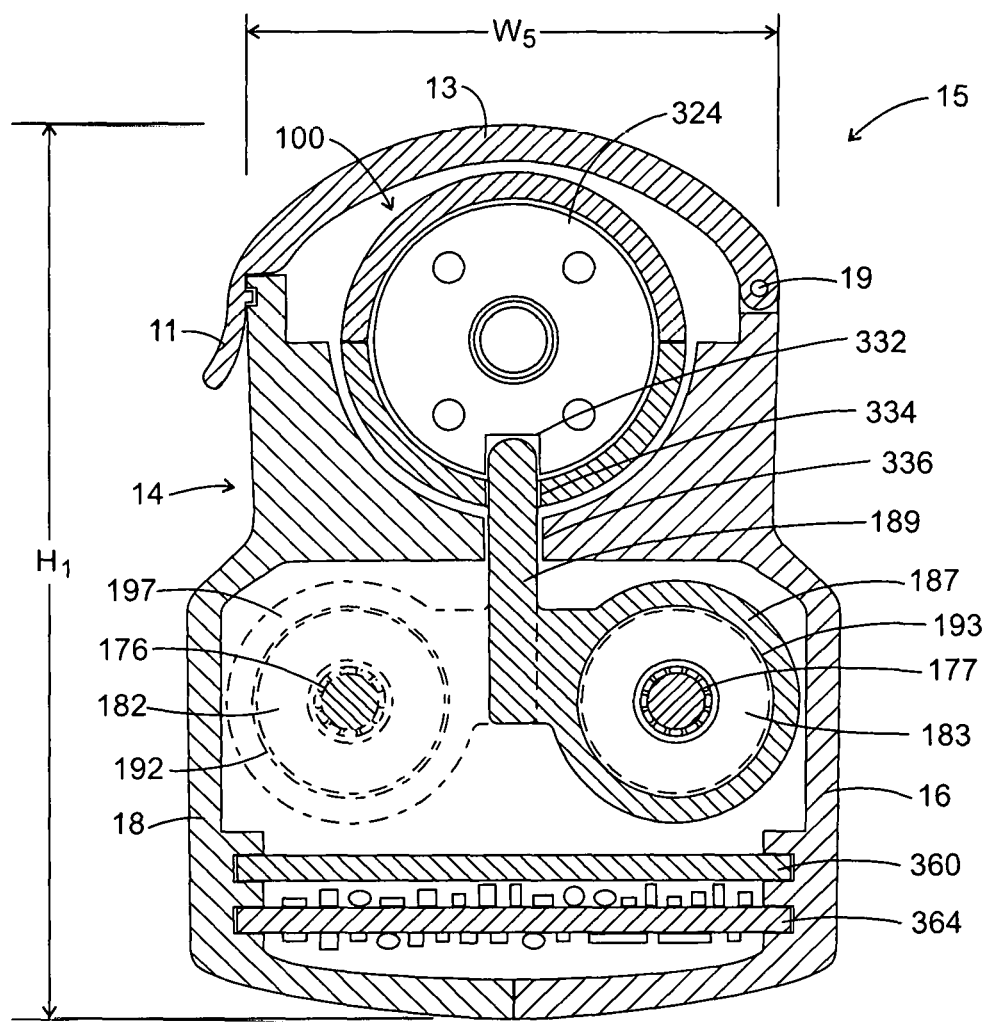
FIG. 5A is a sectional view of an alternative arrangement of the transfer assemblies in a side-by-side configuration rather than in-line configuration seen in FIGS. 4-5.

A cross-sectional view of the reusable housing 14 and disposable support housing 100 are seen in an alternative embodiment in FIG. 5A. In the cross sectional view of the alternative embodiment seen in FIG. 5A, reusable housing 14 includes housing left side 18, housing right side 16 and hinged cover 13. Hinge 19 enables opening and closure of hinged cover 13 to insert and remove disposable support housing 100 while latch 11 secures position of hinged cover 13 during operation of tissue retrieval instrument. Threaded portion 193 of second translation nut is located within matching threaded portion of second drive pin support sleeve 187. Second drive pin 189 extends through receiving cavity slot 336 and continuing through drive pin slot 334 in disposable casing 100 to engage drive assembly drive member 324 by extending into drive pin hole 332 as seen in the upper portion of FIG. 5A. As seen in FIGS. 1, 2, 5A, 18, 18A and 18C, as second motor and planetary gear assembly 171 of second motor-actuated drive tube drive member translation assembly 181 causes second drive pin 189 to advance toward front of disposable support housing 100, second drive pin 189 will urge drive assembly drive member 324 forward toward the distal end of disposable support housing 100 and, in turn, inducing advancement of leaf members 348, first electrically and thermally conductive tube 311 and second electrically and thermally conductive tube 313 resulting in deployed tissue capture basket 326 of tissue incision and retrieval instrument 12 as described in greater detail in the specification that follows. Referring now to FIGS. 1, 5A, 18, 18A, the alternative embodiment seen in FIG. 5A includes circuit board 364 that enables all of the functions provided by the external control assembly 66 seen in FIG. 1. The circuit board 364 comprises electronic components and circuits that provide [a] source of constant current to resistively heated portion of electrically conductive cutting and pursing cable 309 during tissue cutting process, [b] source of first constant voltage to first motor 170a, [c] source of second constant voltage to second motor 171a, [d] machine instructions to control timing and level of applied constant current, first constant voltage and second constant voltage, response to operator actuated switch functions, response to operator selected tissue capture diameter size and control of illumination of display components (e.g., LEDs), [e] display components (not seen in FIG. 5A) indicating status of tissue capture process as previously seen in FIG. 1 at "Initialize" display 42, "Excising display 46, pause display icon 50 and capture complete icon 52, [f] source of audible cues to operator and [g] operator control switch and capture size selection buttons (not seen in FIG. 5A). In a preferred embodiment and still referring to FIG. 5A, rechargeable battery 360 provides the source of electrical power for circuit board 364 to enable all of the powering, display and operator control functions previously provided by the external control assembly 66 seen in FIG. 1. Therefore, all of the operator actuation functions, visual cues, audible cues, two constant voltage sources, constant current source and displays previously incorporated in control assembly 66 previously seen in FIG. 1 are all incorporated within housing assembly 15 seen in FIG. 5A. The preferred embodiment seen in FIG. 5A eliminates the need for a costly external control assembly as seen in FIG. 1 as well as eliminates the need for a connecting multi-lead cable, thereby enabling greater maneuverability of the housing assembly 15 by the operator during a surgical procedure.

Referring to FIGS. 1, 3 and 4, during operation of the tissue retrieval instrument 12, the second lead screw 177 is rotated to drive the second motor-actuated drive tube drive member translation assembly 181 forwardly to effect a motorized driving of the tissue cutting and capture assembly 329 of the instrument through a drive assembly drive member 324. Referring also to FIGS. 6 and 8, such forward movement of drive assembly drive member 324 is represented in phantom at 328 and corresponding position of tissue cutting and capture assembly 329 following corresponding deployment is represented in phantom at 326. For the case of the second motor-actuated drive tube drive member translation assembly 181, the second motor and planetary gear assembly 171 drives the second motor-actuated drive tube drive member translation assembly 181 forwardly until (a) a low electrical resistance detected in resistively heated portion of electrically conductive cutting and pursing cable 309 indicating that the capture of tissue and full closure of tissue cutting and capture assembly 329 is complete and/or (b) a motor stall condition (i.e., defined as current flow in the motor exceeding a predetermined threshold level, e.g., 100 milliamp) is encountered which represents a completion of pursing activity and associated tissue volume capture. A control assembly associated with tissue incision and retrieval instrument 12 then recognizes the low electrical resistance and/or high (stall) motor current indicating that the tissue capture has been completed and illuminates capture complete icon 52.

The disposable tissue capture device 101 with disposable support housing 100 and delivery cannula 22 is illustrated in detail in connection with FIGS. 6 and 7. Disposable support housing 100 is formed of two identically molded housing halves, which are joined, together and additionally interconnected with the delivery cannula 22, threaded and smoke/steam exhausting suction manifold 26 which is connected with suction tube 62. The embodiment of these figures shows the distal tip 34 at the forward region of cannula 27 of the delivery cannula 22 to incorporate a pair of polymeric tip components 264 and 266, the latter component providing both a ramp structure for four leaf members and two conduits for the rigid tubes of a tissue cutting and capture assembly 329 retained within the forward region 30. A surgically sharp cutting blade 31 is shown in these figures in the manner as described in connection with FIG. 4. In general, the freely rotatable suction manifold 26 is retained in position over the cannula 22 by collar 28 and the entire rod-like delivery cannula 22.

Referring to FIGS. 7 and 8, a sectional view of the support housing 100 is revealed showing its formation from two identical disposable casings 270 and 272 that are joined together by the application of adhesive (e.g., cyanoacrylate) along disposable housing joint line 21. Note that disposable casings 270 and 272 are securely attached to delivery cannula 22 at their forward portions by the application of adhesive (e.g., cyanoacrylate). Cannula 22 is seen to be a hollow tube and extends through an evacuation chamber 274 formed within freely rotatable manifold 26. It further may be observed that the delivery cannula 22 is formed with a hole or aperture 276 such that vacuum can be communicated from flexible suction conduit 62 into the chamber 274 and then along delivery cannula 22 toward the forward region of cannula 27. As seen in FIG. 8A at the opposite end of the molding components 270 and 272, the earlier-described first and second electrical contacts 120 and 122 are secured at the end face 103 of the disposable housing 100.

Referring to FIGS. 8 and 8A, extending from a rearward bulkhead represented generally at 280 and defined by molded components of support housing 110 disposable casings 270 and 272, there is provided an elongate support tube 282. By way of example, support tube 282 is formed of stainless steel (e.g., stainless steel 304 tubing available from Micro Group, Inc., Medway, Mass.) and is anchored at the rearward side of fifth bulkhead 280 by sleeve 284 adhesively locked into position on support tube 282. Support tube 282 extends symmetrically along longitudinal axis 8 for engagement with cannula distal end 25 forward tip assembly. As seen in FIG. 8A, the proximal ends of electrically conducting first and second disposable housing lead wires 114 and 116 extend to and are connected to first and second terminals 121 and 123, respectively.

Referring to FIG. 9, first and second ends 148 and 154 of the multi-strand, braided stainless steel cable (e.g., stainless steel Type 316 cable containing 7 to 19 strands in which each strand has a diameter ranging from about 0.0008 to 0.0020" the cable available from Fort Wayne Metals, Fort Wayne, Ind.) extend from their connection with the leaf member and tube assembly 400 of the instrument located at forward region of cannula 27 to and are inserted into the annular gap between pursing cable locking sleeve 322 (e.g., 0.125-inch long sections of stainless steel 304 tubing available from Micro Group, Inc., Medway, Mass.) and cylindrical section 321 located at proximal end of cable mounting hub 296. The pursing cable locking sleeve 322 is sized to provide an interference fit to cylindrical section 321 located at proximal end of cable mounting hub 296 and secured with adhesive (e.g., cyanoacrylate adhesive). Alternatively, and throughout the disclosure presented herein, the resistively heated portion of electrically conductive cutting and pursing cable 309 containing multiple strands could be replaced by a small diameter wire comprising a single strand of metal (e.g., stainless steel, nickel, nickel alloy, titanium or titanium alloy wire available from Fort Wayne Metals, Fort Wayne, Ind.) having a diameter in the range from 0.002 to 0.005 inch.

Looking additionally to the sectional views in FIGS. 9, 10 and 11, cable mounting hub 296 is seen to be formed with two longitudinally disposed and radially spaced channels 306 and 308 into each of which tensionable portions of cutting and pursing cables as at 118 and 119, respectively, extend. In this regard, tensionable portion of cutting and pursing cable 118 is seen extending through channel 306 and tensionable portion of cutting and pursing cable 119 is seen extending through channel 308. Both first and second tensionable portions of cutting and pursing cables 118 and 119 are restrained between cylindrical section 321 of cable mounting hub 296 and pursing cable locking sleeve 322 by means of adhesive 323. Looking additionally to FIG. 8, uniform tensioning of the two ends of the load-bearing tensionable portions of cutting and pursing cables 118 and 119, connected, in turn to the proximal ends 148 and 154 of resistively heated portion of electrically conductive cutting and pursing cable 309 is essential to a symmetrical pursing action and symmetrical cage structuring of the tissue capture basket 326.

Referring to FIG. 10 reveals the presence of first and second pursing actuation ears 124 and 128 extending outwardly from the cable mounting hub 296. These pursing actuation ears are shown at 124 and 128 within respective slots 126 and 127 of support housing 100. With this arrangement, as the resistively heated portion of electrically conductive cutting and pursing cable 309 is electrically heated with constant electrical cutting current, it is drawn in tension forwardly in the sense of the instrument to, in turn, pull the cable mounting hub 296 (in attachment with load-bearing proximal ends 148 and 154 of resistively heated portion of electrically conductive cutting and pursing cable 309 cable) in slideable fashion forwardly over the support tube 282. This sliding movement under the drive of cable tension continues until the load-bearing cable mounting hub 296 affixed to the first and second proximal ends 148 and 154 of resistively heated portion of electrically conductive cutting and pursing cable 309 encounters and engages a pursing actuation yoke 184 which, as seen in FIG. 4 is positioned in a predetermined fixed "stop" location for the cable mounting hub 296 corresponding to the operator selected maximum effective diametric extent of opening of the containment structure or cage generated by the tissue cutting and capture assembly 329 as seen in FIG. 6. The "stop" position of the cable mounting hub 296 is selected by the operator prior to the start of the tissue excision and capture procedure by depressing either the increase capture diameter selector button 36 or the decrease capture diameter selector button 38 on the front panel of the control assembly 66 as seen in FIG. 1. Corresponding to depressing either the increase capture diameter selector button 36 or the decrease capture diameter selector button 38 on the front panel of the control assembly 66, a numerical value of the operator-selected maximum effective diametric extent of opening of tissue cutting and capture assembly 329 is visually seen at display 37. For example, that diametric extent will range from about 10 mm to about 30 mm.

When the cable mounting hub 296 engages pursing actuation yoke 184 while drive assembly drive member 324 continues to be driven forward to urge the forward deployment of the tissue cutting and capture assembly 329, the two load-bearing proximal ends of first and second tensionable portion of cutting and pursing cables 118 and 119 continue to be stressed in tension. Tension in load-bearing proximal ends of first and second tensionable portion of cutting and pursing cutting cables 118 and 119 continues to an extent that it causes the onset of a pursing activity of the electrically heated cables at the leading edge of the leaf member and tube assembly 400. Simultaneously, tension in load-bearing proximal ends of first and second tensionable portion of cutting and pursing cables 118 and 119 induces an increased mechanical and associated electrical load that is detected in the form of a measurable increase in the electric current, IMOTOR2 supplied to second motor 171a. The increase in electrical current delivered to second motor 171a is measured by electrical circuitry incorporated within control assembly 66 to provide electrical power to second motor 171a as it is advancing the tissue cutting and capture assembly 329. Upon the detection of a level of the electrical current, IMOTOR2 delivered to second motor 171a that exceeds a predetermined threshold level, IMAXOPEN, then a predetermined voltage level is applied to first motor 170a to further increase tension on the two load-bearing proximal ends of first and second tensionable portion of cutting and pursing cables 118 and 119, thereby increasing, at a predetermined speed, the rate at which the pursing down of the tissue cutting and capture assembly 329.

Referring to FIG. 11 reveals the presence of first and second pursing actuation ears 134 and 136 extending outwardly from drive assembly drive member 324. These pursing actuation ears are shown at 134 and 136 within respective slots 130 and 131 of left disposable casing 270 and right disposable casing 272, respectively. Also seen in FIG. 11 are first and second cutting and pursing cable conduits 305 and 307, respectively. In addition, FIG. 11 reveals first and second lead wire conduits 302 and 304, respectively.

The predetermined voltage and associated speed at which first motor 170a advances the cable mounting hub 296 in a direction to induce an increased rate of pursing down of the tissue cutting and capture assembly 329 as well as the predetermined voltage and associated speed at which second motor 171a advances the drive assembly drive member 324 forward to urge the forward deployment of the tissue cutting and capture assembly 329 combine to determine the final shape of the tissue cutting and capture assembly 329 and associated shape of the tissue sample captured.

Figure 18:
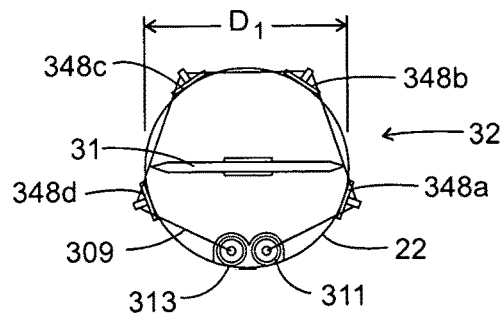
FIG. 18 is a frontal view of distal end of disposable tissue capture device seen in FIG. 2 prior to deployment of tissue cutting and capture assembly.
Figure 18D:
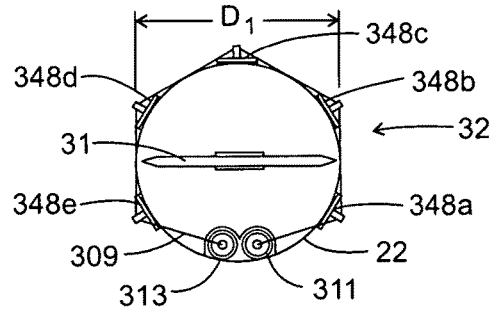
FIG. 18D is a frontal view of distal end of disposable tissue capture device seen in FIG. 2 prior to deployment of tissue cutting and capture assembly and comprising five leaf members.
Figure 18A:
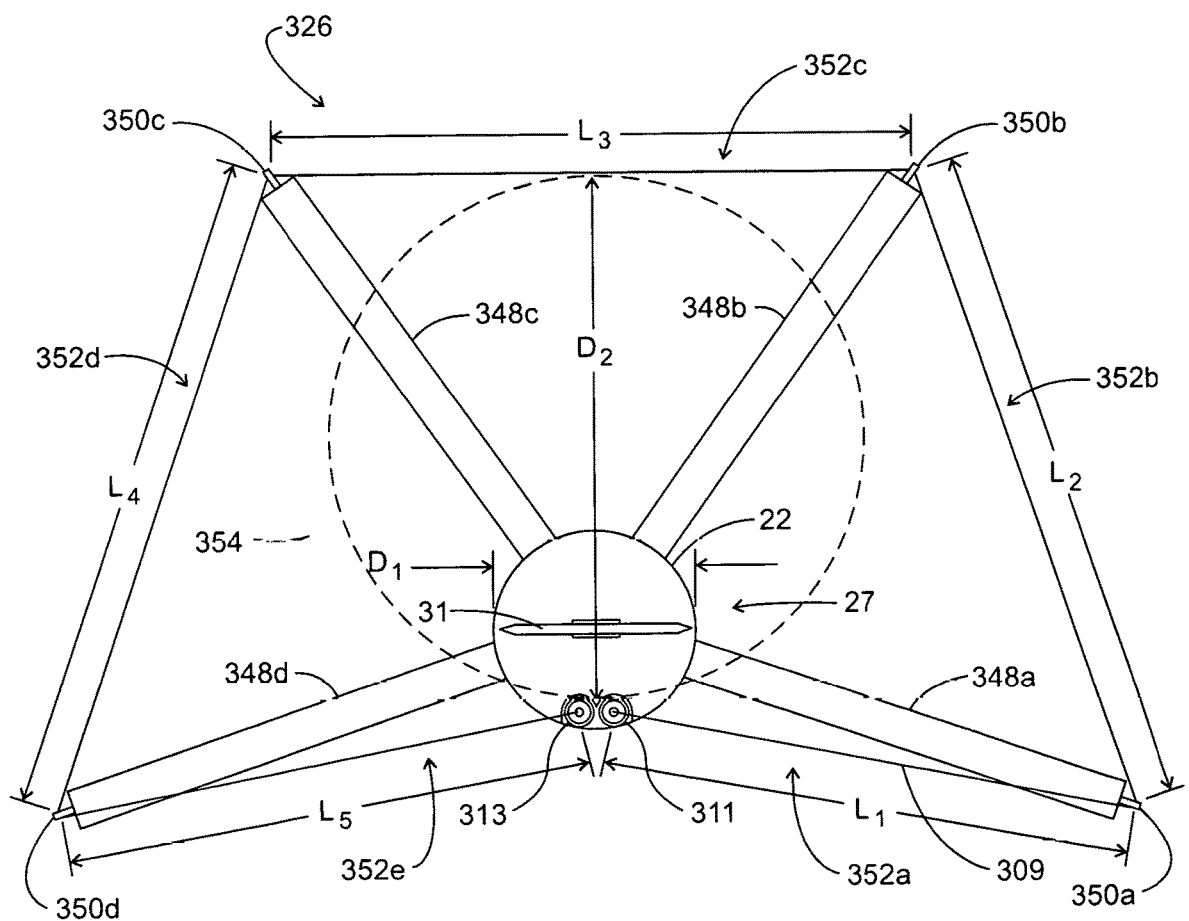
FIG. 18A is a frontal view of distal end of disposable tissue capture device seen in FIG. 2 after deployment of tissue cutting and capture assembly to position of maximum opening.

The combined effect of simultaneously translating both the drive assembly drive member 324 and the cable mounting hub 296 in respective directions required to induce pursing down of tissue cutting and capture assembly 329 is described in greater detail in connection with FIGS. 18-18C. By way of example, FIGS. 18 and 18A present front views of the tip region 27 of delivery cannula 22, illustrating the orientation of blade 31, four leaf members 348a-348d, first and second thermally and electrically conductive tubes 311 and 313 as well as resistively heated portion of electrically conductive cutting and pursing cable 309 in a retracted state in FIG. 18 and as leaf members 348a-348d and resistively heated portion of electrically conductive cutting and pursing cable 309 emerge in FIG. 18A. As the leaf members 348a-348d are being deployed, the resistively heated portion of electrically conductive cutting and pursing cable 309 spanning and passing through respective eyelets at the distal ends of leaf members 348a-348d receives constant level of electrical current to resistively heat the cable to a level sufficient to enable the thermal cutting of tissue. The minimum temperature of the cable is maintained above about 450 C to achieve the thermal cutting of tissue through the heating of tissue cells in contact with the resistively heated portion of electrically conductive cutting and pursing cable 309 to a level at which the contacted cells, heated via thermal conduction from the heated cable, rupture as a result of the vapor pressure generated by raising the cellular water within the cells above the boiling point. The rupture of the cells receiving heat from the resistively heated portion of electrically conductive cutting and pursing cable 309 (via thermal conduction) induce a scission of the tissue contacted by the heated cable to achieve the desired cutting of tissue required for its capture.

The above described mechanism for thermal cutting of tissue through direct thermal conduction heat from a resistively heated portion of electrically conductive cutting and pursing cable 309 to the contacted tissue being incised is distinct from electrosurgical cutting. In the case of the above described thermal cutting of tissue, electrical current (at a predetermined constant level) flows only through the resistively heated portion of electrically conductive cutting and pursing cable 309 and not through the tissue being cut. By way of example, a constant current level in the range of 4 to 6 amps and a maximum applied voltage of 20 to 30 volts for the case of a resistively heated portion of electrically conductive cutting and pursing cable 309 having 19 strands of stainless steel type 316 with each individual strand having a diameter in the range from about 0.0008 inch to about 0.0020 inch, the preferred current and maximum voltage depending on the resistance of the wire and cable and the maximum heated length that must conduct current during tissue capture. By way of another example, a constant current level in the range of 1.2 to 1.8 amps and a maximum applied voltage of 30 to 50 volts for the case of a resistively heated portion of electrically conductive cutting and pursing cable 309 having 7 strands of stainless steel type 316 with each individual strand having a diameter of about 0.0012 inch, the preferred current and maximum voltage depending on the resistance of the wire and cable and the maximum heated length that must conduct current during tissue capture.

Since the mechanism of cutting of tissue using an electrically heated wire or cable avoids any flow of electrical current into the adjacent tissue but rather only the conduction of heat into adjacent tissue during tissue cutting, the resulting depth of thermal injury at the surface of the captured tissue specimen is limited to less than about 0.001" to 0.002". In contrast, electrosurgical cutting of tissue with a wire or cable in prior art devices requires the flow of electrical current from the wire or cable into and through the tissue being incised wherein an electrical arc is formed in the gap between the wire or cable and the tissue as a result of application of a high voltage difference between the wire or cable and the tissue, typically at a level of greater than 1000 volts (peak-to-peak) at a frequency of at least 300 kHz. In the case of electrosurgical cutting to excise and capture a volume of tissue, as specified in U.S. Pat. No. 6,471,659 and incorporated herein by reference, the essential flow of electrical current into and through adjacent tissue to achieve tissue cutting causes unwanted heating of adjacent tissue well beyond the path of cutting resulting in thermal damage to portions the excised volume of captured tissue. The thermal damage to portions the excised volume of captured tissue are disadvantageous in that portions of the captured tissue specimen, intended for subsequent examination by a pathologist, are compromised and limit the available portions of the capture tissue specimen suitable for such examination (e.g., assessment of the boundary between malignant and healthy tissue).

In FIG. 18, the four leaf tips 350a-350d are visible in connection with portions of the resistively heated portion of electrically conductive cutting and pursing cable 309. Note that the resistively heated portion of electrically conductive cutting and pursing cable 309 extends from the opening of the first electrically and thermally conductive tube 311 to an eyelet located at the leaf tips 350a-350d of each successive leaf member 348a-348d, respectively, and finally to the opening of the second electrically and thermally conductive tube 313. As seen in FIG. 18A, during the deployment of leaf members 348a-348d combined with the deployment of first and second electrically and thermally conductive tubes 311 and 313, the minimum diametric extent, D2 of the assembly of leaf members 348a-348d and tubes 311-313 is expanding to circumscribe the targeted tissue volume 354 to be removed.

The importance of the translating the cable mounting hub 296 in a direction to increase the rate of pursing of the tissue cutting and capture assembly 329 is described in greater detail in conjunction with FIGS. 18, 18A, 18B and 18C. By way of example, a fully expanded tissue cutting and capture assembly 329 is seen in cross-sectional end view in FIG. 18A wherein the dimensions of the segments of the resistively heated portion of electrically conductive cutting and pursing cable 309 between first electrically and thermally conductive tube 311 and leaf member 348a, leaf members 348a-348d and leaf member 348d second electrically and thermally conductive tube 313 are designated L1, L2, L3, L4 and L5, respectively. After attaining the maximum expansion of the tissue cutting and capture assembly 329 as seen in the example end cross-sectional view in FIG. 18A, the subsequent tissue cutting and simultaneous pursing down of the leaf members 348a-348d requires that the combined length of the segments 352a-352e of the resistively heated portion of electrically conductive cutting and pursing cable 309 cable length be withdrawn inside disposable tissue capture device 101 so that leaf tips 350a-350d and first and second electrically and thermally conductive tubes 311 and 313 all converge at a single pursed-down point 356 as seen in the side views in FIGS. 18B and 18C. Returning to FIG. 18A and by way of example, assume the following dimensions (in units of inches) for the delivery cannula and the deployed tissue capture basket 326 of the tissue cutting and capture assembly 329 when in the position of its maximum diametric extent for the case of an operator selected targeted tissue minimum diameter of 0.8 inch or 20 mm:

L1=0.69
L2=0.83
L3=0.86
L4=0.83
L5=0.69
D1=0.26
D2=0.80

Figure 18B:
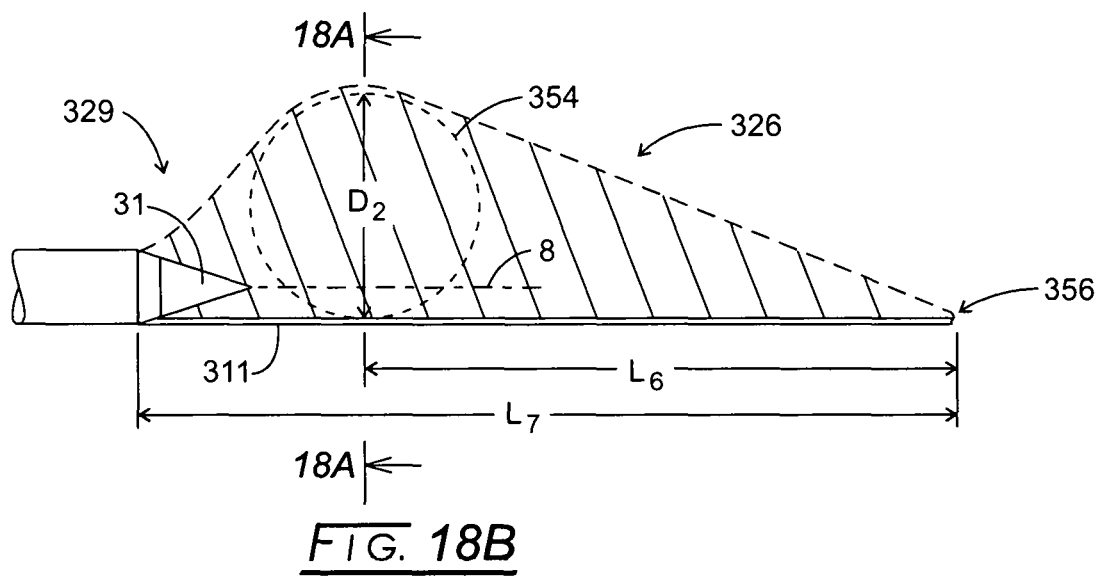
FIG. 18B is a partial side view of distal end of disposable tissue capture device seen in FIG. 2 after deployment of tissue cutting and capture assembly to position of maximum opening without the benefit of retraction of cable mounting hub.

Based on the above example, the combined length of all five-cable segments 352a-352e equals 3.90 inch. Since there are two ends of the resistively heated portion of electrically conductive cutting and pursing cable 309 that extend in a rearward manner from tissue cutting and capture assembly 329, the length of each of the two ends of the resistively heated portion of electrically conductive cutting and pursing cable 309 that needs to be retracted is one-half of 3.90 inch or 1.95 inch per end of the resistively heated portion of electrically conductive cutting and pursing cable 309. As described above, the retracting of the ends of the cutting and pursing cable be withdrawn inside disposable tissue capture device 101 so that leaf tips 350a-350d and first and second electrically and thermally conductive tubes 311 and 313 all converge at a single pursed-down point 356 as seen in the side views of tissue cutting and capture assembly 329 in FIGS. 18B and 18C. As seen in FIG. 18B, if the only method for pursing down the capture basket by retracting the ends of the resistively heated portion of electrically conductive cutting and pursing cable 309 is the continuing forward deployment of the capture basket members as specified in U.S. Pat. No. 6,471,659 (e.g., leaf members 348a-348d and first and second electrically and thermally conductive tubes 311 and 313 in the present example), then the longitudinal extent, L6 of the tissue cutting and capture assembly 329 beyond the point of the maximum opening of the deployed tissue capture basket 326 is 1.95 inch. As seen in FIG. 18B, the overall length, L7 of the tissue capture basket at the completion of tissue excision and capture is 2.70 inch. As seen in the side view of the tissue cutting and capture assembly 329 in FIG. 18B and the extent of the deployed tissue capture basket 326, the volume of tissue incised and captured (shaded region) is substantially larger than the targeted tissue volume 354. In addition, the excessive longitudinal extent of the deployed tissue capture basket 326 beyond the distal boundary of the targeted tissue volume 354 is disadvantageous as the longitudinal extent may cause unwanted impingement upon adjacent tissue structures, blood vessels or bone.

Figure 18C:
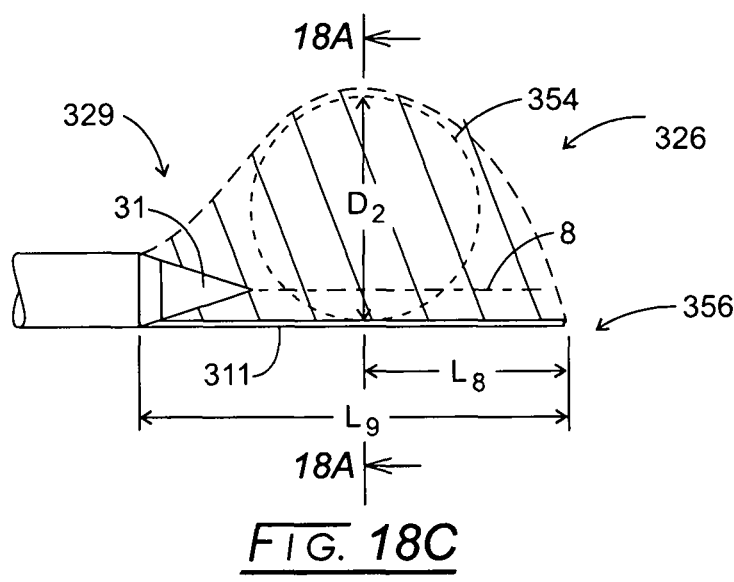
FIG. 18C is a partial side view of distal end of disposable tissue capture device seen in FIG. 2 after deployment of tissue cutting and capture assembly to position of maximum opening with the benefit of retraction of cable mounting hub.

In contrast and referring now to FIGS. 4, 8, 9 and 18C, the preferred embodiment of the present disclosure specifies the use of a first motor and planetary gear assembly 170 in combination with a pursing actuation yoke 184 to actively retract the first and second tensionable portions of cutting and pursing cables 118 and 119 that are affixed to the cable mounting hub 296 as it is driven by the pursing actuation yoke 184. By further increasing the tension on the two load-bearing proximal ends of first and second tensionable portions of cutting and pursing cables 118 and 119 by driving the cable mounting hub 296 in a rearward direction at a predetermined speed, the rate at which the pursing down of the tissue cutting and capture assembly 329 can be precisely controlled by control assembly 66 to provide a preferred shape of the deployed tissue capture basket 326. By way of example and in contrast to the shape and size of the tissue capture basket seen in FIG. 18B, the apparatus, system and method of the present disclosure enables the cutting and capture of a targeted tissue volume 354 having a preferred shape and size (shaded region of FIG. 18C). As seen in FIG. 18C, the longitudinal extent, L8 of the tissue cutting and capture assembly 329 beyond the point of the maximum opening of the deployed tissue capture basket 326 is only 0.63 inch. Also as seen in FIG. 18B, the overall length, L9 of the tissue capture basket at the completion of tissue excision and capture is only 1.37 inch, substantially smaller than the longitudinal extent in connection with prior art methods and as seen in FIG. 18B.

Referring now to FIGS. 12 and 18, the forward region of cannula 27 of delivery cannula 22 is revealed in sectional detail. In the figure, the delivery cannula 22 is seen extending forwardly to a polymeric (e.g., polyetherimide) tip component 264. Next inboard from the internal surface of the delivery cannula 22 are four leaf member and tube assembly 400 leaf members 348a-348d and first and second electrically and thermally conducting tubes 311 and 313 in a pentagonal configuration. Extending next inwardly inboard is the earlier-described support tube 282, which is seen to extend to tip 32 and with a flared end 346 at its distal region in addition to being adhesively coupled to the tip component 266. This flaring is found to be helpful in permitting support tube 282 to overcome the rather substantial forwardly directed forces occurring during the forward deployment of the leaf member and tube assembly 400 leaf members 348a-348d as well as first and second electrically and thermally conductive tubes 311 and 313.

Referring to FIGS. 12, 13 and 14, extending beyond and adhesively attached to the distal end of support tube 282 is a cutting blade support member 230 which is mechanically and adhesively attached to the shank of cutting blade 31 by positioning locking pin 45 through both mounting hole 47 in base 231 of support member 230 and through hole 43 in shank 41 of blade 31. The dimensional extent of the confronting severing portions of the base of cutting blade 31 is selected to provide an effective length no greater than the corresponding maximum diametric extent of blade support member 230. In FIG. 12, that extent may be observed at stylized dashed locus of movement line 355. In deploying the leaf member and tube assembly 400, the forward or leading edge thereof containing the noted resistively heated portion of electrically conductive cutting and pursing cable will cut a path somewhat similar to that shown at dashed line 354, reaching the leaf member and tube assembly 400 predetermined maximum peripheral diametric extent at that point in the deployment when pursing commences as the cable mounting hub 296 engages the initial preselected position of pursing actuation yoke 184 as described in conjunction with the FIG. 4.

FIG. 12 further illustrates the smoke-steam evacuation ports 35 which communicate in vacuum association with an evacuation channel established initially as a gap between the outer surface of leaf members 348a-348d as well as first and second electrically and thermally conductive tubes 311 and 313 and the internal surface of tip component 266. The channel then extends in a rearward direction as a gap adjacent to internal surface of delivery cannula 22 to the suction manifold 26 (FIG. 2).

FIG. 15 reveals a section through the polymeric confinement sleeve 264. That component functions as a confinement or alignment sleeve for each one of the four leaf members 348a-348d and first and second electrically and thermally conductive tubes 311 and 313. Each of these leaf members 348a-348d as well as first and second electrically and thermally conductive tubes 311 and 313 are slideably located within a receiving chamber shown respectively at 370a-370e, which extends within delivery cannula 22.

Referring now to FIGS. 15A, 15B and 20, sectional views of first electrically and thermally conductive tube 311 provide additional details that also apply to matching second electrically and thermally conductive tube 313. As seen in the transverse cross-sectional view of FIG. 15A, first electrically and thermally conductive tube 311 is surrounded by a first electrically insulative covering 318 (e.g., polyester shrink tubing having a thickness of 0.001 inch and available from Vention/Advanced Polymers, Salem, N.H.). The first electrically insulative covering 318 prevents electrical current flow between the closely spaced first and second electrically and thermally conductive tubes 311 and 313 that are subjected to a voltage difference of about 20 volts or greater during the application of constant current through first and second electrically and thermally conductive tubes 311 and 313 first and second electrically and thermally conductive tubes 311 and 313 via first and second disposable housing lead wires 114 and 116 and supplied by control system 66 (see FIG. 1) or by circuit board 364 in combination with rechargeable battery 360 (see FIG. 5A). Referring to FIGS. 15A and 15B, a first electrically insulative sleeve 310 in positioned on the inside diameter of first electrically and thermally conductive tube 311 along the full length of first electrically and thermally conductive tube 311 except for crimped down section 320 located at the distal end of first electrically and thermally conductive tube 311. This arrangement of first electrically insulative sleeve 310 along nearly all of the interior surface of first electrically and thermally conductive tube 311, except at its distal end incorporating crimped down section 320, assures that electrical current flow from first electrically and thermally conductive tube 311 to resistively heated portion of electrically conductive cutting and pursing cable 309 is confined to that portion of the resistively heated portion of electrically conductive cutting and pursing cable 309 that is in contact with tissue, thereby dissipating the heat generated within the resistively heated portion of electrically conductive cutting and pursing cable 309 to the tissue to effect incision of the tissue. By way of example, first electrically insulative sleeve 310 may be thin-walled polyimide tubing having a wall thickness of 0.001 inch and available from Vention/Advanced Polymers, Salem, N.H.

As seen in FIGS. 15A and 15B, the continuous flexible cable (or single strand wire) functions in two distinctly different modes depending on whether the cutting and pursing cable or wire is proximal or distal to the point of electrical contact 390. As seen in FIG. 15B, the current flow path 399 proceeds along the length of first electrically and thermally conductive tube 311 until electrical contact is made with the resistively heated portion of electrically conductive cutting and pursing cable 309, the electrical contact enabling electrical current to commence to flow in the resistively heated portion of electrically conductive cutting and pursing cable 309 in portion of cable distal to point of contact 397 that begins at transition boundary 396. In that portion of cutting and pursing cable that is proximal to the point of electrical contact 398, no electrical current can flow and this portion of the cutting and pursing cable is referred to as first tensionable portion of cutting and pursing cable 118. Therefore, as specified above, the function of the cutting and pursing cable depends on its position relative to the point of electrical contact 390 between the first electrically and thermally conductive tube 311 and the cutting and pursing cable. In a preferred embodiment, first and second electrically and thermally conductive tubes 311 and 313 are fabricated using a pure silver or silver alloy preferably with at least 90% silver content. By way of example, silver tubes specified for said first and second electrically and thermally conductive tubes 311 and 313 are available from Otto Frei, Oakland, Calif.

Referring now to FIGS. 12 and 15, tip component 266 directs each of the four leaf members 348*a*-348*d* of the leaf member and tube assembly 400 into slideable engagement with a designated ramp located somewhat rearwardly within the confinement sleeve 264. Thus, confinement sleeve 264 and tip component 266 cooperate to provide a guidance assembly represented generally at 267. Each of the leaf members 348 is configured with a perpendicularly oriented tip carrying a single eyelet 327 that slideably receives resistively heated portion of electrically conductive cutting and pursing cable 309. The four ramps established by the tip component 266 provide exit guidance for leaf members 348*a*-348*d* as the drive tube 325 urges them forwardly. In general, the four ramps established by tip component 266 provide an angle of attack for the individual leaf members 348 of about 45° with respect to the longitudinal axis 8 of the instrument. The normally oriented, eyelet-containing tip 330 of a leaf member 348 is shown in FIG. 17. As seen in FIGS. 18 and 18A, resistively heated portion of electrically conductive cutting and pursing cable 309 emerges from first and second electrically and thermally conductive tubes 311 and 313, passes slideably and sequentially through the eyelet 327 of leaf tip 330 of each of the four leaf members 348*a*-348*d*.

As noted above and seen in FIGS. 18 and 18A, a single resistively heated portion of electrically conductive cutting and pursing cable 309 extends advantageously from the orifice of each of the first and second electrically and thermally conductive tubes 311 and 313 and sequentially through an eyelet 327 at the eyelet containing tip 330 of each leaf member 348 forming the perimeter of the tissue cutting and capture assembly 329. The cable pathway arrangement seen in FIGS. 18 and 18A is critical to the proper functioning of resistively heated portion of electrically conductive cutting and pursing cable 309 as it enables electrical current flow only in those segments 352*a*-352*e* of the resistively heated portion of electrically conductive cutting and pursing cable 309 that span between first and second electrically and thermally conductive tubes 311 and 313 and sequential leaf members 348*a*-348*d*. Note that it is functionally essential that the resistively heated portion of electrically conductive cutting and pursing cable 309 extends from the tissue cutting and capture assembly 329 rearwardly to proximal portions of the disposable tissue capture device 101 and terminate at the cable mounting hub 296 to enable the previously described pursing down of the deployed tissue capture basket 326. However, it is essential that electrical current flow only those portions or segments 352*a*-352*e* of the resistively heated portion of electrically conductive cutting and pursing cable 309 that are in contact with tissue since the cable will otherwise overheat and break under the applied mechanical tensile load applied during cutting and pursing down of the leaf members 348*a*-348*d*. The sliding electrical contact between the resistively heated portion of electrically conductive cutting and pursing cable 309 and the orifices of the first and second electrically and thermally conductive tubes 311 and 313, in the presence of sufficient tension between the cable and the orifices, enables sufficiently low electrical contact resistance to support the required level of constant current (e.g., 4 to 6 amps for a 19-strand cable) required for heating the resistively heated portion of electrically conductive cutting and pursing cable 309 to sufficiently high temperature level (e.g., above about 450 C) to enable thermal cutting of tissue.

It should be understood that alternative numbers of leaf members 348 may be employed in tissue cutting and capture assembly 329. By way of further examples, five leaf members 348*a*-348*e* may be used, as seen in FIGS. 15C and 18D in place of the example configuration shown in FIGS. 15 and 18-18A containing only four leaf members 348*a*-348*d*. Fortuitously, the use of a single current-carrying resistively heated portion of electrically conductive cutting and pursing cable 309 enables the employment of a multiplicity of leaf members without significantly increasing the complexity of assembly or compromising the tissue cutting and pursing down functions of the tissue cutting and capture assembly 329. Nonetheless, consideration must be given to the lateral and torsional stability of the leaf members 348 during the deployment, cutting and pursing down processes. Testing has confirmed that the employment of four leaf members 348a-348d, as seen in FIGS. 18-18A provides a tissue cutting and capture assembly 329 of sufficient lateral and torsional stability to achieve tissue cutting and capture as illustrated in FIG. 18C.

While appearing somewhat complex at first observation, the pentagonally associated electrically and thermally conductive tubes 311-313, leaf members 348a-348d, resistively heated portion of electrically conductive cutting and pursing cable 309 and polymeric guide tubes or conduits of the leaf member and tube assembly 400 can be fabricated at costs commensurate with the disposable nature of the component 101 with support housing 100 and associated delivery cannula 22. For the leaf member and tube assembly 400 to perform, it must emerge from the guidance assembly 267 alignment sleeve 264 and an associated tip 266 ramp unconstrained until it reaches that condition wherein the cable associated with it moves no further. At that juncture, the leaf leading edges commence to define a closing or pursing hemispherical locus of movement. Individual leaf members are somewhat diminutive, being chemically milled from stainless steel with a widthwise extent selected to impart a lateral stability as well as flexibility during their outward movement. With such select structuring any warping away from the desired hemispherical pursing activity is avoided. This pursing activity forms a generally curvilinear cage periphery, which may be defined within planes parallel with the longitudinal axis of the instrument. Stability with respect to the somewhat transverse forces involved during the retraction or pursing action of the cables also is achieved with the selection of leaf thickness and width, consideration also being given to requisite leaf flexibility.

For the instant embodiment of four leaf members, stainless steel leaf members (e.g., full-hard stainless steel Type 304) having a thickness, t1 of about 0.003 inch to 0.005 inch and a widthwise extent, W3 of about 0.070 inch to 0.080 inch is utilized as seen in FIGS. 16 and 17. Each leaf member 348 is covered by a thin, electrically insulative coating (e.g., Parylene N, Specialty Coating Systems, Indianapolis, Ind.) capable of withstanding temperatures of up to at least 450 C in order to prevent unwanted electrical current flow between the leaf members during the application of electrical power. Preferably, the thickness of the electrically insulative coating applied to all exterior surfaces of leaf member 348 is in the range from 0.00015 inch to 0.0005 inch, preferably about 0.0002 inch.

Construction of a preferred pentagonal embodiment of the assembly of leaf members 348a-348d and electrically and thermally conductive tubes 311-313 is illustrated in connection with FIGS. 19, 19A and 20. To form the assembly of leaf members 348a-348d as well as first and second electrically and thermally conductive tubes 311 and 313 represented generally at 400 in FIG. 20, the stainless steel material is chemically milled to produce each of the leaf members 348a-348d from flat stainless steel stock. As seen in FIG. 16, the width of the individual leaf member 348 becomes narrower at eyelet containing tip 330 to enable twisting tip about 90 degrees relative to the plane of the leaf member 348 to orient plane of eyelet generally at a right angle relative to the plane of the leaf member 348 as seen at 331 in FIG. 17. The orientation of the eyelet of each leaf member 348 generally at a right angle relative to the plane of the leaf member 348 reduces the dynamic friction association with the sliding movement of resistively heated portion of electrically conductive cutting and pursing cable 309 during cutting and pursing processes associated with the deployment of the tissue capture basket 326. Also, as seen in FIGS. 16 and 20, a retaining notch 349 is formed at the proximal end of leaf member 348 to enable secure attachment of leaf member 348 to the leaf and tube support member 347.

A detailed cross-sectional end view and side view of the first electrically and thermally conductive tube 311 are seen in FIGS. 15A and 15B including dimension references, as noted. The cross-sectional views and components described below are also representative of the identical second electrically and thermally conductive tube 313. A thin-walled first electrically insulative sleeve 310 is positioned inside the full length of the first electrically and thermally conductive tube 311 to electrically insulate resistively heated portion of electrically conductive cutting and pursing cable from the first electrically and thermally conductive tube 311 except at the crimped down section 320 at the distal tip of first electrically and thermally conductive tube 311. Advantageously, the reduction of the inner diameter of the first electrically and thermally conductive tube 311 at its distal tip reduces the electrical contact resistance between the sliding resistively heated portion of resistively heated portion of electrically conductive cutting and pursing cable 309 and the first electrically and thermally conductive tube 311 as well as maintaining the first electrically insulative sleeve 310 proximal to the point of essential electrical contact between the cable and the tube. Also, a thin-walled first electrically insulative covering 318 is disposed on the exterior surface of first electrically and thermally conductive tube 311 to electrically insulate the first electrically and thermally conductive tube 311 from the immediately adjacent second electrically and thermally conductive tube 313. Also, a thin-walled second electrically insulative sleeve 312 (not shown) is positioned inside the full length of the second electrically and thermally conductive tube 313 to electrically insulate resistively heated portion of electrically conductive cutting and pursing cable 309 from the second electrically and thermally conductive tube 313 except at the crimped down section at the distal tip of first electrically and thermally conductive tube 313.

In a preferred embodiment and still referring to FIGS. 15A and 15B, the first and second electrically and thermally conductive tubes 311 and 313 are silver and are available from Otto Frei, Oakland Calif. in the form of Sterling Silver tubes containing at least 92.5% silver. The first and second electrically insulative sleeves 310 and 312 are preferably thin-walled polyimide tubes available from Vention Medical located in Marlborough, Mass. and other locations in the U.S. The first and second electrically insulative coverings sleeves 318 and 319 are preferably applied in the form of thin-walled polymeric shrink tubing available from Vention Medical located in Marlborough, Mass. and other locations in the U.S.

Figure 19:
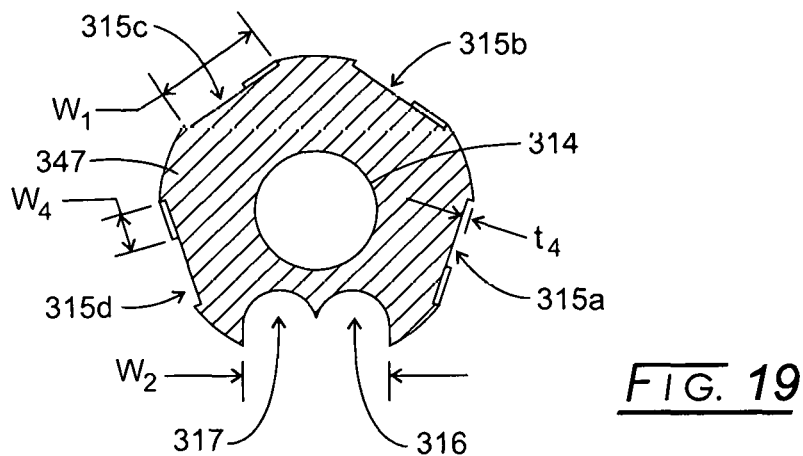
FIG. 19 is an end sectional view of leaf and tube support member seen in FIG. 20.
Figure 19A:
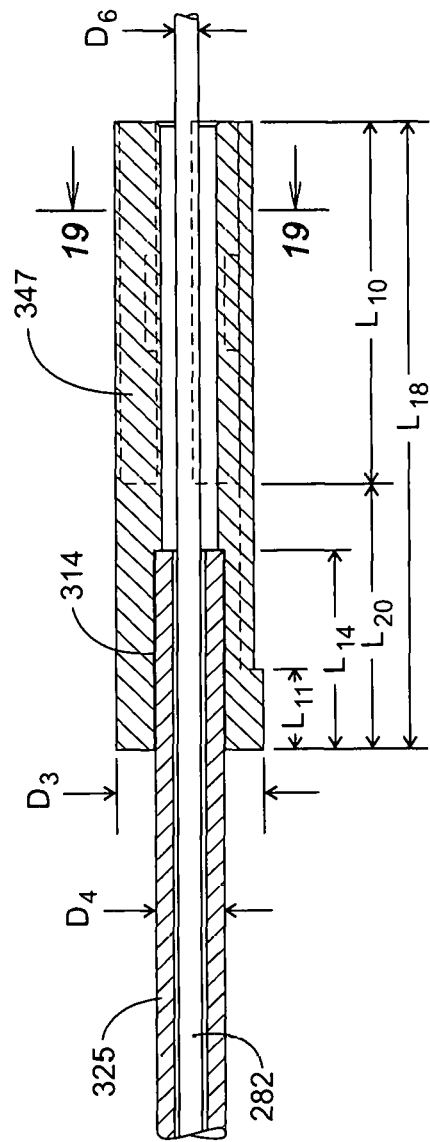
FIG. 19A is a partial side sectional view of leaf and tube support member, drive tube and support tube seen in FIGS. 20 and 21.

The components of the leaf member and tube assembly 400 are shown in greater detail in FIGS. 19, 19A and 20 including dimension references, as noted. Turning first to FIGS. 19 and 19A, a leaf and tube support member 347 is shown in both end and side cross-sectional views. The end cross-sectional view in FIG. 19 reveals drive tube cavity 314, four leaf member support cavities 315a-315d as well as first and second electrically and thermally conductive tube support cavities 316 and 317. The side cross-sectional view in FIG. 19A reveals drive tube cavity 314 and inserted drive tube 325 that is adhesively affixed to leaf and support member 347 (e.g., adhesively bonded using cyanoacrylate adhesive). The side cross-sectional view in FIG. 19A also reveals support tube 282 located inside drive tube 325 that extends from the proximal end of disposable support housing 100 to the guidance assembly 267 at the distal end of delivery cannula 22. A perspective view seen in FIG. 20 of leaf member and tube assembly 400 reveals four leaf members 348a-348d and two electrically and thermally conductive tubes 311 and 313 affixed to the leaf and tube support member 347 by adhesive bonding the leaf members 348a-348d and tubes 311 and 313 to the surfaces of their respective cavities 315a-315d, 316 and 317 (e.g., adhesively bonded using cyanoacrylate adhesive). In addition to and after the adhesive bonding step, the full length, L13 of leaf and tube support member 347 is covered with shrink tubing which serves to further secure the attachment of the leaf members and tubes to leaf and tube support member 347. The leaf member and tube assembly 400, as seen in FIG. 20, is slideably positioned inside delivery cannula 22 with the distal end of leaf member and tube assembly 400 registered with leaf and tube paths and ramps located within guidance assembly 267 seen earlier in FIG. 12.

Figure 21:
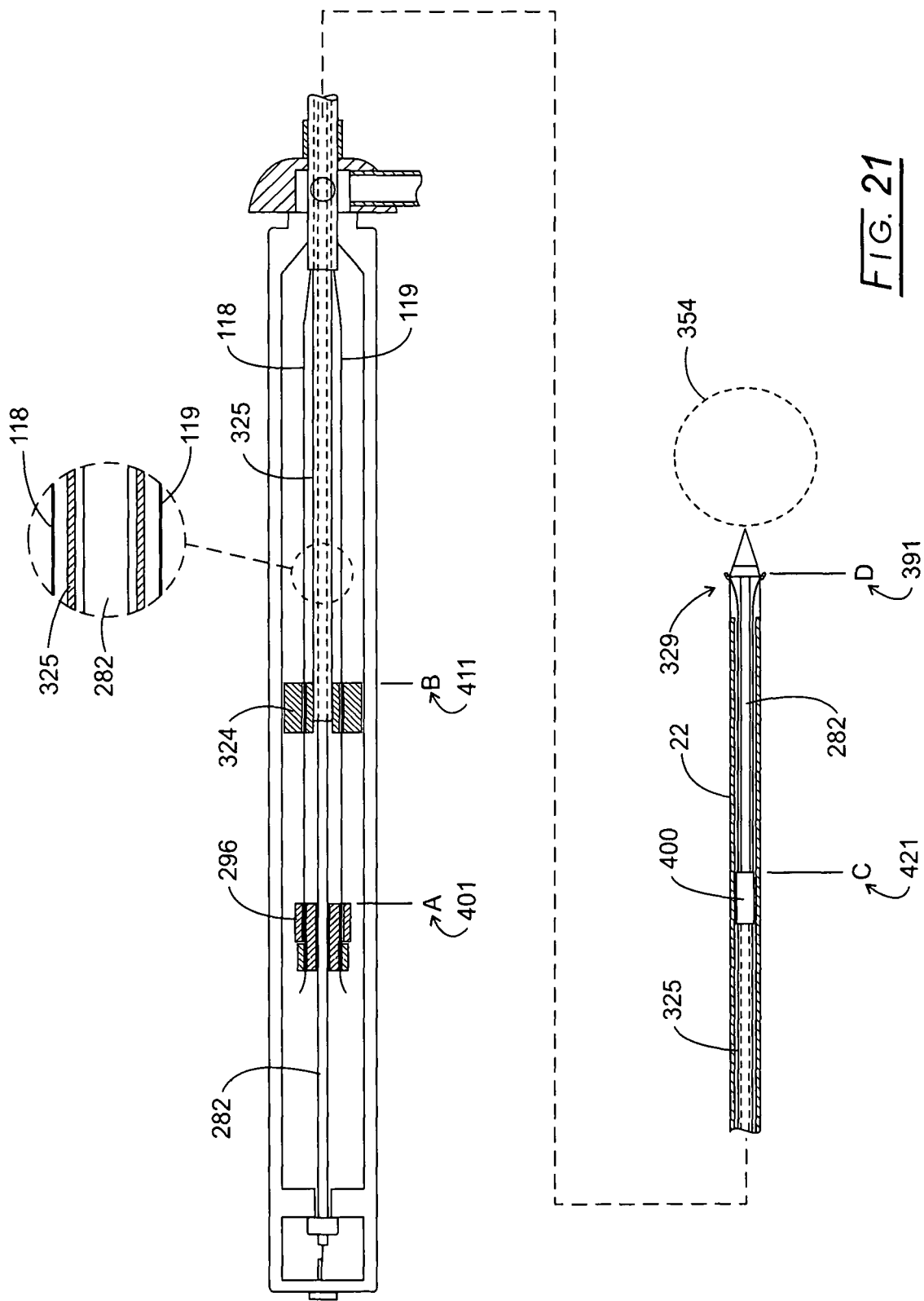
FIG. 21 is a sectional view of disposable tissue capture device seen in FIG. 2 showing positions of drive assembly drive member, cable mounting hub, leaf member and tube assembly prior to start of tissue cutting and capture.

Referring to FIG. 21, a partial sectional view presented in connection with FIG. 8 is reproduced wherein the cable mounting hub 296, drive assembly drive member 324 as well as leaf member and tube assembly 400 are shown in their initial positions A, B and C as seen at 401, 411 and 421, respectively. The initial positions A, B and C correspond to the positions of these component prior to the start of tissue cutting and capture after the tissue cutting and capture assembly 329 has been positioned adjacent to targeted tissue volume 354.

Figure 22:
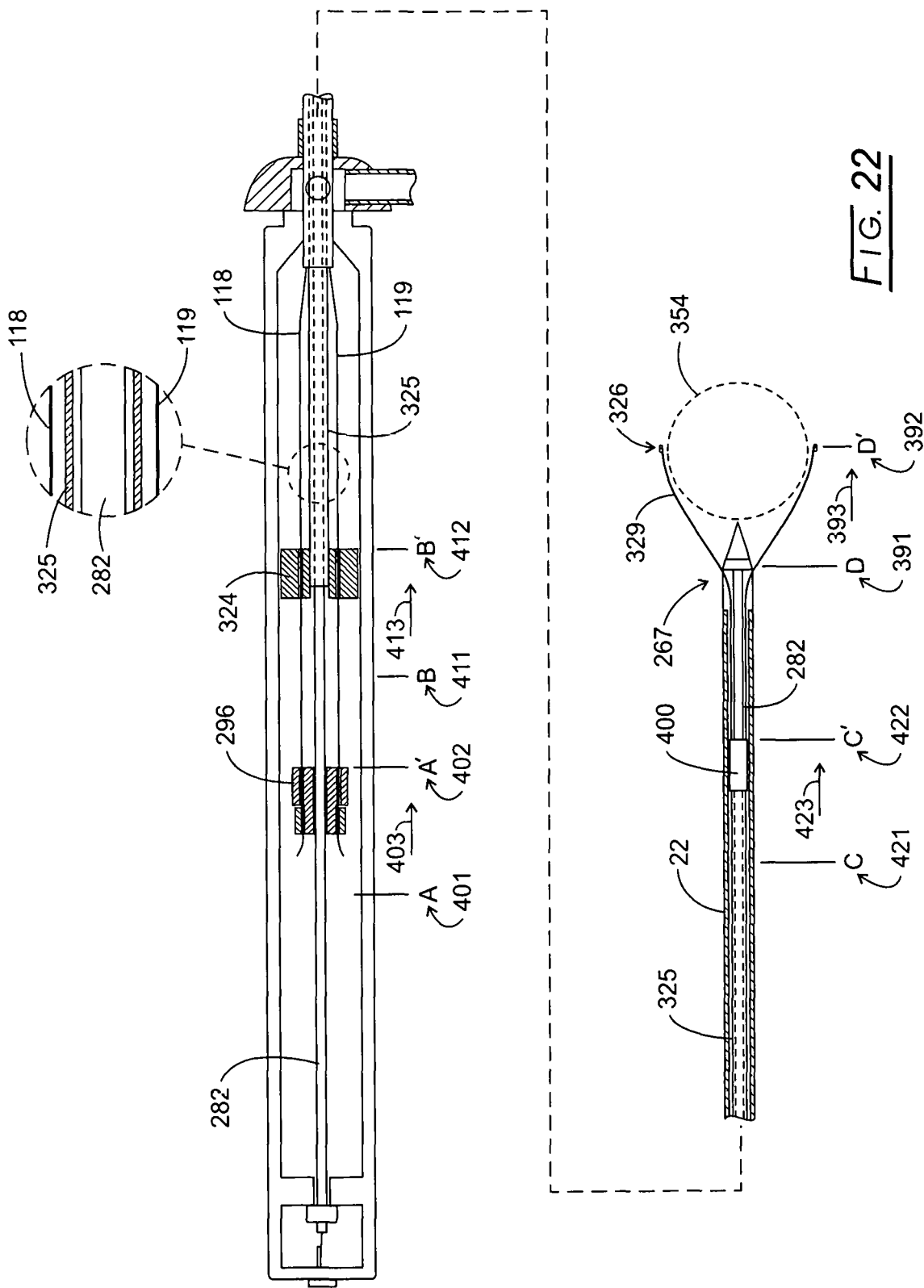
FIG. 22 is a sectional view of disposable tissue capture device seen in FIG. 2 showing positions of drive assembly drive member, cable mounting hub, leaf member and tube assembly after start of tissue cutting and capture at point of maximum opening of tissue cutting and capture assembly.

Referring next to FIG. 22, a partial sectional view presented in connection with FIG. 8 is reproduced wherein, following commencement of the tissue cutting and capture process as described above, capture advancement yoke 185 advances the position of the drive assembly drive member 324 from position B to position B' as seen at 411 and 412 in the direction indicated by first movement direction of drive assembly drive member 324 as seen at arrow 413. The advancement of the position of the drive assembly drive member 324 from position B to position B' as seen at 411 and 412 and associated advancement of drive tube 325 induces the advancement of leaf member and tube assembly 400 from position C to position C' as seen at 421 and 422 indicated by first movement direction of leaf member and tube assembly 400 as seen at arrow 423. In addition, the advancement of the position of the drive assembly drive member 324 from position B to position B' as seen at 411 and 412 induces the advancement of the cable mounting hub 296 from position A to A' as seen at 401 and 402 as indicated by first movement direction of cable mounting hub 403 as a result of the associated advancement of the resistively heated portion of the electrically conductive cutting and pursing cable 309 connected to the distal ends of tissue cutting and capture assembly 329 and the associated first and second tensionable portions of the cutting and pursing cables 118 and 119. Advancement of cable mounting hub 296 to position A' corresponds to the first and second pursing actuation ears 124 and 128 of cable mounting hub 296 advancing into direct contact with pursing actuation yoke 184 as seen in FIG. 4.

Still referring to FIG. 22, tissue cutting and capture assembly 329 has advanced from it its initial position D within guidance assembly 267 to a partially deployed tissue capture basket 326 at a position D' representing the maximum opening of the tissue cutting and capture assembly 329 as seen at 391 and 392 indicated by first movement direction of eyelet containing tip 330 (not shown) of leaf member 348 (not shown) as seen at arrow 393.

Referring now to FIGS. 3, 4 and 22, at the position in which the first and second pursing actuation ears 124 and 128 of cable mounting hub 296 have advanced into direct contact with pursing actuation yoke 184, the tension in the associated first and second tensionable portions of the cutting and pursing cables 118 and 119 increases. The increase in the tension in the associated first and second tensionable portions of the cutting and pursing cables 118 and 119 thereby increases the mechanical load on the drive assembly drive member 324 and, correspondingly, the level of the electrical current delivered to the second motor 171a. As described in connection with FIGS. 3 and 4, second motor 171a in second motor-actuated drive tube drive member translation assembly 181 functions to advance capture advancement yoke 185 in a forward direction during the tissue capture process. As the capture advancement yoke 185 is driven forward by second motor 171a, it urges the forward advancement of the drive assembly drive member 324. The increase in the electrical current delivered to second motor 171a at the moment the cable mounting hub 296 contacts the stationary pursing actuation yoke 184 and associated increase in the electrical current delivered to second motor 171a signals the sensing and control circuitry in control assembly 66 to apply a predetermined level and polarity of direct current (DC) voltage to first motor 170a in first motor-actuated cable mounting hub translation assembly 180. Upon the application of a predetermined level and polarity of DC voltage to first motor 170a, pursing actuation yoke 184 is driven in a rearward direction thereby retracting the position of cable mounting hub from position A' to A" as seen at 402 and 404 in the direction indicated by second movement direction of cable mounting hub 296 as seen at arrow 405.

Figure 23:
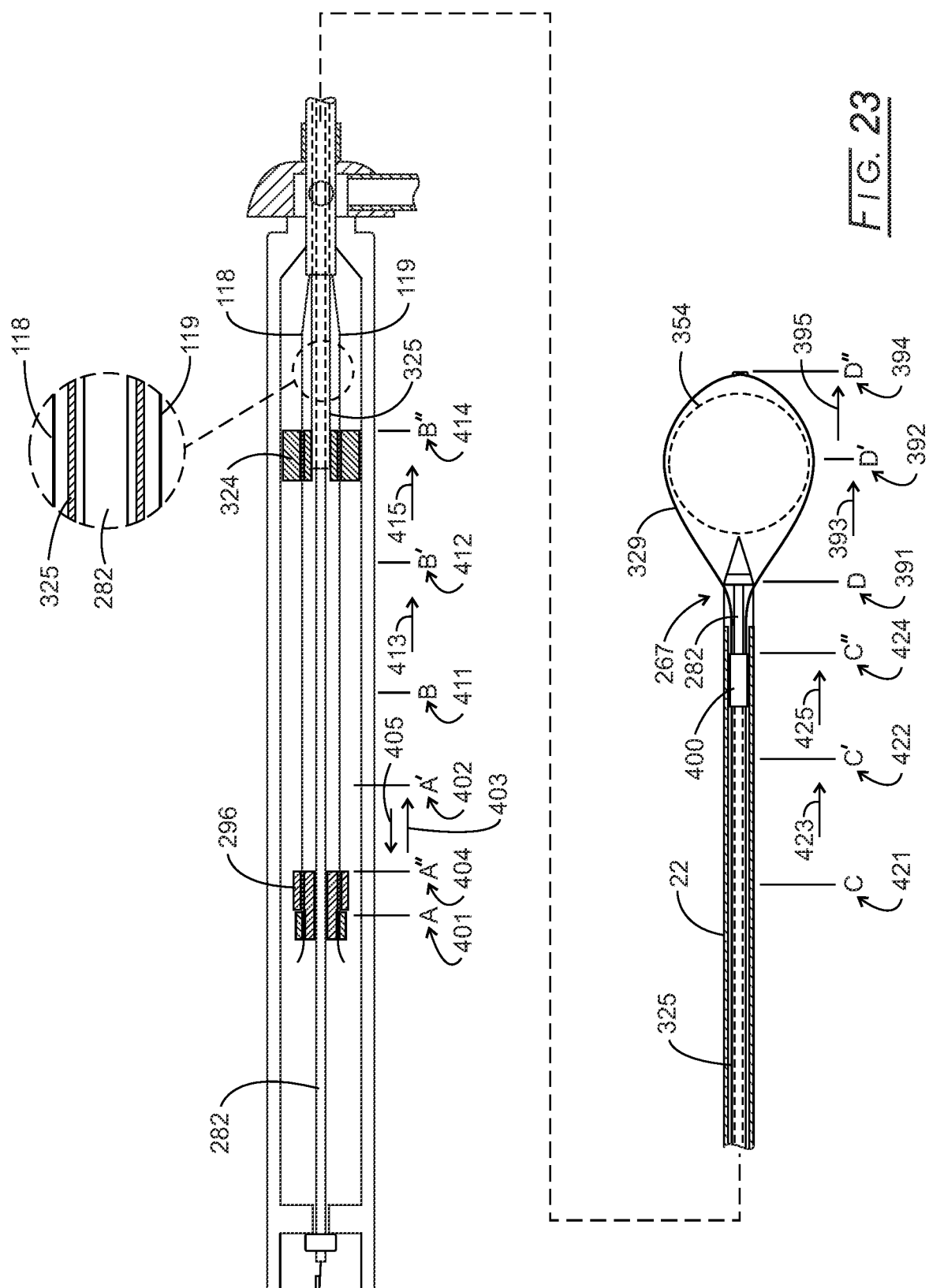
FIG. 23 is a section view of disposable tissue capture device seen in FIG. 2 showing positions of drive assembly drive member, cable mounting hub, leaf member and tube assembly at the completion of tissue cutting and capture.

Referring finally to FIGS. 3, 4 and 23, a partial sectional view presented in connection with FIG. 8 is reproduced wherein, following attainment of the maximum opening of the tissue cutting and capture assembly 329, capture advancement yoke 185 continues to advance the position of the drive assembly drive member 324 from position B' to position B" as seen at 412 and 414 in the direction indicated by second movement direction of drive assembly drive member 324 as seen at arrow 415. Once the maximum opening of the capture basket has been attained as seen at position D' in FIG. 22, a predetermined DC voltage and polarity is simultaneously applied to first motor 170a to advance the pursing actuation yoke 184 in a rearward direction thereby increasing the rate at which the resistively heated portion of electrically conductive cutting and pursing cable 309 purses down to complete the capture of targeted tissue volume 354 by tissue cutting and capture assembly 329 at position D" as seen at 394.

As described earlier, the attainment of the complete pursing down and closure of the tissue cutting and capture assembly 329 seen in FIG. 23 results in a further increase in the current level, IMOTOR2 delivered to the second motor 171a. Referring now to FIGS. 1, 4 and 23, when the current level, IMOTOR2 delivered to the second motor 171a, as measured by sensing and control circuitry within control assembly 66, exceeds a predetermined "stall" current level, ISTALL, the constant current delivered to the resistively heated portion of electrically conductive cutting and pursing cable 309 is discontinued and the capture complete icon 52 on the front panel of control assembly 66 is illuminated. Also, the audible tone that was being generated by control assembly 66 to alert the operator that constant current was being applied to the resistively heated portion of electrically conductive cutting and pursing cable 309 during the tissue cutting and capture procedure is now discontinued.

Returning to FIGS. 1, 2, 3 and 4, operator removes tissue incision and retrieval instrument 12 from the body of the patient. After positioning the tissue cutting and capture assembly 329 over a suitable tissue specimen collection container (not shown), tissue release switch 54 located at front panel of control assembly 66 is depressed and tissue release icon 56 on front panel of control assembly 66 is illuminated. Upon depressing tissue release switch, a predetermined voltage of reverse polarity is applied to second motor 171a for a predetermined time period (e.g., 5 seconds), causing second motor-actuated drive tube drive member translation assembly 181 to retract capture advancement yoke 185. As capture advancement yoke 185 is retracted in a rearward direction, the distal driving surface 227b of capture advancement yoke 185 contacts first and second capture advancement ears 134 and 136 of capture advancement yoke 185 to urge capture advancement yoke 185 in a rearward direction. Due to the mechanical attachment afforded by the drive tube 325 whose distal ends are adhesively bonded to the drive assembly drive member 324 and the leaf member and tube assembly 400, the retraction of the drive assembly drive member 324 to the point at which the tissue capture basket is approximately at position D' (see FIG. 22) enables the removal of the captured targeted tissue volume 354 from tissue cutting and capture assembly 329. Alternatively, a scissors or other cutting device may be used to cut the resistively heated portion of electrically conductive cutting and pursing cable 309 thereby allowing the leaf members to open and release the captured targeted tissue volume 354 from tissue cutting and capture assembly 329.

In addition to the example dimensions specified earlier in connection with FIGS. 18-18C, the range of preferred dimensions for the various components seen in FIGS. 4-20 are listed below where all dimensions are in units of inches and are label as shown in the referenced figures.

L10=0.4 to 1.0
L11=0.3 to 0.6
L12=2.0 to 4.0
L13=2.0 to 4.0
L14=0.25 to 0.50
L15=10.0 to 14.0
L16=8.0 to 13.0
L17=3.5 to 6.0
L18=0.8 to 2.0
L19=0.025 to 0.100
L20=0.3 to 1.7
H1=1.25 to 2.50
D1=0.20 to 0.35
D2=0.4 to 1.2
D3=0.20 to 0.35
D4=0.08 to 0.15
D5=0.011 to 0.020
D6=0.07 to 0.13
D7=0.60 to 1.00
D8=0.0.025 to 0.100
W1=0.055 to 0.105
W2=0.090 to 0.130
W3=0.05 to 0.10
W4=0.020 to 0.030
W5=0.8 to 2.0
W6=0.020 to 0.040
t1=0.002 to 0.007
t2=0.0005 to 0.0020
t3=0.0005 to 0.0020
t4=0.002 to 0.007

Figure 24:
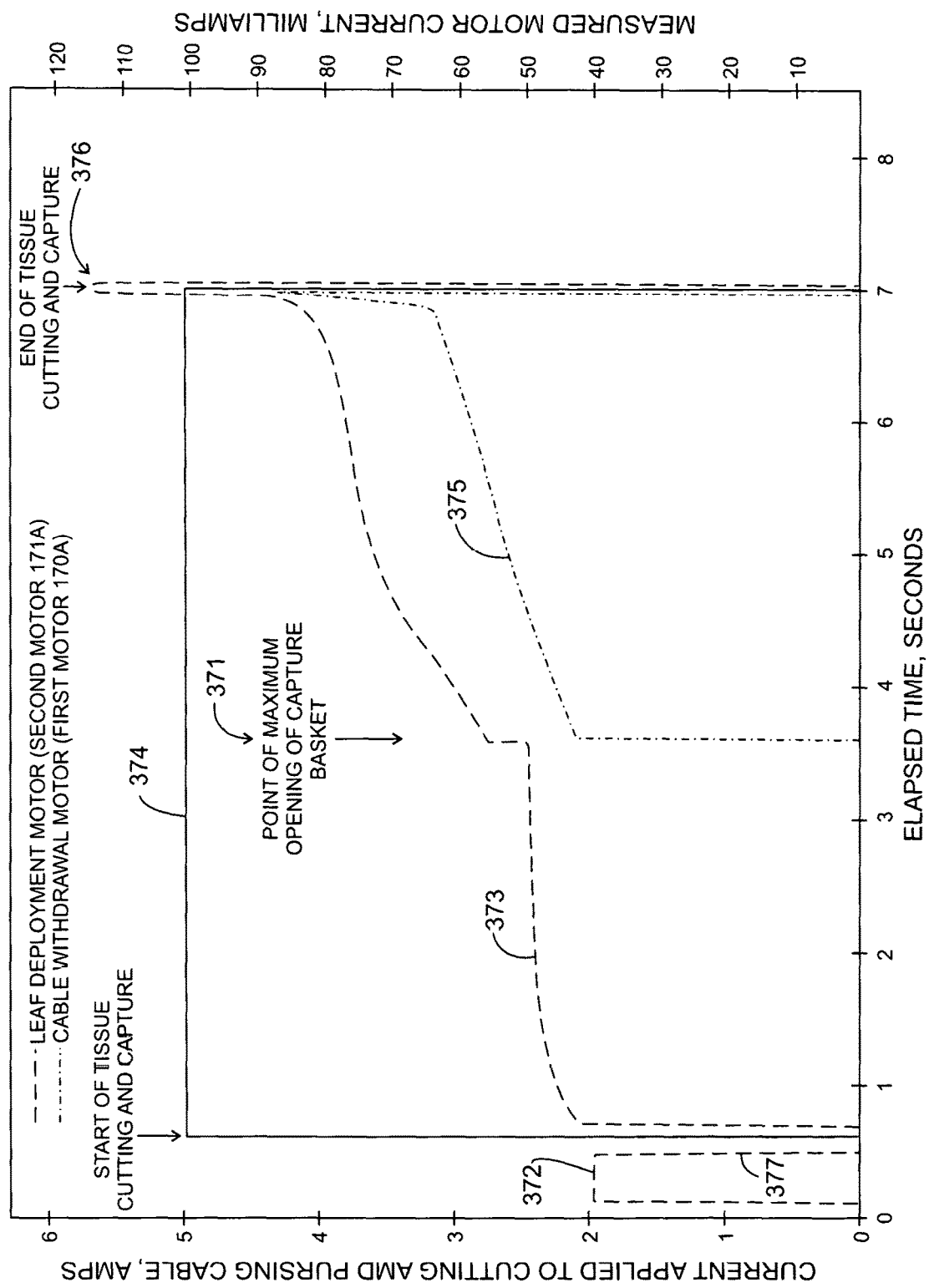
FIG. 24 is a graph relating time with level of applied constant current to resistively heated portion of electrically conductive cutting and capture cable as well as levels of current delivered to first and second motors according to the invention.

Referring to FIGS. 1, 4 and 24, the performance of system 10 in connection with the capture of a targeted tissue volume 354 is portrayed. In FIG. 24, the level of constant current applied to resistively heated portion of electrically conductive cutting and pursing cable 309 (left ordinate) is plotted with respect to elapsed time (abscissa). In addition, measured level of current delivered to first and second motors 170a and 171a, respectively (right ordinate) are also plotted with respect to time. Turning first to measured level of current delivered to second motor 171a, voltage is briefly applied to second motor to return capture advancement yoke to the initial or "home" position as seen in FIG. 4. Immediately following initialization and verification that the current level applied to second motor, 171a is within a predetermined range during initialization, constant current is applied to those portions of the resistively heated portion of electrically conductive cutting and pursing cable located forward of first and second electrically and thermally conducting tubes 311 and 313 and in contact with tissue. About 0.01 to 0.10 seconds after the application of a predetermined level of constant current, a predetermined voltage level is applied to second motor 171a as represented by line 373 in FIG. 24.

At the point in time when the cable mounting hub 296 contacts the stationary pursing actuation yoke, the measured level of motor current delivered to second motor 171a abruptly increases as seen at 371 in FIG. 24 corresponding to the point of maximum opening of the tissue cutting and capture assembly 329. At this point in time, a predetermined level of voltage is applied to first motor 170a to initiate the retraction of the cable mounting hub 296 to increase the rate at which the tissue cutting and capture assembly 329 purses down to more closely approximate the preferred spherical like shape at the distal half of the tissue cutting and capture assembly 329. At the completion of the pursing down and closure of the tissue cutting and capture assembly 329, the tensile load on the resistively heated portion of electrically conductive cutting and pursing cable 309 abruptly increases further as seen at 376. At this point, the applied constant current is immediately discontinued as well as the voltage levels applied to the first and second motors 170a and 171a, respectively indicating the completion of the tissue cutting and capture process as displayed on the front panel of the control assembly 66 at capture complete icon 52.

In an alternative embodiment, the sensing of motor current level supplied to second motor 171a in order to detect the instant at which the cable mounting hub 296 contacts the stationary pursing actuation yoke, as described in the previous paragraph, is replaced with the detection of the elapsed time between [a] the start of the advancement of the distal ends of the leaf members 348a-348d and supported resistively heated portion of electrically conductive cutting and pursing cable 309 (as seen in FIG. 18) and [b] the attainment of the operator-selected maximum opening diameter, D2 of the distal ends of the leaf members 348a-348d and supported, circumscribing resistively heated portion of electrically conductive cutting and pursing cable 309 (as seen in FIG. 18A). As seen in FIG. 1, the operator selects the maximum diameter, D2 of the tissue specimen to be excised using the increase maximum capture diameter selector button 36 or decrease maximum capture diameter selector button 38 on front panel of control assembly 66. The operator-selected maximum capture diameter, D2 is indicated at display 37 of control assembly 66. Since the rate of advancement of the leaf members 348a-348d is accurately controlled by the voltage level applied to second motor 171a, then the maximum capture diameter, D2 corresponds to a single corresponding elapsed time to reach the maximum opening.

Once this elapsed time has been reached, corresponding to the operator-selected maximum capture diameter, D2 (e.g., 25 mm) and referring to FIGS. 4, 8, 18A, 18B and 18C, a predetermined DC voltage of the appropriate polarity is applied to first motor 170a to initiate the pursing down of the deployed tissue capture basket 326 by causing first motor 170a to advance rearwardly within the housing assembly 15. The higher the predetermined DC voltage applied to first motor 170a, the faster the rate of retraction of the pursing down of the deployed tissue capture basket 326 since the first and second proximal ends of the resistively heated portion of electrically conductive cutting and pursing cable are attached to cable mounting hub 296 being translated rearwardly by first motor and planetary gear assembly 170. The DC voltage level applied to first motor 170a is selected to enable the pursing down and closure of the deployed tissue capture basket 326 to preferably produce a nearly spherical capture diameter as seen in FIG. 18C wherein the single pursed down point 356 extends only a minimal distance beyond the targeted tissue volume 354. In contrast, if the rate of pursing down of the deployed tissue capture basket 326 is too slow, corresponding to a rate of retraction of the cable mounting hub 296 that is too slow, then the shape of the captured tissue specimen is undesirably elongated as seen in FIG. 18B.

The set of FIGS. 25A-25F combine, as labeled thereon, to provide a flow chart describing the operation of the instant system. In the discourse to follow, the term "handle" refers to tissue incision and retrieval instrument 12 comprising disposable tissue capture device 101 and reusable housing 14 as seen in FIGS. 1 and 2. In the discourse to follow, the term "controller" refers to control assembly 66 as seen in FIG. 1. Cueing icons representing given switch functions, test results or operational modes are provided, where appropriate adjacent switches appear on the front panel control assembly 66. Looking to FIGS. 1 and 25A, the procedure starts as represented at block 472 and line 473 providing for the connection of multi-lead connector 30 of multi-lead cable 29 to connector receptacle 32 at front panel of control assembly 66. Next, as represented at block 474 and line 476 control assembly 66 is turned on by actuating front panel on/off switch 58. In this regard, an interlock current is caused to pass through a coding resistor (e.g., 10,000 ohm resistor) present in the instrument 12 housing assembly 14. If the test for this interlock connection is passed, then the green LED 33, above the control assembly cable connector 32 will be illuminated represented by the query posed at block 478. If LED 33 is not energized, then the procedure reverts as indicated at line 480 and block 482, the practitioner being pre-instructed to check for a proper handle (housing assembly 14) connection and if that connection is proper, then the instrument 12 is replaced. For either of these improper conditions, the procedure loops to commencement block 472 as represented at lines 1484 and 486. Where the query posed at block 478 indicates that proper handle (housing assembly 14) connection is present and the green LED 33 is illuminated, then the procedure continues as represented at line 488 and block 490.

Still referring to FIGS. 1, 25A as well as FIG. 4, block 490 calls for an actuation of the "Initialize" switch 40 located on the front panel of control assembly 66. This causes second motor 171a to be energized in a reverse sense to cause the rotation of second lead screw 177 and the driving of second motor-actuated drive tube drive member translation assembly 181 rearwardly until the second translation nut 183 engages surface of bulkhead 163. As represented at line 492 and block 494, a determination is made as to whether the green LED behind the Initialize icon display 42 at the front panel of control assembly 66 is illuminated. Where that Initialize icon display 42 is not illuminated, the activity described at block 490 failed and the procedure reverts as represented at line 496 and block 498, the practitioner having been pre-instructed that a faulty cable or "handle" is at hand and the procedure reverts to starting block 472 as represented at lines 500 and 486. A failure to pass this test results in the flashing of red LED behind the Initialize icon display 42, generation of a pulsing sound output, and the procedure is halted.

Referring now to FIGS. 1, 2, 3, 4, 21, 22 and 25A, if the query posed at block 494 results in an affirmative determination with the illumination of the noted green LED behind the Initialize icon display 42, then, as represented at line 502 and block 504, the practitioner inserts the disposable tissue capture device 101 into the reusable housing 14. Proper insertion is assured inasmuch as disposable tissue capture device 101 cannot be inserted within the reusable housing 14 to create housing assembly 15 unless the first and second capture advancement ears 134 and 136 are aligned for slideable insertion within slot 229 located in both arms of capture advancement yoke 185 (See FIG. 4). Practitioner next selects maximum effective diametric extent of capture of intended targeted tissue volume 354 by depressing increase capture diameter selection button 36 or by depressing decrease capture diameter selection button 38 on front panel of control assembly 66 until desired maximum diametric extent of intended capture of targeted tissue volume 354 is seen at display 37 on front panel of control assembly 66. The selection of the maximum effective diametric extent of capture of intended targeted tissue volume 354 by the practitioner causes the first lead screw driven by motor 170a to position pursing actuation yoke 184 at the precise location that will determine the maximum diametric effective extent of capture of the intended targeted tissue volume 354 as the forward movement of cable mounting hub 296 can not extend beyond the position of pursing actuation yoke 184. Hence, further forward translation of the tissue cutting and capture assembly 329 by second motor-actuated drive tube drive member translation assembly 181 initiates the pursing down of tissue cutting and capture assembly 329 as seen at position D' in FIG. 22.

Practitioner selection is made with respect to the predetermined size of the tissue volume to be removed. In general, the resistively heated portion of electrically conductive cutting and pursing cable and leaf members will extend through healthy tissue surrounding a targeted lesion. By way of example, if the diametric extent of targeted lesion is determined to be 10 mm (0.4 inch) based on prior examination using ultrasound and/or radiographic imaging, then practitioner may select a capture size of 20 mm (0.8 inch) to provide a boundary of healthy tissue surrounding the targeted lesion. This selection of a larger capture size will avoid seeding complications and the like upon removal of the biological specimen. Also, the verification of the presence of healthy tissue around the entire periphery of the targeted lesion, as determined at pathological examination of the excised tissue sample, represents the complete removal of the targeted lesion and may avoid the need for further surgical removal of tissue at the site of the excised targeted lesion.

Figure 25B:
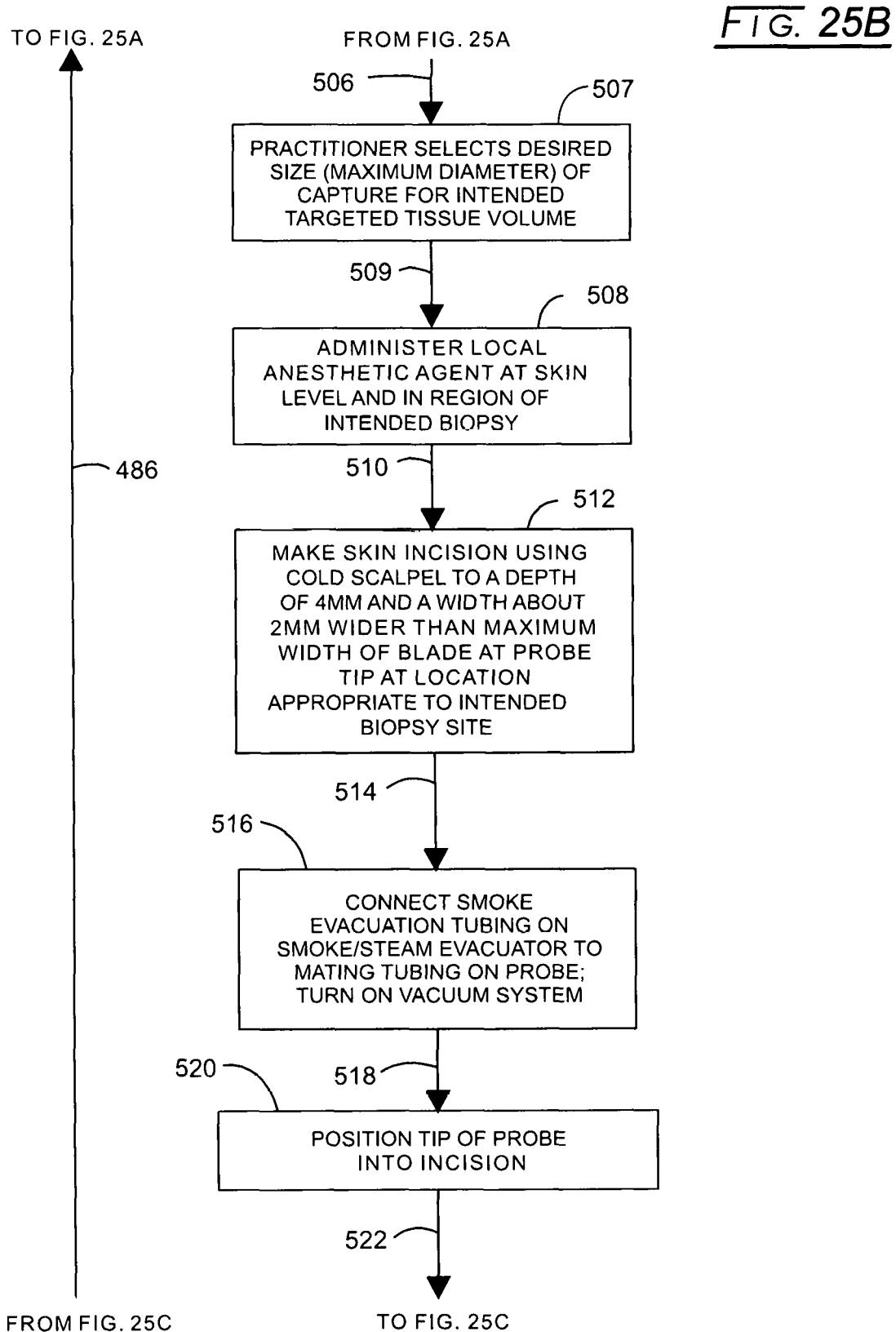

Referring now to FIGS. 1 and 25B, the program continues as represented at line 506 and block 508 providing for the administration of a local anesthetic at the skin level in the region of the intended biopsy. This step is performed several minutes before a skin incision is made to commence positioning of tissue retrieval instrument 12. For example, this step should be performed at least five minutes before the start of the biopsy procedure to assure perfusion of the target site with the anesthetic agent. Waiting periods of at least five minutes also avoids the entrapment of a bolus of anesthetic fluid along the path of the tissue cutting and capture procedure. Skin incision and the administration of a local anesthetic agent can optionally be performed prior to any of the previous steps. Following the administration of the anesthetic agent, as represented at line 510 and block 512, a cold scalpel is employed to make a skin incision to a depth of about 4 mm and a length approximately 2 mm wider than the maximum width of the forward region of the cannula 27. Then, as represented at line 514 and block 516, switch 67 of vacuum system 44 is turned on or optional vacuum system footswitch (not shown) is actuated. Next, as represented at line 518 and block 520 the forward region 27 of the delivery cannula 22 of the instrument 12 is positioned within the incision made in conjunction with block 512.

Figure 25C:
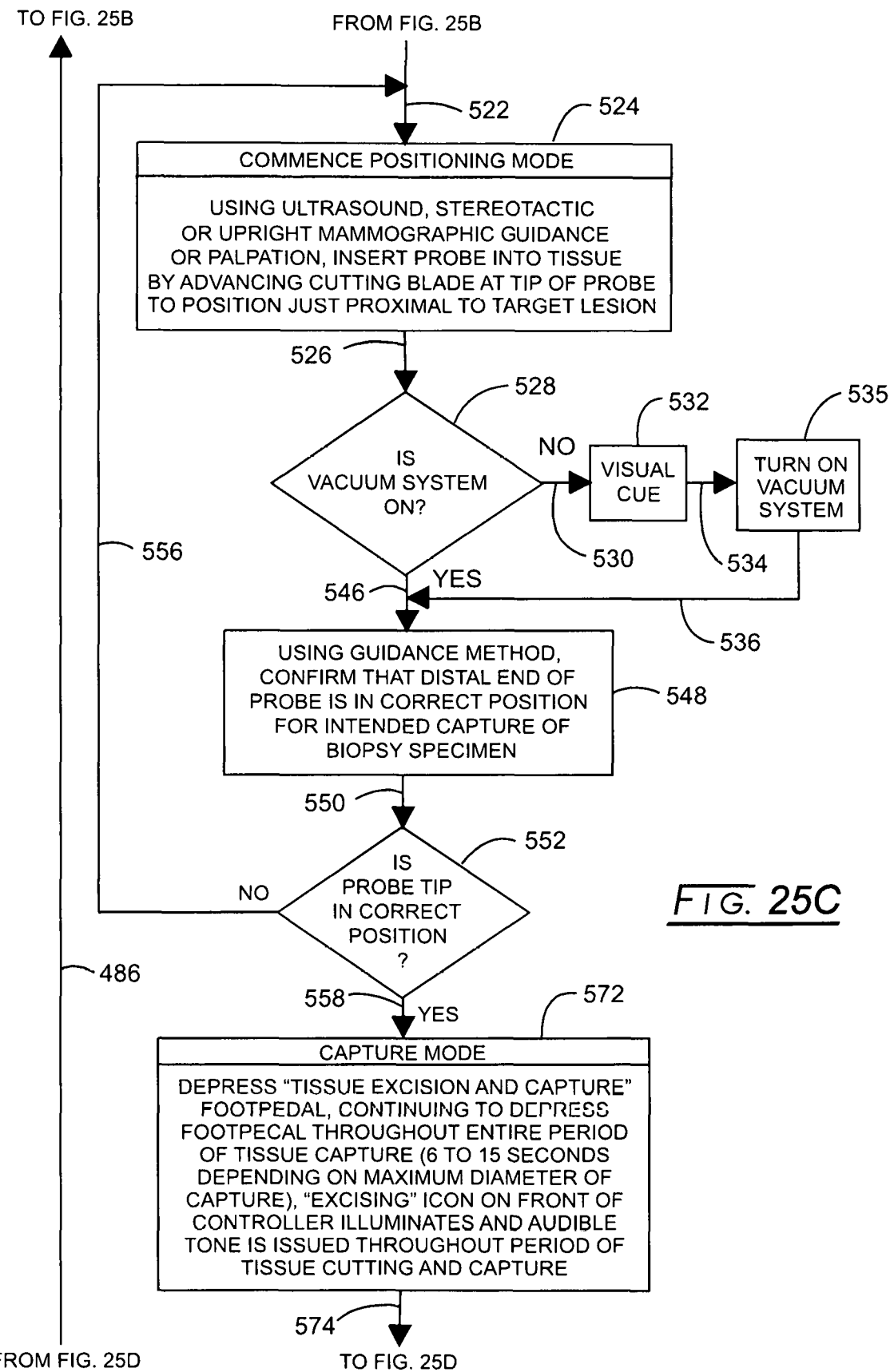

Referring now to FIGS. 1, 21 and 25C, the procedure then commences a positioning mode as represented at line 522 and block 524. During this mode, the practitioner, using ultrasound, stereotactic, upright mammography guidance or palpation advances the forward region 27 of delivery cannula 22 using surgically sharp blade 31 at tip of forward region 27 to a position in which the longitudinal axis of tissue retrieval instrument 12 is somewhat below (e.g., about 5 mm below) the center of the targeted lesion and the forward region 27 of the delivery cannula 22 is proximal to the targeted lesion as seen in FIG. 21. At this juncture in the procedure, the control assembly 66 carries out an interlock form of test to assure that the vacuum system 44 is indeed on and working. This test provides an assurance that steam will not migrate along the outer surface at delivery cannula 22. Accordingly, as represented at line 526 and block 528 a query is made as to whether the vacuum system is on. In general, this test is carried out in conjunction with a vacuum sensor within vacuum system 44 whose output is monitored by control assembly 66 through vacuum monitor cable 53 (FIG. 1). Where no vacuum is sensed, as represented at line 530 and block 532, the system turns on cueing LED and the procedure dwells as represented by line 534, until the vacuum system is activated as seen at block 535. Where the vacuum system is in proper order and activated, the procedure then continues as represented at line 536 and block 548.

At this juncture of the procedure and referring to FIGS. 1, 21 and 25D, the practitioner must be assured that the forward region 27 of the delivery cannula 22 is in proper position and orientation for carrying out a specimen capture. Accordingly, as represented at line 550 and block 552, a determination is made as to whether the forward region 27 of the delivery cannula 22 is in a correct position. If it is not, then as represented at lines 554 and 556, the procedure reverts to line 522 and the positioning mode represented at block 524.

Referring now to FIGS. 1 and 25D, where the forward region 27 of the delivery cannula 22 is in proper confronting adjacency with the targeted tissue volume 354, then as represented at line 558 and block 572, practitioner initiates the tissue capture mode by depressing footswitch 63 on footpedal assembly 61. Upon depressing footswitch 63, "Excising" icon 46 on front panel of control assembly 66 is illuminated and audible tone is issued by control assembly 66 throughout the entire period of tissue cutting and capture. If the practitioner needs to interrupt the tissue cutting and capture process for any reason, the practitioner releases footswitch 63 and the applied constant current to resistively heated portion of electrically conductive cutting and pursing cable 309 as well as the voltage applied to motors 170a and 171a is suspended until such time that practitioner resumes depressing footswitch 63.

Referring now to FIGS. 1, 24 and 25E, the entry into the tissue capture mode starts a three stage automated sequence. At stage one, second motor assembly 171a is briefly energized by the application of the predetermined voltage level for a period of about 0.3 second as described at to in connection with FIG. 24. This motor drive system integrity test assures that the motor drive assembly is performing properly before allowing the tissue cutting/capture sequence to commence. A control system within control assembly 66 monitors the current level delivered to second motor 171a during this brief period. Where the proper current levels are detected during this brief period as indicated by the example current level 372 seen in FIG. 24, then this capture mode test is satisfied. At stage two, second motor 171a will be de-energized and a predetermined level of constant current is applied to the resistively heated portion of electrically conductive cutting and pursing cable 309. At stage three, after a very brief delay (e.g., 0.1 to 0.2 second) following the initial and continuing application of constant current to resistively heated portion of electrically conductive cutting and pursing cable 309, a predetermined voltage level is applied to second motor 171a thereby commencing the start of the tissue cutting and capture of the targeted tissue volume 354.

Referring now to FIGS. 1, 22, 23, 24 and 25, at stage three, as described in conjunction with line 373 in FIG. 24, energized second motor 171a with simultaneous application of constant current to resistively heated portion of electrically conductive cutting and pursing cable 309 drive again is commenced to start tissue cutting and capture, an arrangement which continues until the pursing down of the resistively heated portion of electrically conductive cutting and pursing cable 309 is completed. During this interval of time, monitoring of current level delivered to second motor 171a continues as seen in line 373 of FIG. 24 and footswitch 63 is continuously actuated or depressed to maintain the capture mode as visually indicated by the illumination of the "Excising" icon 46 on the front panel of control assembly 66 and concurrent audible tone. The current level delivered to second motor 171a continues to be sensed during tissue capture. When monitored current level 373 reaches a first abrupt increase as indicated at time point 371 in FIG. 24 corresponding to contact of cable mounting hub 296 against stationary pursing actuation yoke 184, then the control system within control assembly 66 determines that the maximum opening of the tissue cutting and capture assembly 329 has been reached. As seen in FIG. 24, at the point in time 371 when the maximum opening of tissue cutting and capture assembly 329 has been reached, a predetermined voltage of reverse polarity is applied to motor 170a such that first transfer assembly and associated pursing actuation yoke 184 begins movement in a rearward direction to increase the rate of pursing down of the resistively heated portion of electrically conductive cutting and pursing cable 309 to achieve the desired configuration of tissue cutting and capture assembly 329 as seen in 18C and arrow 405 in FIG. 23.

Referring again to FIGS. 12, 18 and 25E, the initial test by second motor 171a is represented at line 574 and block 576 by energizing second motor 171a for a period of TIMESTART1 and is represented at line 578 and block 580. By way of example, time period TIMESTART1 may be in the range from 0.05 to 0.50 second and sufficiently long to assure that the distal ends of leaf members 348a-348d and distal ends of first and second electrically and thermally conductive tubes 311 and 313 are sufficiently advanced to assure that the supported resistively heated portion of electrically conductive cutting and pursing cable 309 is in direct contact with adjacent tissue and no longer in contact with confinement sleeve 264 and tip component 266. In addition to pre-positioning resistively heated portion of electrically conductive cutting and pursing cable 309 above the surfaces of confinement sleeve 264 and tip component 266 and in direct contact with tissue, where the current level test for second motor 171a during the noted brief test interval, TIMESTART1 fails, then as represented at line 582 and 584, all LEDs on the front of control assembly 66 commence to flash along with intermittent audible tone, as represented at line 586 and block 588 indicating that a handle and/or cable fault is at hand and the handle reusable housing assembly 15 should be replaced. The procedure then follows the path represented at line 486 to block 472 calling for a restart of the entire procedure. Where the current level test for second motor 171a, as represented at block 580, shows proper performance, second motor 171a is de-energized as represented at line 377 in FIG. 24. Correspondingly, as discussed in connection with line 374 in FIG. 24, the constant current source is turned on. That application of constant current and associated pre-heating of the exposed portions of the resistively heated portion of electrically conductive cutting and pursing cable 309 is applied for a pre-determined brief period, TIMESTART2 (e.g., about 0.01 to 0.1 second) before re-energizing second motor 171a as represented at line 590 and block 592. Commencement of timing of this brief time interval is represented at line 594 and block 596. Determination of the brief time interval, TIMESTART2 is made as represented at line 598, block 600 and loop line 602.

Referring now to FIGS. 24 and 25F, at the termination of this brief time interval, an affirmative determination is made as represented at line 604, which is seen to lead to block 606. At this point in the procedure, as described at dashed line 373 in FIG. 24, constant current is applied to resistively heated portion of electrically conductive cutting and capture cable 309, second motor 171a is energized to start the deployment of the leaf member and tube assembly 400, ears 134 and 136 being driven forwardly by yoke 185. This procedure normally continues with the earlier-noted monitoring of current level delivered to second motor 171a until capture is complete. However, should the current level delivered to second motor 171a fall below a predetermined threshold, then a fault condition is indicated and the procedure is halted. In this regard, loss of load related motor current levels is an indication of mechanical failure.

Referring to FIGS. 1, 24 and 25F, as represented at line 608 and block 610 the practitioner may encounter some reason for pausing this capture procedure. Accordingly, if an affirmative determination is made with respect to the query posed at block 610, then as represented at line 612 and block 614 a pause mode is entered. Releasing the previously depressed footswitch 63 enters this pause mode. The pause icon 50 is then illuminated on control assembly 66.

At such time as the practitioner is ready to resume the cutting capture procedure, footswitch 63 again is depressed returning to the capture mode. Accordingly, following a reactivation from a pause mode, as represented at lines 616, the capture mode is again underway as represented at line 608 and indicated visually by the illumination of "Excising" icon 46 on front panel of control assembly 66 as well as issuing continuous audible tone by control assembly 66. Where no pause mode is entered, then, as represented at line 618 and block 619A the control system looks for an abrupt increase in the current level of second motor 171a greater than a predetermined currently level, IMAXOPEN associated with the cable mounting hub 296 contacting the stationary pursing actuation yoke 184, indicating the maximum opening of the tissue cutting and capture assembly 329 as noted as the point in time 371 in FIG. 24 and represented by block 619A and line 619B. Where the current level delivered to second motor 171a exceeds IMAXOPEN, then a predetermined DC voltage and reverse polarity is applied to first motor 170a to begin the rearward movement of pursing actuation yoke 184 and associated retraction of cable mounting hub 296 as seen at block 619C and line 619D. The rearward movement of cable mounting hub 296 at a predetermined rate, in conjunction with the rate of deployment of the tissue cutting and capture assembly 329 by second motor 171a, increases the rate of closure of the tissue cutting and capture assembly 329 as seen earlier in FIG. 18C.

Referring to FIGS. 1, 24, and 25F, current level delivered to second motor 171a is continuously compared with a predetermined stall current level, ISTALL as seen at block 620. If current level delivered to second motor 171a is greater than ISTALL, then the tissue capture is complete as indicated by line 624 and block 626. If current level delivered to second motor 171a is not greater than ISTALL, then current level delivered to first motor 170a is continuously compared with a predetermined stall current level, ISTALL as seen in line 622 and block 623A. If current level delivered to first motor 170a is greater than ISTALL, then the tissue capture is complete as indicated by line 623C and block 626. If current level delivered to first motor 170a is not greater than ISTALL, then tissue cutting and pursing down of the tissue cutting and capture assembly 329 continues as seen by looping back line 623B.

Referring now to FIGS. 1, 23, 24 and 25F, upon such detection of a forward stall condition, as represented at block 626, a capture complete mode is entered, the capture of the target tissue or tissue volume being completed and the constant current applied to the resistively heated portion of electrically conductive cutting and pursing cable 309 as well as the voltage applied to first and second motors 170a and 171a are terminated as seen a time point 376 in FIG. 24. Also, capture complete icon 52 at front panel of control assembly 66 is illuminated.

Upon an affirmative determination that the stall condition has been reached by first or second motors 170a or 171a, as represented at block 620 and line 624 or at block 623A and line 623C, the practitioner removes the delivery cannula 22 from the patient by appropriate manipulation of housing assembly 14 as seen at line 634 and block 636. During this removal, some stretching of the tissue typically will be encountered with little or no disfigurement ensuing.

Next, as represented at line 638 and block 640, vacuum equipment is disconnected, plug 65 being inserted into steam/smoke evacuation connector 64 (FIG. 2). Then, as represented at line 642 and block 644, the practitioner retracts first and second capture advancement ears 134 and 136 by depressing tissue release switch 54 on front panel of control assembly 66. Upon depressing tissue release switch 54, tissue release icon 56 on front panel of control assembly 66 is illuminated and second motor-actuated drive tube drive member translation assembly 181 retracts capture advancement yoke 185 thereby causing retraction of first and second capture advancement ears 134 and 136 from a position D" to a position D' as seen in FIGS. 22 and 23 to establish a specimen access orientation with leaf members 348 and first and second electrically and thermally conducting tubes 311 and 313 as seen in FIG. 18A. That specimen access orientation resembles a cup or open basket as seen in FIG. 22. Then, as represented at line 646 and block 648, the captured tissue specimen is placed in a container with appropriate solution for transport and storage in preparation for examination by a pathologist. As represented at line 650 and block 652 the specimen is transported to a pathology laboratory.

An optional arrangement is represented at line 654 and block 656. The latter block provides for placing a radio-opaque and/or echogenic marker in the tissue at the site of the biopsy and verifying the position thereof using radiography or ultrasonography. Then, as represented at line 658 and block 660 the skin incision is closed using appropriate conventional closure techniques.

Alternatively, referring to FIGS. 25A-25F, the terms "handle" and "controller" could refer to the housing assembly 15 in FIG. 5A wherein all power sources, control and display functions provided by control assembly 66 of FIG. 1 are incorporated with housing assembly 15 as seen in FIG. 5A.

Since certain changes may be made in the above method, system and apparatus without departing from the scope of the present disclosure herein involved, it is intended that all matter contained in the above description or shown in the accompanying drawings shall be interpreted as illustrative and not in a limiting sense. For example, throughout the disclosure presented herein, the resistively heated portion of electrically conductive cutting and pursing cable 309 containing multiple strands could be replaced by a resistively heated portion of electrically conductive cutting and pursing wire comprising a single strand of metal (e.g., titanium or titanium alloy wire).

We claim:

1. Apparatus for retrieving a targeted tissue volume (354) of given peripheral extent, comprising:
   a delivery cannula (22) having an outer surface surmounting an interior channel and extending from a proximal end portion along a longitudinal axis (8) to a forward region (27) having a distal end positionable in confronting adjacency with the targeted tissue volume;
   a leaf member and tube assembly (400) positioned within the interior channel of the delivery cannula at the forward region of the delivery cannula having a forward portion extending to a forwardly disposed resistively heated portion of an electrically conductive cutting and pursing cable (309) wherein a passage of electrical current is only through those portions of the resistively heated portion of the electrically conductive cutting and pursing cable in direct contact with tissue to define a leading edge of the resistively heated portion of the electrically conductive cutting and pursing cable, a first tensionable portion of cutting and pursing cable (118) extending proximally from the resistively heated portion of the electrically conductive cutting and pursing cable into the interior channel of the delivery cannula and a second tensionable portion of a cutting and pursing cable (119) extending proximally from the resistively heated portion of the electrically conductive cutting and pursing cable into the interior channel of the delivery cannula, the leading edge of the forward portion of the resistively heated portion of the electrically conductive cutting and pursing cable being extendable from the delivery cannula laterally outwardly and forwardly toward an outer peripheral dimension of a deployed tissue capture basket (326) having a predetermined maximum peripheral diametric extent effective to provide a circumspective positioning about the targeted tissue volume and the leading edge of the forward portion of the resistively heated portion of the electrically conductive cutting and pursing cable extendable under a mechanical load required for pursing down of the deployed tissue capture basket appliable to the first tensionable portion of cutting and pursing cable (118) and the second tensionable portions of the cutting and pursing cable (119) to a capture orientation enveloping the targeted tissue volume;
   a disposable support housing (100) having forward and rearward portions and coupled in supporting relationship with the delivery cannula at the proximal end portion of the delivery cannula;
   a tissue cutting and capture assembly (329) extending from driving engagement with a drive assembly drive member (324) to a driven engagement portion in a housing assembly (15) and drivably movable along the delivery cannula longitudinal axis from an initial position (391) to a position of an eyelet (327) carried by tips of a plurality of leaf members (348) of the leaf member and tube assembly (400) and located at a tissue cutting and capture assembly position (394);
   a first motor-actuated cable mounting hub translation assembly (180);
   an actuator and control assembly having a capture advancement yoke (185) and drivingly engagable with the drive assembly drive member (324), the drive assembly drive member driven forwardly by a second motor-actuated drive tube drive member translation assembly (181); and
   the housing assembly including a terminal assembly comprising first and second electrical contacts (120, 122) oriented to make contact with corresponding first and second electrical terminals (186) and (188) disposed within a reusable housing (14) that selectively receives a controlled constant current at an elevated frequency and at a predetermined level, the constant current appliable to the resistively heated portion of the electrically conductive cutting and pursing cable (309), the tissue cutting and capture assembly (329) locatable from the initial position (391) of the eyelet containing tip (330) of each of the leaf members (348) and to a maximum opening position (392) of the tissue cutting and capture assembly (329) and whereat the resistively heated portion of the electrically conductive cutting and pursing cable (309) being pursable down to complete capture of the targeted tissue volume.

2. The apparatus of claim 1, wherein the actuator and control assembly comprises a cable terminator component or cable mounting hub (296) coupled with the first tensionable portion of cutting and pursing cable (118) and the second tensionable portions of the cutting and pursing cable (119) and a cable mounting hub and pursing actuation yoke (184) engagable therewith, the cable mounting hub (296) being drivingly movable by the first tensionable portion of cutting and pursing cable (118) and the second tensionable portions of cutting and pursing cables (119) along the delivery cannula longitudinal axis (8) in correspondence with the advancement of the drive assembly drive member (324), from an initial position (401) of cable mounting hub (296) into engagement with the cable mounting hub and pursing actuation yoke (184) to define a partially deployed tissue capture basket (326) at a position (392) representing the maximum opening of the tissue cutting and capture assembly (329) and to effect the subsequent pursing down of the deployed tissue capture basket (326) by the first motor-actuated cable mounting hub translation assembly (180) driven in a second movement direction (405) of the cable mounting hub (296), thereby applying a mechanical load or tension to the first tensionable portion of cutting and pursing cable (118) and the second tensionable portions of the cutting and pursing cables (119).

3. The apparatus of claim 2, wherein the cable mounting hub and pursing actuation yoke (184) attached to the first motor-actuated cable mounting hub translation assembly (180) functions as a stop, the pursing actuation yoke (184) prepositioned by an operator selection of maximum diametric extent of tissue cutting and capture assembly (329) using an increase capture diameter selector button (36) or a decrease capture diameter selector button (38) on a-front panel of control assembly (66).

4. The apparatus of claim 2, wherein first and second capture advancement ears (134, 136) affixed to the drive assembly drive member (324) extends outwardly from the disposable support housing (100) to an extent wherein they are abuttingly engagable in driven relationship with the second motor-actuated drive tube drive member translation assembly (181).

5. The apparatus of claim 4, wherein the first and second capture advancement ears (134, 136) are configured for hand grasping to carry out movement of the drive assembly drive member (324) from a capture position toward at the end of tissue cutting and capture (414) to the start orientation initial position (401) of the cable mounting hub (296).

6. The apparatus of claim 1, wherein the resistively heated portion of electrically conductive cutting and pursing cable (309) is a single strand of metal wire.

7. The apparatus of claim 6, wherein the metal wire is a single strand of stainless steel, nickel, nickel alloy, titanium or titanium alloy having a diameter of between about 0.002 to about 0.005 inch.

8. The apparatus of claim 1, including a sharp cutting blade assembly disposed at the forward region of cannula (27) of the delivery cannula (22) wherein tip of blade (31) is coincident with the longitudinal axis (8) and enables an initial positioning of cannula distal end (25) in a confronting adjacency with respect to the targeted tissue volume (354).

9. The apparatus of claim 1, wherein the resistively heated portion of electrically conductive cutting and pursing cable (309) comprises a multiple stainless steel strands, each strand having a diameter of between about 0.0008 to about 0.002 inch.

10. The apparatus of claim 1, further comprising:
an elongate support tube (282) extending within the delivery cannula along the longitudinal axis from the forward region of cannula (27) into the disposable support housing (100) and secured thereto adjacent the rearward portion of disposable support housing (100), wherein drive assembly drive member (324) is positioned over the support tube and the disposable support housing is located within the housing assembly (15), having the capture advancement yoke (185) and drivingly engagable with the drive assembly drive member (324) and engagable with the second motor-actuated drive tube drive member translation assembly (181) to move the tissue cutting and capture assembly (329) from the initial position (391) of eyelet containing tip (330) of leaf member (348) to the tissue cutting and capture assembly position (394) of eyelet containing tip (330) of leaf member (348) at the end of tissue cutting and capture.

11. The apparatus of claim 1, in which the actuator and control assembly comprises:
a cable mounting hub (296) mounted for movement upon a support tube (282) and coupled with first tensionable portion of cutting and pursing cable (118) and the second tensionable portions of cutting and pursing cable (119);
a cable mounting hub and pursing actuation yoke (184) at an initial setting of a stop position for cable mounting hub (296) and abuttingly engagable with the-cable mounting hub; and
the cable mounting hub being drivingly moveable by the first tensionable portion of cutting and pursing cable (118) and the second tensionable portions of cutting and pursing cable (119) from an initial position (401) of cable mounting hub along the longitudinal axis (8) into engagement with the cable mounting hub and pursing actuation yoke (184) at an initial setting of the stop position for cable mounting hub (296) to define the predetermined maximum peripheral diametric extent of the deployed tissue capture basket (326) effective to provide a circumspective positioning about the targeted tissue volume (354).

12. The apparatus of claim 11, wherein the delivery cannula (22), the tissue cutting and capture assembly (329), the support tube (282), the drive assembly drive member (324), the cable mounting hub (296), the cable mounting hub and pursing actuation yoke (184), cable stop member assembly and first and second electrical contacts (120,122) oriented to make contact with corresponding first and second electrical terminals (186, 188) disposed within reusable housing (14) are combined in operational association with the housing assembly (15) configured for operative association within a receiving cavity (166) of the reusable housing to provide a discrete removable component of a tissue incision and retrieval instrument (12).

13. The apparatus of claim 1, wherein the tissue cutting and capture assembly (329) has a leading edge and the tissue cutting and capture assembly (329) comprises:
the plurality of leaf members (348) defining a containment structure or cage, each leaf member of the plurality of leaf members (348) having an eyelet containing tip (330), a width and a thickness, a confinement sleeve (264) and tip component (266) that cooperate to provide a guidance assembly (267) fixed at the forward region of cannula (27) and configured to effect deployment of the leaf members (348) into tissue at an angle of attack, the leaf members having a width and a thickness of an extent effecting formation of a generally curvilinear cage periphery when a forward portion of the tissue cutting and capture assembly (329) is subsequently extended while the eyelet containing tip of each leaf member of the tissue cutting and capture assembly is drawn mutually inwardly toward the longitudinal axis (8) to define a curvilinear profile and to close the leading edge of the tissue cutting and capture assembly about the targeted tissue volume (354).

14. The apparatus of claim 13, wherein each leaf member (348) is formed of metal; and each leaf member includes an electrically insulative coating having a thickness in a range of about 0.00015 to about 0.0005 inch.

15. The apparatus of claim 14, wherein each leaf member (348) width is of an extent effective to provide extensional cage defining stable movement of the leafs members through the guidance assembly (267) along a plane extending through the longitudinal axis.

16. The apparatus of claim 15, wherein the eyelet containing tip (330) of each leaf member (348) incorporates an eyelet (327) apertures dimensioned to receive the resistively heated portion of the electrically conductive cutting and pursing cable (309) and enable its sliding movement through the eyelet of each leaf member;

the electrically conductive cutting and pursing cable extending from a first and second electrically and thermally conductive tubes (311, 313) and through the eyelet at the eyelet containing tip of each leaf member (348), the electrically conductive cutting and pursing cable functioning in two distinctly different modes depending on whether the electrically conductive cutting and pursing cable is proximal or distal to its point of electrical contact (390) at distal ends of the first and second electrically and thermally conductive tubes, a current flow path (399) proceeding along the length of first electrically and thermally conductive tube (311) until electrical contact is made at the point of electrical contact (390) with the resistively heated portion of electrically conductive cutting and pursing cable (309), the electrical contact enabling electrical current to commence to flow from first electrically and thermally conductive tube (311) and into the resistively heated portion of electrically conductive cutting and pursing cable (309) in that portion of cable distal to point of contact (397) that begins at transition boundary (396), the current flow path continuing through resistively heated portion of electrically conductive cutting and pursing cable (309) until it reaches the distal end of second electrically and thermally conductive tube (313);

those portions of electrically conductive cutting and pursing cable that are proximal to the points of electrical contact at the distal ends of first and second electrically and thermally conductive tubes having no electrical current flow and are referred to as the first and second tensionable portions (118, 119) of the electrically conductive cutting and pursing cable.

17. The apparatus of claim 1, wherein the delivery cannula (22) includes an evacuation channel connectable with a vacuum source and extending from the proximal end portion to a suction port at the forward region, and including an outwardly extending continuous steam migration block surrounding the delivery cannula adjacent the suction port.

18. The apparatus of claim 1, wherein the elevated frequency of the constant current source is in the range from 50 KHz to 100 KHz.

19. Apparatus for retrieving a targeted tissue volume (354) of given peripheral extent, comprising:

a delivery cannula (22) having an outer surface surmounting an interior channel and extending from a proximal end portion along a longitudinal axis (8) to a forward region of cannula (27) having a cannula distal end (25) positionable in confronting adjacency with a targeted tissue volume (354);

a tissue cutting and capture assembly (329) driven by a plurality of leaf members (348) within a leaf member and tube assembly (400) positioned within the delivery cannula interior channel, having a forward portion extending to a forwardly disposed resistively heated portion of an electrically conductive cutting and pursing cable (309) and being extendible toward an outer peripheral dimension effective for its circumscribing pathway around the targeted tissue volume peripheral extent when moved along the longitudinal axis as the leaf member and tube assembly (400) is deployed from the delivery cannula;

a disposable support housing (100) having forward and rearward portions and coupled in supporting relationship with the delivery cannula at the proximal end portion of the delivery cannula;

a first motor (170a);

a second motor (171a);

a first planetary gear (170b);

a second planetary gear (171b);

a first motor-actuated cable mounting hub translation assembly (180);

a first translation nut component (182);

a second translation nut component (183);

a first motor and planetary gear assembly (170); and a second motor and planetary gear assembly (171);

a drive assembly drive member (324) including a drive tube (325) extending from driving engagement with the leaf member and tube assembly (400) within the delivery cannula (22) interior channel within the disposable support housing (100), said drive assembly drive member (324) having first and second capture advancement ears (134, 136) fixed to the drive assembly drive member (324) in driving relationship, the drive assembly drive member (324) being movable along the longitudinal axis from an initial position (411) to a final position (414) at the end of tissue cutting and capture;

a second motor-actuated drive tube drive member translation assembly (181) within a housing assembly (15) including rotational second lead screw (177) located in parallel relationship with the drive assembly drive member, fixed for rotation at second circular opening (169) in second bulkhead (163) in the housing assembly and extending forwardly therefrom to a self-aligning second flexible bellows-shaped coupler (175) having a forward driving connection portion coupled therewith and an rearward driven connection portion;

the second motor and planetary gear assembly (171) having a rotational drive output coupled in driving relationship with the second flexible bellows-shaped coupler rearward driven connection portion, the second motor and planetary gear assembly being mounted in self-aligning confinement within the housing assembly (15), having non-rotational freedom of movement extending as second rectangular tab (235) from the second motor and planetary gear assembly and being actuatable to drive the rotational second lead screw from the second flexible bellows-shaped coupler;

a transfer assembly comprising the second translation nut component (183) and a capture advancement yoke (185) and mounted in driven relationship with the rotational second lead screw, the transfer assembly having an initial position and having an engaging portion comprising first and second driving surfaces (227a) and (227b) located on interior surfaces of slot (229) of the capture advancement yoke and engagable in driving relationship with the first and second capture advancement ears (134, 136) of the drive assembly drive member to effect movement of the drive assembly drive member along the longitudinal axis (8) when the second motor and planetary gear assembly (171) is actuated; and a terminal assembly comprising first and second electrical contacts (120, 122) oriented to make contact with corresponding first and second electrical terminals (186) and (188) disposed within a reusable housing (14) that selectively receive a controlled constant current at an elevated frequency and at a predetermined level, the constant current appliable to the resistively heated portion of the electrically conductive cutting and pursing cable, the tissue cutting and capture assembly (329) positionable from adjacent to the tissue volume (354), to a position of an eyelet containing leaf member being at a maximum opening of tissue cutting and capture assembly (329) and then to a position whereat the resistively heated portion of the electrically conductive cutting and pursing cable (309) is positionable at a final position (41) to complete the capture of targeted tissue volume (354).

20. The apparatus of claim 19, wherein the transfer assembly is movable by the rotational second lead screw (177) from an initial position toward a forward portion of the housing assembly (15) when the second motor and planetary gear assembly (171) is actuated, the transfer assembly movement following along the longitudinal axis (8) until a forward stall condition of the second motor and planetary gear assembly occurs.

21. The apparatus of claim 20, wherein the second motor and planetary gear assembly (171) is responsive to reverse its rotational drive output in the presence of the forward stall condition to effect the return of the transfer assembly to its initial position, being driven by the rotation of second lead screw (177).

22. The apparatus of claim 20, wherein the control assembly is responsive to provide the reverse input to the second motor when the motor load characteristic corresponds with the presence of the drive member at the capture position.

23. An apparatus for carrying out a procedure for retrieving a targeted tissue volume (354), comprising:
    a delivery cannula (22) having an outer surface surmounting an interior channel and extending from a proximal end portion along a longitudinal axis (8) to a forward region (27) having a distal end positionable in confronting adjacency with the targeted tissue volume (354);
    a leaf member and tube assembly (400) positioned within the interior channel of the delivery cannula at the forward region of cannula (27) having a forward portion extending to a forwardly disposed resistively heated portion of an electrically conductive cutting and pursing cable (309) wherein a passage of electrical current is only through those portions of the resistively heated portion of electrically conductive cutting and pursing cable (309) in direct contact with tissue to define a leading edge of the resistively heated portion of electrically conductive cutting and pursing cable, a first tensionable portion of cutting and pursing cable (118) extending proximally from the resistively heated portion of the electrically conductive cutting and pursing cable (309) into the interior channel of the delivery cannula and a second tensionable portion of cutting and pursing cable (119) extending proximally from the resistively heated portion of the electrically conductive cutting and pursing cable (309) into the interior channel of the delivery cannula, the leading edge of the forward portion of the resistively heated portion of electrically conductive cutting and pursing cable being extendable from the delivery cannula laterally outwardly and forwardly toward an outer peripheral dimension of a deployed tissue capture basket (326) having a predetermined maximum peripheral diametric extent effective to provide a circumspective positioning about the targeted tissue volume (354) and the leading edge of the forward portion of the resistively heated portion of electrically conductive cutting and pursing cable is configured to be extendable while a mechanical load or tension level required for the pursing down of the deployed tissue capture basket (326) is adapted to be applied to the first tensionable portion of cutting and pursing cable (118) and to the second tensionable portions of the cutting and pursing cable (119) to a capture orientation enveloping the targeted tissue volume (354);
    a disposable support housing (100) having forward and rearward portions and coupled in supporting relationship with the delivery cannula at the proximal end portion of the delivery cannula;
    the leaf member and tube assembly (400) comprising a plurality of leaf members, each leaf member having a tip, each tip having an eyelet;
    a tissue cutting and capture assembly (329) extending from driving engagement with a drive assembly drive member (324) to a driven engagement portion at a housing assembly (15) and drivably movable along the longitudinal axis from an initial position (391) to a position of eyelet containing tips of the plurality of leaf members at tissue cutting to a capture assembly position (394);
    a first motor-actuated cable mounting hub translation assembly (180);
    an actuator and control assembly having a capture advancement yoke (185) drivingly engagable with the drive assembly drive member (324), the drive assembly drive member drivable forward by a second motor-actuated drive tube drive member translation assembly (181);
    the housing assembly including a terminal assembly comprising first and second electrical contacts (120, 122) oriented to make contact with corresponding first and second electrical terminals (186) and (188) disposed within a reusable housing (14) that selectively receive a controlled constant current at an elevated frequency and at a predetermined level, the controlled constant current configured to be applied to the resistively heated portion of the electrically conductive cutting and pursing cable from the initial position of eyelet containing tip of leaf member (391), continuing as tissue cutting and capture assembly (329) to a position of the eyelet containing leaf members whereat a maximum opening of the tissue cutting and capture assembly (329) and to a position to complete the capture of the targeted tissue volume (354); and
    an externally located control assembly (66) connected to the reusable housing (14) by a multi-lead cable (29) at connector receptacle (32), connected to footpedal (61) by a footpedal cable (71) and incorporating:
    a controlled constant current source;
    first and second motor constant voltage sources; and
    a programmed microcomputer to enable response to a capture actuation switch disposed on the foot pedal, generate audible tones and activate display indicator lights and to a stop procedure when a capture complete state is attained.

24. The apparatus of claim 23, wherein the actuator and control assembly comprises a cable terminator component or cable mounting hub (296) coupled with the first tensionable portion of cutting and pursing cable (118) and the second tensionable portions of the cutting and pursing cable (119) and second tensionable portions of cutting and pursing cable (118, 119) and a cable mounting hub and pursing a actuation yoke (184) engagable therewith, the cable mounting hub (296) being drivingly movable by the first and second tensionable portions of cutting and pursing cable along the longitudinal axis (8) in correspondence with the advancement of the drive assembly drive member (324), from an initial position (401) of cable mounting hub (296) into engagement with the cable mounting hub and pursing actuation yoke (184) to define a partially deployed tissue capture basket (326) at a position (392) representing the maximum opening of the tissue cutting and capture assembly (329) and to effect the subsequent pursing down of the deployed tissue capture basket (326) by the first motor-actuated cable mounting hub translation assembly (180) driven in the second movement direction (405) of the cable mounting hub (296), thereby applying a mechanical load or tension to the first and second tensionable portions of cutting and pursing cable (118, 119).

25. The apparatus of claim 23, wherein the elevated frequency of the constant current source is in the range from 50 kHz to 100 KHz.

26. An apparatus for carrying out a procedure for retrieving a targeted tissue volume, comprising:
   a delivery cannula (22) having an outer surface surmounting an interior channel and extending from a proximal end portion along a longitudinal axis (8) to a forward region (27) having a distal end positionable in confronting adjacency with the targeted tissue volume (354);
   a leaf member and tube assembly (400) positioned within the interior channel of the delivery cannula at the forward region of cannula (27) having a forward portion extending to a forwardly disposed resistively heated portion of an electrically conductive cutting and pursing cable (309) wherein a passage of electrical current is only through those portions of the resistively heated portion of electrically conductive cutting and pursing cable (309) in direct contact with tissue to define a leading edge of the resistively heated portion of electrically conductive cutting and pursing cable, a first tensionable portion of cutting and pursing cable (118) extending proximally from the resistively heated portion of the electrically conductive cutting and pursing cable (309) into the interior channel of the delivery cannula and a second tensionable portion of cutting and pursing cable (119) extending proximally from the resistively heated portion of the electrically conductive cutting and pursing cable (309) into the interior channel of the delivery cannula, the leading edge of the forward portion of the resistively heated portion of electrically conductive cutting and pursing cable being extendable from the delivery cannula laterally outwardly and forwardly toward an outer peripheral dimension of a deployed tissue capture basket (326) having a predetermined maximum peripheral diametric extent effective to provide a circumspective positioning about the targeted tissue volume (354);
   a disposable support housing (100) having forward and rearward portions and coupled in supporting relationship with the delivery cannula at the proximal end portion of the delivery cannula;
   a tissue cutting and capture assembly (329) extending from driving engagement with a drive assembly drive member (324) to a driven engagement portion at a housing assembly (15) and drivably movable along the longitudinal axis from a start orientation to a capture position corresponding with a capture orientation;
   a first motor-actuated cable mounting hub translation assembly (180);
   a second motor-actuated drive tube drive member translation assembly (181);
   an actuator and control assembly having a capture advancement yoke (185) drivingly engagable with the drive assembly drive member (324), the drive assembly drive member driven forwardly by the second motor-actuated drive tube drive member translation assembly (181);
   the housing assembly including a terminal assembly comprising first and second electrical contacts (120, 122) oriented to make contact with corresponding first and second electrical terminals (186) and (188) disposed within a reusable housing (14) that selectively receives a controlled constant current at an elevated frequency and at a predetermined level, the constant current being configured to be applied to the resistively heated portion of electrically conductive cutting and pursing cable from an initial position of the eyelet containing tip of leaf member (391) to a position (392) of the eyelet containing leaf member of a maximum opening of the tissue cutting and capture assembly (329) and to a position whereat the resistively heated portion of the electrically conductive cutting and pursing cable (309) purses down to complete the capture of the targeted tissue volume (354); and
   a rechargeable battery (360) and a circuit board (364) including a programmed microcomputer, all incorporated within the reusable housing (14) to provide a source of controlled constant current, first and second motor constant voltage sources and all operator actuation functions, visual cues, audible cues and displays.

27. The apparatus of claim 26, wherein the elevated frequency of the constant current source is in the range from 50 KHz to 100 KHz.

* * * * *

UNITED STATES PATENT AND TRADEMARK OFFICE
CERTIFICATE OF CORRECTION

| | |
|---|---|
| PATENT NO. | : 11,737,808 B2 |
| APPLICATION NO. | : 15/877730 |
| DATED | : August 29, 2023 |
| INVENTOR(S) | : Philip E. Eggers and Andrew Eggers |

It is certified that error appears in the above-identified patent and that said Letters Patent is hereby corrected as shown below:

In the Specification

In Column 37, Line 60, after "D7 = 0.60 to 1.00" insert --mm--

Signed and Sealed this
Twelfth Day of March, 2024

Katherine Kelly Vidal
*Director of the United States Patent and Trademark Office*